United States Patent
Ishibashi et al.

(10) Patent No.: US 6,174,877 B1
(45) Date of Patent: Jan. 16, 2001

(54) CARBAPENEM COMPOUND, THEIR PRODUCTION AND USE

(75) Inventors: Yukio Ishibashi, Toyonaka; Shinichi Imamura, Osaka; Tetsuo Miwa, Kobe, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/101,470

(22) PCT Filed: Jan. 9, 1997

(86) PCT No.: PCT/JP97/00025

§ 371 Date: Jul. 10, 1998

§ 102(e) Date: Jul. 10, 1998

(87) PCT Pub. No.: WO97/25325

PCT Pub. Date: Jul. 17, 1997

(30) Foreign Application Priority Data

Jan. 12, 1996 (JP) .................................... 8-004282

(51) Int. Cl.⁷ ........................ A61K 31/40; C07D 487/04
(52) U.S. Cl. ....................... 514/210.04; 540/350
(58) Field of Search .................. 540/350; 514/210, 514/210.04

(56) References Cited

U.S. PATENT DOCUMENTS 4,413,000  11/1983  Eglington ........................ 424/269

FOREIGN PATENT DOCUMENTS

| | | |
|---|---|---|
| 0 038 869 | 11/1981 | (EP) . |
| 0 170 073 | 2/1986 | (EP) . |
| 2 128 187 | 4/1984 | (GB) . |
| 63-63680 | 3/1988 | (JP) . |
| 7-196660 | 8/1995 | (JP) . |
| 93/19072 | 9/1993 | (WO) . |

*Primary Examiner*—Richard L. Raymond
*Assistant Examiner*—Pananaram K Sripada
(74) *Attorney, Agent, or Firm*—Wenderoth, Lind & Ponack, L.L.P.

(57) ABSTRACT

A cephem compound of the formula:

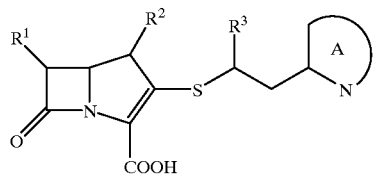

wherein $R^1$ stands for an optionally substituted lower alkyl group, $R^2$ stands for H or a lower alkyl group, $R^3$ stands for H, an optionally substituted hydrocarbon group, cyano group, a lower alkyloxy group or a lower alkylthio group, and the ring A stands for an optionally substituted non-quaternarized nitrogen-containing heterocyclic ring, provided that, when A is unsubstituted 2-pyridyl group, $R^3$ stands for a group other than hydrogen, or their esters or salts, has excellent antibacterial activities, oral absorbability and stability, and is useful as an antibacterial agent.

14 Claims, No Drawings

CARBAPENEM COMPOUND, THEIR PRODUCTION AND USE

TECHNICAL FIELD

This invention relates to a novel carbapenem compound having excellent antibacterial activities and oral absorbability or its esters or salts. The carbapenem compounds or their esters or salts of this invention can be used as an antibacterial agent.

BACKGROUND ART

There have been known a variety of carbapenem compounds, some of those compounds have been put on practical use and commercially available. For example, in JPA S60(1985)-233076, there is disclosed (1R,5S,6S)-2-[(3S,5S)-5-dimethylaminocarbonylpyrrolidin-3-ylthio]-6-[((R)-1-hydroxyethyl]-1-methylcarbapen-2-em-3-carboxylic acid, i.e. Meropenem.

And, in EP-A-289801, there is disclosed (1R,5S,6S)-2-[(6,7-dihydro-5H-pyrazolo[1,2-a]pyrazolium-6-yl)thio]-6-[(R)-1-hydroxyethyl]-1-methylcarbapen-2-em-3-carboxylate, i.e. Biapenem.

These compounds are regarded to improve the stability to renal dehydropeptitase (DHP-I) which is considered as a drawback of conventional carbapenem compounds, thus these compounds have now come to be administered singly without combination with an enzyme inhibitor.

On the other hand, on carbapenem substituted with 2-(N-containing aromatic heterocyclic ring) ethylthio group at 2-position, there are several reports.

For example, in AU-A-8319342, there is disclosed compounds represented by the formula

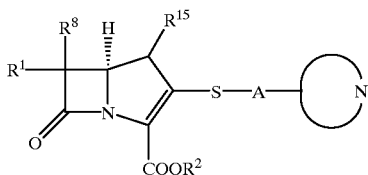

wherein $R^1$ stands for, e.g. H, $R^8$ stands for, e.g. H, $R^{15}$ stands for, e.g. H, $R^{2'}$ stands for a conventional carboxyl-protecting group which is readily removable, A stands for $C_{1-6}$ straight-chain or branched alkylene, and

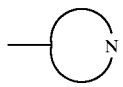

stands for mono-, bi or polycyclic aromatic heterocyclic group, and the ring is linked with A through carbon atom constituting the ring, or their salts. As specific examples, however, only the following three compounds are disclosed,

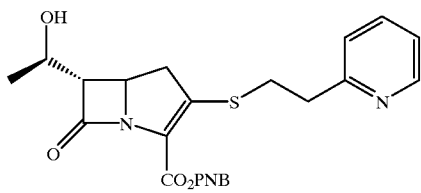

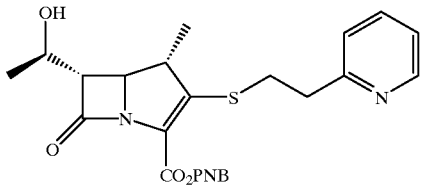

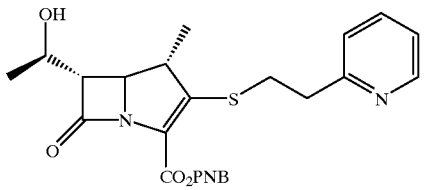

and, these compounds are described only as intermediates for synthesizing a carbapenem compound having, at 2-position of the carbapenem skeleton, a monocyclic or polycyclic N-containing aromatic heterocyclic alkylthio group quaternarized by N-alkylation, but no use of these compounds as antibacterial agents is disclosed.

And, while, in EP-A-170073 and EP-A-242134, there are disclosed compounds having formulae:

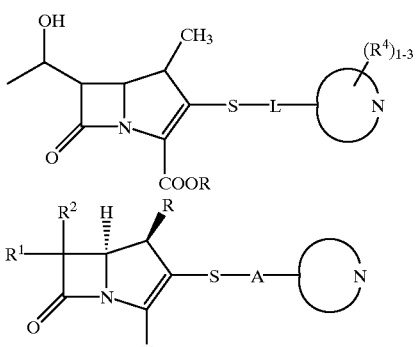

having N-containing aromatic heterocyclic alkylthio group at 2-position of the carbapenem skeleton, these compounds are described only as synthetic intermediates, and no use as antibacterial agents is disclosed at all. And, no specific examples of carbapenem compounds, whose 2-position is substituted with 2-(non-quaternary nitrogen-containing aromatic heterocycle) ethylthio group, are disclosed.

And, in JPA S63(1988)-63680, a (1R)-1-methyl carbapenem compound of the formula:

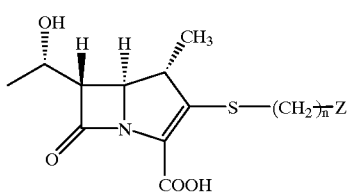

having, at 2-position of the carbapenem skeleton, aromatic ring alkylthio group, or alicyclic or aromatic heterocyclic alkylthio group is described. However, as specific example of the compound having, at its 2-position, an aromatic heterocyclic alkylthio group, disclosed in the above-mentioned official gazette, only a carbapenem compound having 2-(1H-imidazol-1-yl)ethylthio group is given, and the ethylthio group of this compound has the linkage through nitrogen atom on the aromatic heterocyclic ring.

Further, in AU 9336488, a (1R)-1-methyl carbapenem compounds of the formula:

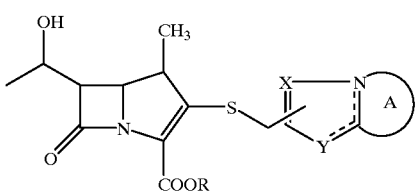

wherein R is hydrogen, anion charge or an ester residue, and

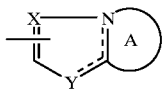

wherein X, Y is the same or different, N or —CH═, one of the portion of dotted line is a single bond and the other portion of dotted line is a double bond, is a bicyclic heterocyclic ring, is described. However, this reference does not show the compound having at 2-position of carbapenem skelton, a bicyclic heterocyclic ring-ethylthio group.

Carbapenem compounds now commercially available are poor in absorbability from digestive canal, which are used only as injectable preparations and are not put on practical use as orally administrable preparations.

Circumstances being such as above, clinically useful carbapenem compounds having, besides a broad antibacterial spectrum, strong antibacterial activities and stability to DHP-I, good oral absorbability have been ardently desired.

DISCLOSURE OF INVENTION

As a result of extensive studies diligently conducted, the present inventors synthesized, for the first time, a carbapenem represented by the formula:

(I)

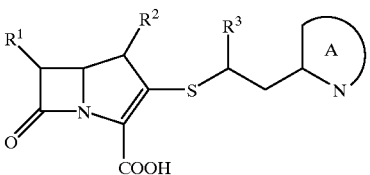

wherein $R^1$ stands for an optionally substituted lower alkyl group, $R^2$ stands for H or a lower alkyl group, $R^3$ stands for H, an optionally substituted hydrocarbon group, cyano group, a lower alkyloxy group or a lower alkylthio group and ring A stands for an optionally substituted non-quaternarized N-containing aromatic heterocyclic ring, provided that when A is unsubstituted 2-pyridyl group, $R^3$ stands for a group other than H, or its ester or salt [sometimes abbreviated as Compound (I)], and found that this novel carbapenem compound, based on its specific chemical structure, shows unexpectedly excellent antibacterial activities against a broad range of pathogenic bacteria from gram-positive bacteria to gram-negative bacteria, and has clinically useful properties, for example, excellent oral absorbability. Based on these findings, the present invention has been accomplished.

More specifically, the present invention relates to
(1) Compound (I),
(2) a method of producing Compound (I), which comprises reacting a compound of the formula:

(II)

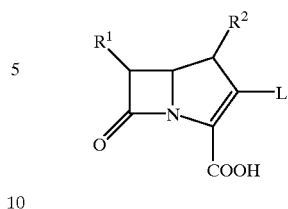

wherein L is a group capable of leaving, and other symbols are of the same meaning as defined above, or its ester or salt with a compound of the formula:

(III)

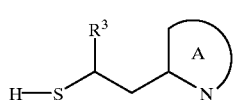

wherein symbols are of the same meaning as defined above, or its salt, or reacting a compound of the formula:

(IV)

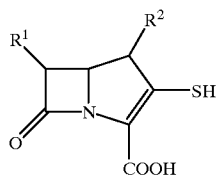

wherein symbols are of the same meaning as defined above, or its ester or salt with a compound represented by the formula:

(V)

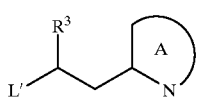

wherein L' stands for a group capable of leaving and other symbols are of the same meaning as defined above, and
(3) a medicinal agent containing Compound (I).

Compound (I) of this invention shows excellent antibacterial activities against a broad range of pathogenic bacteria from gram-positive to gram-negative bacteria, and shows antibacterial activity not only by subcutaneous injection but also by oral administration.

In the above-mentioned formulae, as lower alkyl group of the optionally substituted lower alkyl group shown by $R^1$, use is made of $C_{1-4}$ alkyl groups. Examples of the substituents include cyano group, amino group, mono- or di- $C_{1-4}$ alkylamino group, hydroxyl group, $C_{1-4}$ alkyloxy group, carbamoyloxy group, $C_{1-4}$ alkylthio group, $C_{1-4}$ alkylsulfonyl group, halogen, sulfamoyl group, $C_{1-4}$ alkyloxycarbonyl group and sulfoxy group. Number of these substituents ranges preferably from 1 to 3, and, when the number of these substituents is 2 or more, they may be the same as or different from one another.

In the case where the alkyl group is substituted with amino group or hydroxyl group, these substituents may optionally be protected with a readily removable protective group, preferably exemplified by a silyl group such as trimethylsilyl, triethylsilyl or t-butyldimethylsilyl; and alkoxycarbonyl group such as allyloxycarbonyl, t-butoxycarbonyl, benzyloxycarbonyl or p-nitrobenzyloxycarbonyl.

More preferable examples of $R^1$ include groups representable by the formula:

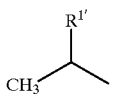

wherein $R^{1'}$ stands for H, halogen, or, respectively optionally substituted hydroxyl group or amino group. As substituents of the hydroxyl group or amino group shown by $R^{1'}$, use is made of, for example, removable protective groups mentioned as above. More preferable examples of $R^{1'}$ include hydroxyl group. Especially preferable examples of $R^1$ include (1R)-hydroxyethyl group.

As $R^2$ of the above-mentioned formula, use is made of H or a lower alkyl group. As the lower alkyl group, use is made of, for example, $C_{1-4}$ alkyl group, preferably methyl group.

As $R^3$ of the above-mentioned formula, use is made of H, an optionally substituted hydrocarbon group, cyano group, a lower alkyloxy group or a lower alkylthio group. As hydrocarbon group of the optionally substituted hydrocarbon group, use is made of, for example, $C_{1-6}$ alkyl group and $C_{2-6}$ alkenyl group, preferably $C_{1-6}$ alkyl group, especially methyl, ethyl, propyl or isopropyl. Number of substituents of the optionally substituted hydrocarbon group ranges from 1 to 3, and, when the number of substituents is two or more, they may be the same as or different from one another. Examples of such substituents include halogen, hydroxyl group, $C_{1-6}$ alkyloxy group, amino group, mono- or di-$C_{1-4}$ alkylamino group. As lower alkyl group of the lower alkyloxy group or the lower alkylthio group, use is made of $C_{1-6}$ alkyl group, preferably, for example, methyl and ethyl. As $R^3$ of the above mentioned formula, an optionally substituted lower alkyl group and cyano group are preferable. Among them, a $C_{1-6}$ alkyl group having hydroxyl or $C_{1-4}$ alkyloxy is the most preferable.

Ring A of the above-mentioned formula stands for an optionally substituted non-quaternarized aromatic heterocyclic ring. As such heterocyclic ring, use is made of, for example, a 5- or 6-membered heterocyclic group containing 1 to 4 hetero-atoms such as nitrogen atom, oxygen atom or sulfur atom, and not containing a quaternarized nitrogen atom, which are exemplified by a 5-membered monocyclic compound such as pyrrole, imidazole, pyrazole, triazole (e.g. 1,2,3-triazole, 1,2,4-triazole), tetrazole, thiazole, isothiazole, oxazole, isoxazole; a 6-membered monocyclic compound such as pyridine, pyrazine, pyrimidine or pyridazine; and a condensed cyclic compound such as purine, pyrrolopyrimidine, pyridopyrimidine, imidazopyrazine, imidazopyridine, imidazopyrimidine, imidazolthiazole, imidazopyridazine or pyrazolopyrimidine. And, the ring A may optionally have, besides the ethylthio group linked with the carbapenem skeleton, 1 to 3 substituents on the ring-forming carbon atom and nitrogen atom. When the number of those substituents is two or more, they may be the same as or different from one another. Those substituents are exemplified by halogen, hydroxy group, cyano group or respectively optionally substituted amino group, carbamoyl group, $C_{1-6}$ alkyl group, $C_{6-10}$ aryl group, 3- to 7-membered heterocyclic group containing 1 to 4 hetero atoms such as nitrogen atom, oxygen atom or sulfur atom (e.g. 2-pyridyl), $C_{1-6}$ alkyloxy group or $C_{1-6}$ alkylthio group. As substituents of the amino group, carbamoyl group, $C_{1-6}$ alkyl group, $C_{6-10}$ aryl group, 3- to 7-membered heterocyclic group containing 1 to 4 hetero-atoms such as nitrogen atom, oxygen atom or sulfur atom, $C_{1-6}$ alkyloxy group or $C_{1-6}$ alkylthio group, mention is made of those further substituted with, at any structurally possible positions, 1 to 3 substituents including, for example, halogen, hydroxyl group, $C_{1-6}$ alkyloxy group, amino group, mono- or di-$C_{1-4}$ alkylamino group. Ring A is linked with the carbapenem skeleton, through the ethylthio group, from a carbon atom adjacent to a ring-forming nitrogen atom.

The carboxyl group at 3-position of carbapenem may optionally form ester similar to the ester readily removable in a living body, which is employable at, for example, 4-position of cephalosporin skeleton (ester convertible to so-called prodrug). The carboxyl group thus esterified is shown by COOR. Specific examples of R include groups represented by the formula:

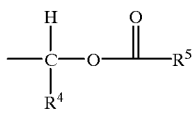

wherein $R^4$ stands for H or respectively optionally substituted $C_{1-6}$ alkyl group or $C_{3-6}$ cycloalkyl group, $R^5$ stands for respectively optionally substituted $C_{1-10}$ alkyl group, $C_{3-10}$ cycloalkyl group, $C_{1-10}$ alkyloxy group, $C_{3-10}$ cycloalkyloxy group, $C_{3-10}$ cycloalkyl $C_{1-6}$ alkyl group, $C_{3-10}$ cycloalkyl $C_{1-6}$ alkyloxy group, $C_{2-6}$ alkenyl group, $C_{6-10}$ aryl group or $C_{7-12}$ aralkyl group.

Examples of the substituents of respectively optionally substituted $C_{1-6}$ alkyl group or $C_{3-6}$ cycloalkyl group shown by $R^4$, and respectively optionally substituted $C_{1-10}$ alkyl group, $C_{3-10}$ cycloalkyl group, $C_{1-10}$ alkyloxy group, $C_{3-10}$ cycloalkyloxy group, $C_{3-10}$ cycloalkyl $C_{1-6}$ alkyl group, $C_{3-10}$ cycloalkyl $C_{1-6}$ alkyloxy group, $C_{2-6}$ alkenyl group, $C_{6-10}$ aryl group or $C_{7-12}$ aralkyl group shown by $R^5$ include cyano group, nitro group, hydroxyl group, $C_{1-4}$ alkyloxy group, carbamoyloxy group, $C_{1-4}$ alkylthio group and halogen. Number of these substituents ranges preferably from 1 to 3. When the number is two or more, these substituents may be the same as or different from one another.

Especially preferable examples of R include $C_{1-4}$ alkyl groups optionally substituted with, for example, $C_{1-6}$ alkanoyloxy group, $C_{1-6}$ alkyloxy group, $C_{1-6}$ alkyloxycarbonyloxy or $C_{3-10}$ cycloalkyloxy-carbonyloxy group [e.g. acetoxymethyl group, 1-acetoxyethyl group, 1-acetoxypropyl group, pivaloyloxymethyl group, isopropyloxycarbonyloxymethyl group, 1-(isopropyloxycarbonyloxy)ethyl group, cyclohexyloxycarbonyloxymethyl group, 1-(cyclohexyloxycarbonyloxy)ethyl group, ethoxycarbonyloxymethyl group, and 1-(ethoxycarbonyloxy)ethyl group], phthalidyl group or (2-oxo-5-methyl-1,3-dioxol-4-yl)methyl group.

As salts of the compound represented by the above-mentioned formula (I) or its ester, pharmacologically or synthetically acceptable ones are preferably mentioned. As such salts, use is made of salts with inorganic bases, salts with organic bases, salts with inorganic acids, salts with organic acids and salts with basic or acid amino acid. Examples of such inorganic bases include alkali metals (e.g. sodium and potassium), alkaline earth metals (e.g. calcium and magnesium), examples of organic bases include trimethylamine, triethylamine, pyridine, picoline, N,N'-dibenzylethylenediamine, ethanolamine, diethanolamine, tris(hydroxymethylamino)methane and dicyclohexylamine, examples of inorganic acids include hydrochloric acid, hydrobromic acid, sulfuric acid, nitric acid and phosphoric acid, examples of organic acids include formic acid, acetic acid, trifluoroacetic acid, oxalic acid, tartaric acid, fumaric acid, maleic acid, methanesulfonic acid, trifluoromethanesulfonic acid, benzenesulfonic acid and p-toluenesulfonic acid, and examples of basic or acidic amino acid include arginine, lysine, ornithine, aspartic acid and glutamic acid. Among these salts, salts with bases (i.e. salts with inorganic bases, salts with organic bases and salts with basic amino acids) mean salts formable when an alkali-reactive group such as carboxyl group exists in the carboxyl group shown by COOH of the formula (I) or in the compound represented by the formula (I) or in its ester, and salts with acids (i.e. salts with inorganic acids, salts with organic acids and salts with acidic amino acids) mean salts formable when a basic group such as amino group exists in the compound represented by the formula (I) or its ester.

The compound of the formula (I) and an ester or salt thereof may either be hydrate or a non-hydrate.

Where the compound has one or more asymmetric C-atoms in the substituent at the 2-position of carbapenem skeleton, all possible diastereomers are included within the scope of the invention.

Specific examples of the respective substituents in this specifications are, unless otherwise specified, as follows.

Halogen: fluoro, chloro and bromo;

$C_{1-4}$ alkyl group: methyl, ethyl, propyl, isopropyl, butyl, isobutyl and t-butyl;

$C_{1-6}$ alkyl group: methyl, ethyl, propyl, isopropyl, butyl, isobutyl, t-butyl, pentyl, 2,2-dimethylpropyl and hexyl;

$C_{1-10}$ alkyl group: methyl, ethyl, propyl, isopropyl, butyl, isobutyl, t-butyl, pentyl, 2,2-dimethylpropyl, hexyl, heptyl and decyl;

$C_{2-6}$ alkenyl group: vinyl, ally, and crotyl;

$C_{6-10}$ aryl group: phenyl and naphthyl;

$C_{7-12}$ aralkyl group: benzyl and phenethyl;

$C_{3-6}$ cycloalkyl group: cyclopropyl, cyclobutyl, cyclopentyl and cyclohexyl;

$C_{3-10}$ cycloalkyl group: cyclopropyl, cyclobutyl, cyclopentyl, cyclohexyl, cycloheptyl, cyclooctyl and cyclodecyl;

$C_{3-10}$ cycloalkyloxy group: cyclopropyloxy, cyclobutyloxy, cyclopentyloxy, cyclohexyloxy, cycloheptyloxy, cyclooctyloxy and cyclodecyloxy;

$C_{1-6}$ alkanoyloxy group: acetyloxy, propionyloxy, butyryloxy, valeryloxy and pivaloyloxy;

$C_{3-10}$ cycloalkyl $C_{1-6}$ alkyl group: cyclopropylmethyl, cyclobutylmethyl, cyclopentylmethyl, cyclohexylmethyl, cycloheptylmethyl, cyclooctylmethyl and cyclodecylmethyl;

$C_{3-10}$ cycloalkyl $C_{1-6}$ alkyloxy group: cyclopropylmethyloxy, cyclobutylmethyloxy, cyclopentylmethyloxy, cyclohexylmethyloxy, cycloheptylmethyloxy, cyclooctylmethyloxy, and cyclodecylmethyloxy;

$C_{1-4}$ alkyloxy group: methyloxy, ethyloxy, propyloxy, isopropyloxy, butyloxy, isobutyloxy and t-butyloxy;

$C_{1-6}$ alkyloxy group: methyloxy, ethyloxy, propyloxy, isopropyloxy, butyloxy, isobutyloxy, t-butyloxy, pentyloxy, 2,2-dimethylpropyloxy and hexyloxy;

$C_{1-10}$ alkyloxy group: methyloxy, ethyloxy, propyloxy, isopropyloxy, butyloxy, isobutyloxy, t-butyloxy, pentyloxy, 2,2-dimethylpropyloxy, hexyloxy, heptyloxy and decyloxy;

$C_{1-4}$ alkylthio group: methylthio, ethylthio, propylthio, butylthio, isobutylthio and t-butylthio;

$C_{1-6}$ alkylthio group: methylthio, ethylthio, propylthio, butylthio, isobutylthio, t-butylthio, pentylthio, 2,2-dimethylpropylthio and hexylthio;

$C_{1-4}$ alkylsulfonyl group: methylsulfonyl, ethylsulfonyl, propylsulfonyl, isopropylsulfonyl, butylsulfonyl, isobutylsulfonyl and t-butylsulfonyl;

Mono- or di-$C_{1-4}$ alkylamino group: methylamino and dimethylamino;

$C_{1-6}$ alkyl-carbonyloxy group: acetyloxy, propionyloxy and butyryloxy;

$C_{1-4}$ alkyloxy-carbonyl group: methyloxycarbonyl, ethyloxycarbonyl, propyloxycarbonyl, isopropyloxycarbonyl, butyloxycarbonyl, isobutyloxycarbonyl and t-butyloxycarbonyl;

$C_{1-6}$ alkyloxy-carbonyloxy group: methyloxycarbonyloxy, ethyloxycarbonyloxy, propyloxycarbonyloxy, isopropyloxycarbonyloxy, butyloxycarbonyloxy, isobutyloxycarbonyloxy, t-butyloxycarbonyloxy, pentyloxycarbonyloxy, 2,2-dimethylpropyloxycarbonyloxy, and hexyloxycarbonyloxy;

$C_{3-10}$ cycloalkyloxy-carbonyloxy: cyclopropyloxycarbonyloxy, cyclobutyloxycarbonyloxy, cyclopentyloxycarbonyloxy, cyclohexyloxycarbonyloxy, cycloheptyloxycarbonyloxy, cyclooctyloxycarbonyloxy and cyclodecyloxycarbonyloxy.

Among the compounds in the present invention, the following compounds and an ester or salt thereof are preferable.

(4R,5R,6R)-6-[(R)-1-hydroxyethyl]-4-methyl-7-oxo-3-[2-(1,2,3-triazol-4-yl)ethylthio]-1-azabicyclo[3.2.0]hept-2-ene-2-carboxylic acid, (4R,5R,6R)-6-[(R)-1-hydroxyethyl]-4-methyl-7-oxo-3-[2-(3-pyrazolyl)ethylthio]-1-azabicyclo[3.2.0]hept-2-ene-2-carboxylic acid, (4R,5R,6R)-6-[(R)-1-hydroxyethyl]-4-methyl-3-[1-methyl-2-(3-pyridazinyl)ethylthio]-7-oxo-1-azabicyclo[3.2.0]hept-2-ene-2-carboxylic acid, (4R,5R,6R)-6-[(R)-1-hydroxyethyl]-3-[2-(imidazo[1,2-a]pyridine-2-yl)ethylthio]-4-methyl-7-oxo-1-azabicyclo[3.2.0]hept-2-ene-2-carboxylic acid, (4R,5R,6R)-3-[2-(6-aminoimidazo[1,2-a]pyridin-2-yl)ethylthio]-6-[(R)-1-hydroxyethyl]-4-methyl-7-oxo-1-azabicyclo[3.2.0]hept-2-ene-2-carboxylic acid, (4R,5R,6R)-6-[(R)-1-hydroxyethyl]-3-[2-(imidazo[1,2-a]pyrimidin-2-yl)ethylthio]-4-methyl-7-oxo-1-azabicyclo[3.2.0]hept-2-ene-2-carboxylic acid, (4R,5R,6R)-6-[(R)-1-hydroxyethyl]-4-methyl-7-oxo-3-[2-(5-ureidoimidazo[1,2-a]pyridin-2-yl)ethylthio]-1-azabicyclo[3.2.0]hept-2-ene-2-carboxylic acid, (4R,5R,6R)-6-[(R)-1-hydroxyethyl]-3-[2-(imidazo[1,5-a]pyridin-3-yl)ethylthio]-4-methyl-7-oxo-1-azabicyclo[3.2.0]hept-2-ene-2-carboxylic acid, (4R,5R,6R)-6-[(R)-1-hydroxyethyl]-3-[2-(imidazo[1,2-a]pyrazin-2-yl)ethylthio]-4-methyl-7-oxo-1-azabicyclo[3.2.0]hept-2-ene-2-carboxylic acid, (4R,5R,6R)-6-[(R)-1-hydroxyethyl]-3-[2-(imidazo[5,1-b]thiazol-5-yl)ethylthio]-4-methyl-7-oxo-1-azabicyclo[3.2.0]hept-2-ene-2-carboxylic acid.

Compound (I) can be produced by, for example, the following Methods 1 to 3.

Production Method 1

The compound (I) of this invention can be produced by, for example, allowing the compound:

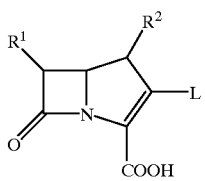

(II)

wherein L stands for a group capable of leaving, and other symbols are of the same meaning as defined above, or an ester thereof or a salt thereof to react with a compound represented by the formula:

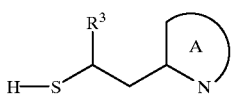

(III)

wherein symbols are of the same meaning as defined above, or a salt thereof.

As the group capable of leaving shown by L in the compound (II), use is made of a leaving group commonly employed in the field of organic synthetic chemistry (leaving groups described in, for example, Compendium of Organic Synthetic Methods, Vol.1 to Vol.7, John Wely & Sons Inc., New York (1971–1992) and R. C. Larock, Comprehensive Organic Transformation, VCH, New York (1989)). Practical examples of L include $C_{1-6}$ alkanesulfonyloxy groups optionally substituted with 1 to 3 halogen atoms (e.g. methanesulfonyloxy and trifluoromethanesulfonyloxy), $C_{6-10}$ allenesulfonyloxy groups optionally substituted with $C_{1-4}$ alkyl group (e.g. benzenesulfonyloxy or toluenesulfonyloxy), di-$C_{1-6}$ alkylphosphonoxy group (e.g. dimethylphosphonoxy), di-$C_{6-10}$ arylphosphonoxy group (e.g. diphenylphosphonoxy)], halogen (e.g. chloro, bromo), $C_{1-6}$ alkanesulfinyl (e.g. methanesulfinyl) or $C_{6-10}$ allene sulfinyl group (e.g. benzenesulfinyl). More preferable L is diphenylphosphonoxy group.

As esters or salts of the compound (II), use can be made of, for example, esters or salts similar to those of the compound represented by the formula (I).

As salts of the compound (III), use can be made of, for example, alkali metal (e.g. sodium or potassium) salt, alkaline earth metal (e.g. calcium or magnesium) salt and ammonium salt.

When reactive groups such as amino group, hydroxyl group or carboxyl group are contained in the structural formulae of the compounds (II) and (III), these groups may optionally be protected, in accordance with a conventional method, with the protective groups mentioned below. After completion of the reaction, these protective groups can be removed.

The reaction between the compound (II) and the compound (III) proceeds advantageously usually in the presence of a base. Examples of the base include organic amine such as triethylamine and diisopropylethylamine and basic inorganic salts such as sodium hydrogencarbonate and potassium carbonate. This reaction is conducted usually by stirring in an inert solvent. As the inert solvents to be employed for the reaction, any one can be used so long as it does not hamper the reaction, which is preferably exemplified by aromatic hydrocarbons such as benzene, toluene and xylene, ethers such as dioxane, diethoxyethane and tetrahydrofuran, halogenated hydrocarbons such as dichloromethane and chloroform, alkyl nitrites such as acetonitrile and propionitrile, nitroalkanes such as nitromethane and nitroethane and amides such as dimethylformamide and dimethylacetamide. While the reaction temperature varies with, among others, the starting compounds, kinds of bases then added and kinds of solvents then employed, it ranges usually from –40° C. to 100° C., preferably from –30° C. to 50° C. The reaction time ranges usually from one minute to 48 hours, preferably from about 15 minutes to about 24 hours.

The method of producing the compound (II) is known in the field of carbapenem (e.g. JPA S57(1982)-12318 and JPA S64(1989)-25780).

The compound (III) can be produced by the methods described in literature references or methods analogous thereto. As such literature references, mention is made of, for example, Compendium of Organic Synthetic Methods, Vol.1 to Vol.7, John Wely & Sons Inc., New York (1971–1992), Comprehensive Organic Synthesis, Vol.1–Vol.9, Pergamon Press, Oxford (1991) and R. C. Larock, Comprehensive Organic Transformation, VCH, New York (1989).

The compound (III) can be produced, practically, by converting the hydroxyl group of the compound of the formula:

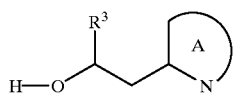

(III')

wherein symbols are of the same meaning as defined above, to convert into mercapto group by the method described in the above-mentioned literature references. The compound represented by the formula (III') can also be produced by methods described in, for example, Chemistry of Heterocyclic Compounds, John Wely & Sons Inc. New York, Advance in Heterocyclic Chemistry, Academic Press, or Organic Synthesis Vol.23, p.83.

Production Method 2

The compound (I) of this invention can be produced also by allowing a compound of the formula:

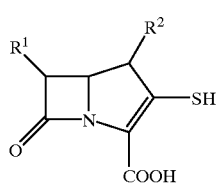

(IV)

wherein symbols are of the same meaning as defined above, or its ester or salt to react with a compound of the formula:

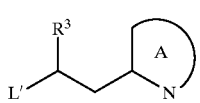

(V)

wherein L' stands for a group capable of leaving, and other symbols are of the same meaning as defined above.

The reaction between the compound (IV) and the compound (V) proceeds usually in the presence of a base.

Examples of the base include organic amines such as diisopropylethylamine, triethylamine and 4-dimethylaminopyridine; and basic inorganic salts such as sodium hydrogencarbonate, potassium hydrogencarbonate, sodium carbonate and potassium carbonate. The reaction can be allowed to proceed by stirring a mixture of the compound (IV) or its ester or salt and the compound (V) in amount of about 1 to 3 times as much mol., preferably about 1 to about 1.8 times as much mol., of the compound (IV) in an inert solvent. As the inorganic solvent, use is made of solvents similar to those employed for the reaction of the compound (II) or its ester or salt with the compound (III), and, more preferably, amides such as N,N-dimethylformamide and N,N-dimethylacetamide. While the reaction temperature varies with starting compounds, kinds of bases added and kinds of solvents, it ranges usually from −70° C. to 0° C., preferably from −50° C. to −20° C. The reaction time ranges usually from about 10 seconds to about 5 hours, preferably from about 1 minutes to 2 hours. The reaction is preferably conducted in an inert gas, for example, nitrogen gas or argon gas streams.

When reactive groups such as amino group, hydroxyl group or carboxyl group are contained in the structural formulae of the compounds (IV) and (V), these groups may optionally be protected, in accordance with a conventional method, with the protective groups mentioned below. After completion of the reaction, these protective groups can be removed.

The compound of formula (IV) or its ester or salt can be produced by allowing, for example, the compound of formula (II) or its ester or salt to react with hydrosulfide such as sodium hydrosulfide and trimethylammonium sulfide or a reactive derivative thereof. This reaction proceeds by stirring a mixture of the compound of formula (II) or its ester or salt and the above-mentioned hydrosulfide in an amount of about 1 to about 5 times as much mol., preferably about 1 to about 2 times as much mol., relative to the compound of formula (II) or its ester or salt. As the inert solvent, use is made of, for example, N,N-dimethylformamide, N,N-dimethylacetamide, tetrahydrofuran and acetonitrile. The reaction temperature ranges from −70° C. to 20° C., preferably from −50° C. to −20° C. The reaction time ranges usually from about 10 seconds to 3 hours, preferably from about 1 minute to 1 hour. The reaction is conducted optionally in the presence of a base. As the base, mention is made of, for example, organic amines such as diisopropylethylamine and triethylamine; and basic inorganic salt such as sodium hydrogencarbonate and potassium carbonate. The reaction is preferably conducted in an inert gas, for example, nitrogen gas or argon gas streams. The compound of formula (IV) or its ester or salt produced by the above-mentioned reaction can be used optionally for the subsequent reaction as it is, without isolation and purification.

While, as groups capable of leaving shown by L' in the compound (V), use is made of groups similar to those shown by L in the compound (II), preferable examples of L' include $C_{1-6}$ alkanesulfonyloxy groups optionally substituted with 1 to 3 halogen atoms (e.g. methanesulfonyloxy group and trifluoromethanesulfonyloxy group), $C_{6-10}$ allenesulfonyloxy groups optionally substituted with $C_{1-4}$ alkyl groups (e.g. benzenesulfonyloxy group and toluenesulfonyloxy group) or halogen atoms (e.g. bromine and iodine), and, as more preferable L', mention is made of trifluoromethanesulfonyloxy group.

The compound (V) can be produced by conventional methods disclosed in the literature references described in connection with the method of producing the compound (III). And, when the group capable of leaving shown by L' of the compound (V) is trifluoromethanesulfonyloxy group, the compound of the formula (V: L'=$OS_2CF_3$) can be produced by allowing the compound represented by the above-mentioned formula (III') to react with trifluoromethanesulfonic anhydride in amount of about 0.8 to about 1.5 times as much mol., preferably about 1 to 1.2 times as much mol. This reaction is conducted usually in an inert solvent such as dichloromethane and tetrahydrofuran, or a basic solvent such as pyridine. While the reaction temperature varies with starting compounds, kinds of the base added and kinds of solvents, it ranges usually from −70° C. to room temperature, preferably from −60° C. to −20° C., and, the reaction time ranges usually from about 10 seconds to about 5 hours, preferably from one minute to about one hour. The reaction proceeds advantageously usually in the presence of a base. Examples of the base employed in this reaction include organic amines such as diisopropylethylamine, triethylamine and 4-dimethylaminopyridine, basic inorganic salts such as sodium hydrogencarbonate, potassium hydrogencarbonate, sodium carbonate and potassium carbonate, metal hydrides such as sodium hydride and potassium hydride, and organometal compounds such as butyl lithium and methyl magnesium bromide. The reaction is conducted preferably in the streams of an inert gas such as nitrogen gas or argon gas.

While the compound (V) produced by, for example, the above-mentioned reactions can be isolated by a conventional purification means, it can also be used as it is for the subsequent reaction without isolation and purification.

Production Method 3

And, the compound (I) of this invention can also be produced by, for example, subjecting the compound of the formula:

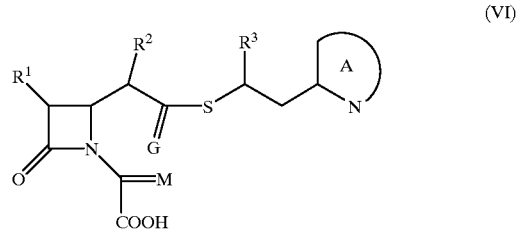

wherein M and G stand for groups forming a double bond by reacting with each other, in other words, groups forming a double bond by the reaction of M and G followed by leaving, and other symbols are of the same meaning as described above, or its ester or salt to ring-closing reaction. As practical examples of M and G, mention is made of, besides =O, =S and =Se, those disclosed in JPA H4(1992)-179389.

As the ring-closure reaction, per se known methods (e.g. Annual Reports in Organic Synthesis, 1975–1993, Academic Press, Inc. San Diego, Advanced Organic Chemistry Second Edition Plenum Press New York and London (1983)) can be employed. More specifically, Wittig type reaction (Wittig, Horner, Emmons reaction), Peterson type reaction, Aldol type reaction accompanied with dehydration and McMurry type reaction using a metal of low electron value. More desirably, a Wittig type reaction employing as M, for example, a compound of the formula:

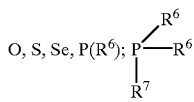

wherein $R^6$ and $R^7$ stand for $C_{1-6}$ alkyloxy group, $C_{1-6}$ alkyl group or $C_{6-10}$ aryl group, is mentioned. As more practical methods, the following methods, for example, can be mentioned.

Production Method 3-1

The compound (I) can also be produced by allowing a compound of the formula:

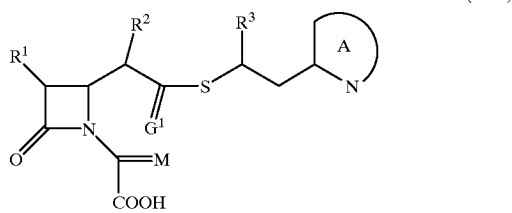

(VI-1)

wherein G1 stands for O or S, and other symbols are of the same meaning as defined above, or an ester or salt thereof, to react with a compound of the formulae

 (VII),

 (VIII)

(wherein $R^6$ and R7 are of the same meaning as defined above), followed by, depending on necessity, removing the protective groups.

When reactive groups such as amino group, hydroxyl group or carboxyl group are contained in the structural formula of the compound (VI-1), these groups may optionally be protected with the protective groups described below in accordance with a conventional method. After completion of the reaction, these protective groups can be removed by a conventional method.

These reactions are conducted usually under heating in the absence of solvent or in an inert solvent. While, as the inert solvent to be employed for the reaction, any one can be used so long as it does not hamper the reaction, preferable examples of such solvents include aromatic hydrocarbons such as benzene, toluene and xylene, ethers such as dioxane, diethoxyethane and tetrahydrofuran, or halogenated hydrocarbons such as dichloromethane and chloroform. The amount of the compound (VII) or (VIII) to be employed is 2 molar equivalents or more, preferably 2 to 10 molar equivalents, of the compound (VI-1). While the reaction temperature varies with the starting compounds (VI-1), (VII), (VIII) and kinds of the solvent, it ranges usually from about 20 to 160° C., preferably from about 80 to 140° C. The reaction time ranges usually from 30 minutes to 100 hours, preferably from 1 to 72 hours.

Production Method 3-2

The compound (I) can be produced by subjecting a compound of the formula:

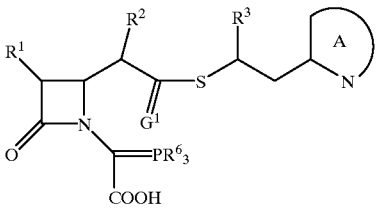

(VI-2)

wherein symbols are of the same meaning as defined above, or its ester or salt to ring-closure reaction, followed by, depending on necessity, removing the protecting groups. Like in the case of Production Method 2-1, when reactive groups such as amino group, hydroxyl group or carboxyl group are contained in the structural formula of the compound (VI-2), these groups may optionally be protected, in accordance with a conventional method, with any of the protecting groups mentioned below, and these protective groups may optionally be removed in accordance with a conventional method.

The ring-closure reaction is conducted in an inert solvent. Preferable examples of the inert solvent include aromatic hydrocarbons, ethers and halogenated hydrocarbons as employed in the above Production Method 2-1. The reaction is conducted under heating at temperatures ranging from about 0 to 160° C., preferably from about 30 to 140° C. While the reaction time depends on the kinds of the compound (VI-2) and the reaction temperature then employed, it ranges usually from about 30 minutes to 100 hours, preferably from one hour to 72 hours.

As esters or salts of the above-mentioned starting compounds, use can be made of, for example, those similar to esters of salts of the compound of the formula (I).

The starting materials employed in Production Method 3, 3-1 and 3-2, i.e. the compounds represented by the formulae (VI), (VI-1) and (VI-2), can be produced by using, for example, compounds represented by the formula (III), by known methods (for example, methods disclosed in JPA S59(1984)-51286, JPA S60(1985)-19764, or Comprehensive Organic Synthesis, Vol.1 to Vol.9, Pergamon Press, Oxford (1991)) or methods analogous or similar thereto.

In these production steps, when an amino group is contained in the structures of the compounds represented by (II), (III), (IV), (V), (VI), (VI-1) and (VI-2), the amino group may preferably be protected with a protecting group. As the amino-protecting group, use is conveniently made of, for example, such ones as employed in the fields of beta-lactam type antibiotics and peptides. Among them, for example, formyl, chloroacetyl, phenyl acetyl, phenoxy acetyl, t-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, trityl and allyloxycarbonyl are preferable. And, when a hydroxyl group is contained in the structures of similar compounds, the hydroxyl group may optionally be protected. As the hydroxyl-protecting group, use is conveniently made of, for example, such ones as employed in the fields of beta-lactam antibiotics and peptides. Among them, use is made of, for example, chloroacetyl, benzyl, p-nitrobenzyl, o-nitrobenzyl, methylthiomethyl, trimethylsilyl, triethylsilyl, t-butyldimethylsilyl, t-butyldiphenylsilyl, 2-tetrahydropyranyl, 4-methoxy-4-tetrahydropyranyl, p-nitrobenzyloxycarbonyl, o-nitrobenzyloxycarbonyl and allyloxycarbonyl. Further, when a carboxyl group is contained in the structures of similar compounds, the carboxyl group may optionally be protected. As the carboxyl-protecting group, use is made of, for example, such ones as employed in the fields of beta-lactam type antibiotics and peptides. Among them, use is made of benzyl, benzhydryl, trityl, p-methoxybenzyl, p-nitrobenzyl, o-nitrobenzyl, phenethyl, 2-trimethylsilylethyl, bis(p-methoxyphenyl) methyl, tertiary butyl and allyl.

The carboxyl group shown by COOH of the object compound (I) may, as described above, optionally form ester which can be readily hydrolized in a living body. The R of the esterified carboxyl group shown by COOR may, when desired, optionally be introduced at the step of producing the compound represented by the general formula (I) or at the stage of the compound represented by the general formula (I). For this introduction reaction, use can be made of a reaction commonly employed for a similar purpose in the field of beta-lactam type antibiotics.

The object compound (I) thus produced can be isolated and purified by conventional means, for example, solvent-extraction, pH change, phasic transfer, salting out, crystallization, recrystallization and chromatography. And, when a protecting group is contained in the reaction product, the compound (I) is produced by, when so desired, removing the protecting group by a conventional method. So far, in the fields of beta-lactam and peptide synthesis, protecting groups of amino, hydroxyl or carboxyl have been sufficiently studied, and the methods of protecting and deprotecting are established. These methods can be utilized in the method of producing the object compound of this invention and in the method of producing intermediates thereof. For example, as the method of removing the said protecting group, use is made of conveniently a conventional means selected from means of using acid, means of using base, means of using 0 value palladium, means of using aluminum chloride, means of using hydrazine, means comprising reduction and means of using sodium N-methyldithiocarbamate.

The compound (I) shows excellent antibacterial activities against gram-positive and gram-negative bacteria including clinically isolated strains, which is remarkably less toxic, and, depending on cases, shows excellent oral absorbability and is physico-chemically and biochemically stable (especially stable against DHP-I), thus being a valuable antibiotic substance. The compound (I) is, therefore, utilized as drugs for man and domestic animals, which can be safely used as an antibacterial agent for the therapy and prophylaxis of infectious diseases caused by various bacteria.

Further, the compound (I) of this invention can be added to animal feed as, for example, a bactericidal agent for preservation of the feed. And, it can also be used as bactericidal agent for clearing harmful bacteria on medical and dental appliances.

The compound (I) of this invention can be used, singly or in combination with any other active components (for example, any other antibiotic agents, anti-inflammatory agents, antipyretics and analgesics), and, depending on necessity, adding, besides pharmaceutically acceptable carriers, adjuvants e.g. a stabilizer and dispersant, as pharmaceutical preparations such as injections, capsules, tablets, liquid medicines (e.g. suspensions and emulsions) formulated by conventional methods. These preparations can be administered non-orally (e.g. intravenous or intramuscular injection) or orally.

Injectable preparations can be provided in a dosage form of ampoules or vials supplemented with a preservative. These preparations may optionally be suspensions, solutions or emulsions in an oleaginous or aqueous medium, which may contain an adequate amount of conventional adjuvants such as a suspending agent, stabilizer and (or) dispersant. The compound (I) of this invention can also be provided in a form of a pulverized or powdery agent, which can be used, by dissolving, just before the actual use, in an adequate solvent such as sterilized water containing no pyrogenic substance.

The compound (I) can be formulated into tablets, capsules, powdery preparations or pulverized preparations for oral administration by adequately mixing with a binder (e.g. syrup, gum arabic, gelatin, sorbitol, tragacanth gum, polyvinyl pyrrolidone and methyl cellulose), a filler (e.g. lactose, sugars, corn starch, calcium phosphate, sorbitol and glycine), a lubricant (e.g. magnesium stearate, talc, polyethylene glycol and silica), a disintegrator (e.g. potato starch) or a wetting agent (e.g. sodium lauryl sulfate). Tablets, powdery preparations and the like can be film-coated by a per se known method. Orally administrable preparations may also be used as liquid preparations e.g. aqueous or oily suspensions, solutions, emulsions, syrups and elixir.

And, these preparations may be mixed with other components, for example, a known antioxidant, preservative, binder, wetting agent, lubricant, sticking agent or flavoring agent. These preparations may further be mixed with any other active components (e.g. any other beta-lactam type antibiotic substances) to give those showing a broader spectrum of antibacterial activities.

The ratio of the compound (I) in the medicinal composition containing the compound (I), though variable with forms of the composition, may be that commonly employed in general antibiotic preparations. For example, in a solid preparation such as capsules, tablets and granules, the ratio of the compound (I) ranges from about 30 to 95 weight %.

The compound (I) can be used, as therapeutic agents of diseases caused by bacterial infection, for the therapy and prophylaxis of infectious diseases from bacteria in man and any other mammalian animals (e.g. mouse, rat, rabbit, dog, cat, cow and pig), as exemplified by respiratory infectious diseases, urinary tract infection, suppurative diseases, inflammatory diseases of biliary tract, intestinal infectious diseases, infectious diseases in the field of obsterics and gynecology, infectious diseases in the field of otorhinology and infectious diseases in the field of surgery. For example, in the case of respiratory infectious diseases, the dosage of the compound (I) per day, though variable with, for example, symptoms of patients, body weights and administration routes, ranges, in non-oral administration, from about 0.5 to 80 mg, preferably from about 2 to 40 mg of the active component [i.e. the compound (I)] per 1 kg of the body weight of adult patients. The administration is preferably conducted intravenously or intramuscularly divided into 1 to 4 doses daily. And, the daily dose of oral administration ranges from about 1 to 500 mg, preferably about 5 to 100 mg, in terms of the active component per 1 kg of the body weight of adult patients, divided into 1 to 3 doses.

BEST MODE FOR CARRYING OUT THE INVENTION

The following Reference Examples and Working Examples will describe the present invention in more detail. These are, however, mere examples and are not intended to limit the scope of this invention.

Elution in the column chromatography in the following Reference Examples and Working Examples was conducted under observation by TLC (thin-layer chromatography). In the TLC observation, as TLC plate, 60$F_{254}$ manufactured by Merck & Co.,Inc. was employed, as the developing solvent, use was made of the solvent employed as the eluent in the column chromatography, and, as the detection method, a UV detector was employed. As silica gel for the column, use was made of kieselguhr 60 (70–230 mesh or 230–400 mesh) manufactured by Merck & Co.,Inc. CHP-20P resin and HP-20SS resin are the products of Mitsubishi Chemical Industries, Ltd. The solvent was used, depending on necessity, after purification and drying. IR spectrum was measured by using IR-810 manufactured by Nihon Bunkosha or FT-200 manufactured by Horiba, Ltd. NMR spectrum was measured, using, as internal or external standard, tetramethyl silane or sodium 3-(trimethylsilyl)propionate, by means of GEMINI 200 (200 MHz) spectrometer manufactured by Varian Co., and all the delta values were shown by ppm. The numerical values shown in parenthesis ( ) are mixture ratios of each solvent by volume. Percent (%) in the mixed solvents means volume %, and in the other case, percent (%) means weight %. Room temperature means 10 to 35° C. Symbols in Reference Examples and Working Examples have the following meanings.

s: singlet
d: doublet
t: triplet
q: quartet
dd: double doublet
ddd: double double doublet
m: multiplet
dt: double triplet
dq: double quartet
td: triple doublet
tt: triple triplet
br: broad
J: coupling constant And, abbreviations in Reference Examples and Working Examples have the following meanings.
THF: tetrahydrofuran
DMF: dimethylformamide
DMA: dimethylacetamide
DMSO: dimethyl sulfoxide
PNB: p-nitrobenzyl (or 4-nitrobenzyl)
Tr: triphenylmethyl Reference Example 1

2-(2-Thiazolyl)ethanol

2-Bromothiazole (5.00 g) was dissolved in diethyl ether (100 ml). To the solution was added dropwise at −60° C. n-butyllithium (1.6M toluene solution, 24.6 ml) over about 20 minutes. The mixture was stirred for 30 minutes for 30 minutes, to which was added ethylene oxide (3 ml). The temperature of the mixture was raised up to −30° C. in the course of two hours. To the reaction mixture was added 10% hydrochloric acid (30 ml), which was shaken and left standing. The resulting aqueous layer was washed with ethyl acetate (100 ml). The aqueous layer was adjusted to pH 7 with a 1N aqueous solution of sodium hydroxide, to which was added sodium chloride to saturation. The mixture was subjected to extraction twice with 50 ml each portion of ethyl acetate. The extract was dried over anhydrous magnesium sulfate and concentrated. The concentrate was purified by means of a column chromatography (carrier: silica gel, 30 g, developing solvent: ethyl acetate) to afford the title compound (0.11 g) as an oily product.

IR(neat): 3300, 1500, 1120, 1050 cm$^{-1}$. $^1$H-NMR(CDCl$_3$) δ: 3.24(2H,t,J=5.4 Hz), 3.30(1H,t,J=6.0 Hz), 4.04(2H,dt,J= 6.0,5.4 Hz), 7.23(1H,d,J=3.2 Hz), 7.71(1H,d,J=3.2 Hz).

REFERENCE EXAMPLE 2

2-(1-Triphenylmethyl-1,2,3-triazol-4-yl)ethanol

In toluene (90 ml) were dissolved triphenylmethyl azide (8.23 g) and 3-butyn-1-ol (2.2 ml). The solution was heated for 60 hours under reflux. The reaction mixture was concentrated under reduced pressure. The concentrate was purified by means of a column chromatography (carrier: silica gel, 150 g, developing solvent: ethyl acetate). The resulting crystalline product was washed with isopropyl ether to give the title compound (3.06 g).

$^1$H-NMR(CDCl$_3$)δ: 2.79(1H,t,J=6.2 Hz), 2.93(2H,t,J=5.8 Hz), 3.96(2H,dt,J=6.2,5.8 Hz), 7.1–7.6(16H,m).

REFERENCE EXAMPLE 3

2-(1-Triphenylmethyl-3-pyrazolyl)ethanol, and 2-(1-triphenylmethyl-4-pyrazolyl)ethanol A mixture of 2-(3-pyrazolyl)ethanol and 2-(4-pyrazolyl) ethanol (2.4:1) (2.50 g) was dissolved in DMF (30 ml). To the solution were added, while stirring, triethylamine (2.26 g) and trityl chloride (6.22 g). The mixture was stirred at 25° C. for one hour, then at 40° C. for one hour. The reaction mixture was diluted with water, which was subjected to extraction with ethyl acetate. The organic layer was washed with an aqueous saline solution, which was dried over anhydrous magnesium sulfate, followed by concentration under reduced pressure. The concentrate was purified by means of a column chromatography (carrier: silica gel, 300 g, developing solvent: ethyl acetate-hexane, 1:1) to afford 2-(1-triphenylmethyl-3-pyrazolyl)ethanol (3.75 g) and 2-(1-triphenylmethyl-4-pyrazolyl)ethanol (1.42 g).

2-(1-triphenylmethyl-3-pyrazolyl)ethanol

IR(KBr): 3320, 3050, 3025, 2920, 2870, 1595, 1520, 1490, 1440 cm$^{-1}$. $^1$H-NMR(CDCl$_3$)δ: 2.85(2H,t,J=6 Hz), 3.82(2H,dt,J=6 Hz), 6.06(1H,d,J=2 Hz), 7.1–7.4(16H,m).

2-(1-triphenylmethyl-4-pyrazolyl)ethanol

IR(KBr): 3380, 3050, 3025, 2920, 2870, 1590, 1490, 1440 cm$^{-1}$. $^1$H-NMR(CDCl$_3$)δ: 2.69(2H,t,J=6 Hz), 3.74(2H, t,J=6 Hz), 7.1–7.4(17H,m).

REFERENCE EXAMPLE 4

(S)-1-(2-pyridyl)-2-propanol

2-Bromopyridine (1.58 g) was dissolved in diethyl ether (20 ml). To the solution was added at −60° C. n-butyllithium (1.6M hexane solution, 6.25 ml). The mixture was stirred for 5 minutes at the same temperature. To the reaction mixture were added (S)-(−)-propylene oxide (1.00 ml) and boron trifluoride diethyl etherate (1.23 ml) successively. The mixture was stirred for 20 minutes at the same temperature. To the reaction mixture was added 5% sodium hydrogencarbonate (30 ml), which was then subjected to salting out with sodium chloride, followed by extraction with ethyl acetate (20 ml) five times. The organic layer was dried over anhydrous magnesium sulfate, which was then concentrated. The concentrate was purified by means of a column chromatography (carrier: silica gel: 50 g, eluted with ethyl acetate) to give the title compound (0.33 g).

$^1$H-NMR(CDCl$_3$)δ: 1.28(3H,d,J=6.2 Hz), 2.84(1H,dd,J= 7.8,15.0 Hz), 2.92(1H,dd,J=4.0,15.0 Hz), 4.15–4.35(1H,m), 7.1–7.2(2H,m), 7.55–7.7(1H,m), 8.45–8.55(1H,m).

REFERENCE EXAMPLE 5

1-(1-Triphenylmethyl-1,2,3-triazol-4-yl)-2-propanol

Employing 4-pentyn-2-ol in place of 3-butyn-1-ol, the same reaction and purification procedure as in Reference Example 2 were conducted to afford the title compound.

$^1$H-NMR(CDCl$_3$)δ: 1.26(3H,d,J=6.2 Hz), 2.74(1H,dd,J= 8.0,15.2 Hz), 2.86(1H,dd,J=3.9,15.2 Hz), 3.23(1H,d,J=2.8 Hz), 4.05–4.3(1H,m), 7.05–7.4(16H,m).

REFERENCE EXAMPLE 6-1
2-(6-Amino-2-pyridyl)ethanol

Lithium alumnium hydride (114 mg) was dissolved in tetrahydrofuran (10 ml). To the solution was added dropwise, at 0° C., a solution of ethyl 2-(6-amino-2-pyridyl) acetate (0.54 g) in tetrahydrofuran (4 ml). The mixture was stirred for 15 minutes at the same temperature. To the reaction mixture were added water (0.12 ml) and 1N sodium hydroxide (0.36 ml), successively. Resulting insolubles were filtered off, and the filtrate was concentrated. The concentrate was purified by means of a column chromatography (carrier: silica gel, 30 g, developing solvent: ethyl acetate-acetone, 4:1) to afford the title compound (0.23 g) as an oily product.

IR(neat): 1600, 1460 cm$^{-1}$. $^1$H-NMR(CDCl$_3$)δ: 2.84(2H, t,J=5.6 Hz), 3.96(2H,t,J=5.6 Hz), 4.40(2H,br s), 6.37(1H,d, J=8.2 Hz), 6.50(1H,d,J=7.2 Hz), 7.37(1H,dd,J=7.2,8.2 Hz).

REFERENCE EXAMPLE 6-2
6-(2-Acetylthioethyl)-2-pyridylamine

Triphenyl phosphine (2.36 g) was dissolved in tetrahydrofuran (40 ml). To the solution was added, at −20° C., diethyl azodicarboxylate (1.56 g). The mixture was stirred for 5 minutes, to which was added a solution of 2-(6-amino-2-pyridyl)ethanol (0.62 g) in tetrahydrofuran (2 ml). The mixture was stirred for one minutes, to which was added thioacetic acid (0.64 ml), followed by stirring for 4 hours at 25° C. The reaction mixture was concentrated under reduced pressure. The concentrate was purified by means of a column chromatography (carrier: silica gel, 120 g, developing solvent: ethyl acetate-hexane, 2:1) to give the title compound (0.56 g), m.p.55–59° C.

IR(KBr): 3420, 3330, 3160, 1680, 1645, 1595 cm$^{-1}$. $^1$H-NMR(CDCl$_3$)δ: 2.32(3H,s), 2.86(2H,t,J=7.2 Hz), 3.24 (2H,t,J=7.2 Hz), 4.42(2H,br s), 6.35(1H,d,J=8.2 Hz), 6.53 (1H,d,J=7.0 Hz), 7.36(1H,dd,J=7.0,8.2 Hz).

REFERENCE EXAMPLE 6-3
2-(6-Amino-2-pyridyl)ethanethiol 6-(2-Acetylthioethyl)-2-pyridylamine (0.56 g) was dissolved in methanol (10 ml). To the solution was added, at 0° C., sodium methylate (a 4.9N methanol solution, 0.58 ml), and the mixture was stirred for 30 minutes. To the reaction mixture was added iN hydrochloric acid (2.85 ml), followed by concentration under reduced pressure. To the concentrate was added ethyl acetate (10 ml), which was subjected to extraction. The extract solution was dried over anhydrous magnesium sulfate, followed by concentration to leave the title compound as an oily product (0.43 g).

IR(KBr): 1620, 1460 cm$^{-1}$. $^1$H-NMR(CDCl$_3$)δ: 1.35–1.5 (1H,m), 2.85–2.95(4H,m), 4.40(2H,br s), 6.36(1H,d,J=8.0 Hz), 6.53(1H,d,J=7.2 Hz), 7.36(1H,dd,J=7.2,8.0 Hz).

REFERENCE EXAMPLE 7-1
2-(2-Amino-4-thiazolyl)ethanol

The same reaction and purification procedure as in Reference Example 6-1 was conducted, while employing ethyl 2-amino-4-thiazolyl acetate in place of ethyl 6-amino-2-pyridyl acetate, to afford the title compound.

IR(KBr): 1615, 1515 cm$^{-1}$. $^1$H-NMR(CDCl$_3$)δ: 2.76(2H, t,J=5.6 Hz), 3.86(2H,t,J=5.6 Hz), 4.92(2H,s), 6.19(1H,s).

REFERENCE EXAMPLE 7-2
4-(2-Acetylthioethyl)-2-thiazolylamine

The same reaction and purification procedure as in Reference Example 6-2 was conducted, while employing 2-(2-amino-4-thiazolyl)ethanol in place of 2-(6-amino-2-pyridyl)ethanol, to afford the title compound.

IR(KBr): 3425, 3330, 3150, 1680, 1620, 1520 cm$^{-1}$. $^1$H-NMR(CDCl$_3$)δ: 2.33(3H,s), 2.79(2H,t,J=8 Hz), 3.17 (2H,t,J=8 Hz), 5.02(2H,br s), 6.18(1H,s).

REFERENCE EXAMPLE 8
4-(2-Acetylthioethyl)pyrimidine

The same reaction and purification procedure as in Reference Example 6-2 was conducted, while employing 2-(4-pyrimidinyl)ethanol in place of 2-(6-amino-2-pyridyl) ethanol, to afford the title compound.

$^1$H-NMR(CDCl$_3$)δ: 2.34(3H,s), 3.06(2H,t,J=7.0 Hz), 3.31 (2H,t,J=7.0 Hz), 7.22(1H,dd,J=1.3,5.2 Hz), 8.64(1H,d,J=5.2 Hz), 9.16(1H,d,J=1.3 Hz).

REFERENCE EXAMPLE 9-1
1-(2-Pyridyl)-3-(2-tetrahydropyranyloxy)-2-propanol

2-Bromopyridine (9.48 g) was dissolved in diethyl ether (100 ml). To the solution was added dropwise, at −70° C., n-butyl lithium (a 1.6M hexane solution, 37.5 ml). The mixture was stirred for 5 minutes at the same temperature. To the reaction mixture was added a solution of 2-(2-tetrahydropyranyloxymethyl)oxetane (3.13 g) in diethyl ether (10 ml). To the mixture was added boron trifluoride ethyl etherate (7.6 ml), followed by stirring for 20 minutes at the same temperature. To the reaction mixture was added an aqueous solution of sodium hydrogencarbonate (60 ml), followed by extraction with ethyl acetate four times. The organic layer was dried over anhydrous sodium sulfate, which was then concentrated. The concentrate was purified by means of a column chromatography (carrier: silica gel, 200 g, developing solvent: ethyl acetate-hexane, 4:1) to give the title compound (1.19 g).

IR(neat): 2939, 1570, 1439 cm$^{-1}$. $^1$H-NMR(CDCl$_3$)δ: 1.4–2.0(6H,m), 2.7–3.1(2H,m), 3.4–4.0(4H,m), 4.2–4.3(1H, m), 7.1–7.3(2H,m), 7.55–7.7(1H,m), 8.50(1H,d,J=4.0 Hz).

REFERENCE EXAMPLE 9-2
1-(tert-Butyldimethylsilyloxy)-3-(2-pyridyl)-2-propanol The compound (1.19 g) obtained by the method of Reference Example 9-1 was dissolved in methanol (10 ml), to which was added dropwise, at 0° C., a solution of hydrogen chloride in diethyl ether (1M, 5.01 ml). The mixture was stirred for 30 minutes at the same temperature, then for further one hour at 25° C. The reaction mixture was concentrated, to which was added dichloromethane (5 ml). To the mixture were added, at 0° C., triethylamine (1.40 ml), 4-dimethylaminopyridine (30 mg) and tert-butyl dimethylsilyl chloride (755 mg), followed by stirring for 17 hours at 25° C. The reaction mixture was diluted with ethyl acetate, which was washed with water, an aqueous solution of sodium hydrogencarbonate and an aqueous saline solution, successively. The organic layer was dried over anhydrous magnesium sulfate, followed by concentration. The concentrate was purified by means of a column chromatography (carrier: silica gel, 70 g, developing solvent: ethyl acetate-hexane, 1:1) to give the title compound as a yellow oily product (677 mg).

IR(neat): 1595, 1473, 1253 cm$^{-1}$. $^1$H-NMR(CDCl$_3$)δ: 0.06(6H,s), 0.90(9H,s), 2.89(1H,dd,J=7.7,14.7 Hz), 3.02 (1H,dd,J=4.0,14.7 Hz), 3.56(1H,dd,J=5.8,9.9 Hz), 3.66(1H, dd,J=5.8,9.9 Hz), 4.0–4.2(1H,m), 7.1–7.3(2H,m), 7.62(1H, dd,J=1.9,7.7 Hz), 8.49(1H,d,J=4.6 Hz).

REFERENCE EXAMPLE 10-1
1-(2-Tetrahydropyranyloxy)-3-(2-thiazolyl)-2-propanol The same reaction and purification procedure as in Reference Example 9-1 was conducted, while employing 2-bromothiazole in place of 2-bromopyridine, to afford the title compound.

$^1$H-NMR(CDCl$_3$)δ: 1.4–1.9(6H,m), 3.2–3.3(2H,m), 3.4–4.0(4H,m), 4.2–4.3(1H,m), 4.5–4.6(1H,m), 7.23(1H,d, J=3.3 Hz), 7.70(1H,d,J=3.3 Hz).

REFERENCE EXAMPLE 10-2
1-(tert-Butyldimethylsilyloxy)-3-(2-thiazolyl)-2-propanol The compound produced by the method of Reference Example 10-1 was subjected to the same reaction and purification procedure as in Reference Example 9-2 to afford the title compound as an oily product.

$^1$H-NMR(CDCl$_3$)δ: 0.07(6H,s), 0.90(9H,s), 3.13(1H,dd, J=7.6,15.4 Hz), 3.26(1H,dd,J=4.4,15.4 Hz), 3.52(1H,d,J=4.4 Hz), 3.64(2H,d,J=5.8 Hz), 4.0–4.1(1H,m), 7.22(1H,d,J=3.7 Hz), 7.70(1H,d,J=3.7 Hz).

REFERENCE EXAMPLE 11-1
(S)-1-Methoxy-3-[1-[2-(trimethylsilyl)ethoxymethyl]pyrazol-5-yl]-2-propanol 1-[2-trimethylsilyl)ethoxymethyl]pyrazole (1.98 g) was dissolved in ethyl ether (20 ml). To the solution was added, at −60° C., n-butyl lithium (a 1.6M hexane solution, 6.88 ml). The mixture was stirred for one hour at the same temperature, to which was then added (S)-methyl glycidyl ether (1.76 g). The mixture was stirred for 3 hours while warming up to 25° C. The reaction mixture was shaken together with a 5% aqueous solution of sodium hydrogencarbonate (30 ml). The aqueous layer was subjected to extraction with ethyl ether (30 ml). Organic layers were combined and dried over anhydrous magnesium sulfate, which was then concentrated. The concentrate was purified by means of a column chromatography (carrier: silica gel, 100 g, developing solvent: ethyl acetate-hexane, 3:2) to afford the title compound (0.51 g) as an oily product.

IR(neat): 1245, 1080 cm$^{-1}$. $^1$H-NMR(CDCl$_3$)δ: −0.03 (9H,s), 0.8–0.95(2H,m), 2.89(1H,dd,J=7.2,15.4 Hz), 2.99 (1H,dd,J=5.2,15.4 Hz), 3.35(1H,dd,J=6.4,9.4 Hz), 3.40(3H, s), 3.43(1H,dd,J=4.2,9.4 Hz), 3.5–3.65(2H,m), 3.95–4.15 (1H,m), 5.48(2H,s), 6.20(1H,d,J=1.8 Hz),7.46(1H,d,J=1.8 Hz).

REFERENCE EXAMPLE 11-2
(S)-1-Methoxy-3-(3-pyrazolyl)-2-propanol

The compound (0.51 g) produced in Reference Example 11-1 was dissolved in ethanol (12 ml). To the solution was added 10% hydrochloric acid (24 ml). The mixture was stirred for 2 hours under reflux. The reaction mixture was left standing for cooling, followed by concentration. To the concentrate was added a 5% aqueous solution of sodium hydrogencarbonate (6 ml). The mixture was subjected to extraction three times with ethyl acetate-THF (1:1, 20 ml). Organic layers were combined and dried over anhydrous magnesium sulfate, which was then concentrated to afford the title compound (0.28 g) as an oily product.

IR(neat): 1525, 1470, 1450 cm$^{-1}$. $^1$H-NMR(CDCl$_3$)δ: 2.81(1H,dd,J=7.2,15.0 Hz), 2.91(1H,dd,J=5.0,15.0 Hz), 3.34(1H,dd,J=7.0,9.6 Hz), 3.39(3H,s), 3.43(1H,dd,J=4.0,9.6 Hz), 4.0–4.15(1H,m), 6.12(1H,d,J=1.8 Hz), 7.49(1H,d,J=1.8 Hz).

REFERENCE EXAMPLE 11-3
(R)-3-(2-Acetylthio-1-methoxypropyl)pyrazole

The same reaction and purification as in Reference Example 6–2 were conducted, employing (S)-1-methoxy-3-(3-pyrazolyl)-2-propanol (470 mg) in place of 2-(6-amino-2-pyridyl)ethanol, to afford the title compound (268 mg).

IR(neat): 1730, 1690 cm$^{-1}$. $^1$H-NMR(CDCl$_3$)δ: 2.32(3H, s), 3.01(1H,dd,J=6.6,14.6 Hz), 3.13(1H,dd,J=6.6,14.6 Hz), 3.38(3H,s), 3.42(1H,dd,J=7.2,9.8 Hz), 3.50(1H,dd,J=4.8,9.8 Hz), 3.9–4.1(1H,m), 6.17(1H,d,dJ=1.8 Hz), 7.51(1H,d,J=1.8 Hz).

REFERENCE EXAMPLE 11-4
(R)-1-Methoxy-3-(3-pyrazolyl)-2-propanethiol

The same reaction and purification as in Reference Example 6-3 were conducted, employing (R)-3-(2-acetylthio-1-methoxypropyl)pyrazole (173 mg) in place of 6-(2-acetylthioethyl)-2-aminopyridine, to afford the title compound (129 mg).

$^1$H-NMR(CDCl$_3$)δ: 2.97(1H,dd,J=7.2,14.8 Hz), 3.14(1H, dd,J=15.0,14.8 Hz), 3.2–3.4(1H,m), 3.38(1H,dd,J=3.2,9.4 Hz), 3.40(3H,s), 3.47(1H,dd,J=6.2,9.4 Hz), 6.20(1H,d,J=2.0 Hz), 7.55(1H,d,J=2.0 Hz).

REFERENCE EXAMPLE 12-1
Ethyl (1-triphenylmethyl-1H-1,2,4-triazol-3-yl)acetate Ethyl (1H-1,2,4-triazol-3-yl)acetate (2.83 g) was dissolved in DMF (40 ml). To the solution were added triphenyl methyl chloride (5.08 g) and triethylamine (2.55 ml). The mixture was stirred for 3 hours at 25° C. The reaction mixture was added to ice-water (150 ml), which was subjected to extraction with ethyl ether (100 ml). The organic layer was washed twice with water (150 ml), which was dried over anhydrous magnesium sulfate, followed by concentration under reduced pressure. The concentrate was purified by means of a column chromatography (carrier: silica gel, 150 g, developing solvent: ethyl acetate-hexane, 1:1) to afford the title compound (2.56 g) as a crystalline product, m.p.117–119° C.

IR(KBr): 1745, 1505 cm$^{-1}$. $^1$H-NMR(CDCl$_3$)δ: 1.25(3H, t,J=7.1 Hz), 3.84(2H,s), 4.18(2H,q,J=7.1 Hz), 7.1–7.25(6H, m), 7.25–7.4(9H,m), 7.92(1H,s).

REFERENCE EXAMPLE 12-2
2-(1-Triphenylmethyl-1H-1,2,4-triazol-3-yl)ethanol

The same reaction and purification as in Reference Example 6-1 were conducted, employing ethyl (1-triphenylmethyl-1H-1,2,4-triazol-3-yl)acetate (1.28 g) in place of ethyl 2-(6-amino-2-pyridyl)acetate, to afford the title compound (0.50 g) as a crystalline product, m.p.127–129° C.

IR(KBr): 1510, 1485, 1445 cm$^{-1}$. $^1$H-NMR(CDCl$_3$)δ: 3.01(2H,t,J=5.6 Hz), 3.95(2H,t,J=5.6 Hz), 7.05–7.2(6H,m), 7.25–7.4(9H,m), 7.91(1H,s).

REFERENCE EXAMPLE 12-3
3-(2-Acetylthioethyl)-1-triphenylmethyl-1H-1,2,4-triazole The same reaction and purification as in Reference Example 6-2 were conducted, employing 2-(1-triphenylmethyl-1,2,4-triazol-3-yl)ethanol (0.96 g) in place of 2-(6-amino-2-pyridyl)ethanol, to afford the title compound (0.60 g) as a crystalline product, m.p.135–140° C.

IR(KBr): 1745, 1250 cm$^{-1}$. $^1$H-NMR(CDCl$_3$)δ: 2.30(3H, s), 3.0–3.1(2H,m), 3.25–3.35(2H,m), 7.05–7.2(6H,m), 7.25–7.4(9H,m), 7.86(1H,s).

REFERENCE EXAMPLE 12-4
3-(2-Acetylthioethyl)-1H-1,2,4-triazole 3-(2-Acetylthioethyl)-1-triphenylmethyl-1,2,4-triazole (0.50) was dissolved in THF (2.5 ml). To the solution were added 10% hydrochloric acid (0.5 ml) and methanol (10 ml). The mixture was stirred for 1.5 hour at 25° C. The reaction mixture was concentrated, to which was added NaHCO$_3$, to make the solution to be weakly basic, followed by extraction three times with THF-ethyl acetate (1:1, 10 ml). Organic layers were combined and dried over anhydrous magnesium sulfate, followed by concentration. The concentrate was purified by means of a column chromatography (carrier: silica gel, 20 g, developing solvent: acetone) to afford the title compound (134 mg) as a crystalline product, m.p.84–86° C.

IR(KBr): 1680, 1485 cm$^{-1}$. $^1$H-NMR(CDCl$_3$)δ: 2.36(3H, s), 3.05–3.2(2H,m), 3.25–3.35(2H,m), 8.07(1H,s).

REFERENCE EXAMPLE 13
3-(2-Acetylthioethyl)pyridazine 2-(3-Pyridazyl)ethanol (870 mg) was subjected to the same reaction and purification as in Reference Example 6-2 to afford the title compound (1021 mg).

IR(KBr): 1690 cm$^{-1}$. $^1$H-NMR(CDCl$_3$)δ: 2.34(3H,s), 3.2–3.45(4H,m), 7.4–7.6(2H,m), 9.12(1H,dd,J=2.2,4.2 Hz).

REFERENCE EXAMPLE 14-1
1-(3-Pyridazinyl)-2-propanol

Diisopropylamine (8.52 ml) was dissolved in tetrahydrofuran (100 ml). To the solution was added dropwise, at 0° C., n-butyl lithium (a 1.64M hexane solution, 36.6 ml). The mixture was stirred for 30 minutes at the same temperature. The reaction mixture was cooled to −70° C., to which was added dropwise a solution of 3-methyl pyridazine (4.71 g) in tetrahydrofuran (10 ml). The mixture was stirred for 30 minutes at the same temperature, to which then added acetaldehyde (2.45 g). The mixture was wormed up to room temperature over 30 minutes, which was stirred for 6 hours at the same temperature. To the reaction mixture was added a saturated aqueous solution of ammonium chloride (10 ml). The mixture was concentrated under reduced pressure. The concentrate was purified by means of a silica gel chromatography (developing solvent: ethyl acetate-methanol 1:0→9:1) to afford the title compound (1.29 g).

$^1$H-NMR(CDCl$_3$)δ: 1.35(3H,d,J=6.2 Hz), 3.05–3.15(2H, m), 4.3–4.5(1H,m), 7.39(1H,dd,J=1.9,8.4 Hz), 7.47(1H,dd, J=4.8,8.4 Hz), 9.10(1H,dd,J=1.9,4.8 Hz).

REFERENCE EXAMPLE 14-2
3-[2-(4-Toluenesulfonyloxy)propyl]pyridazine 1-(3-Pyridazinyl)-2-propanol (1.40 g) was dissolved in dichloromethane (10 ml). To the solution were added, at 0° C., pyridine (1.63 ml) and 4-toluenesulfonyl chloride (2.89 g), successively. The mixture was stirred for 19 hours at the same temperature, to which was added water (10 ml). The mixture was stirred for 2 hours, to which was added ethyl acetate (80 ml). The organic layer was separated and washed with a saturated aqueous saline solution and dried over anhydrous sodium sulfate, followed by concentration under reduced pressure. The concentrate was purified by means of a silica gel column chromatography (developing solvent: ethyl acetate) to afford the title compound (1.65 g).

$^1$H-NMR(CDCl$_3$)δ: 1.39(3H,d,J=6.2 Hz), 2.43(3H,s), 3.22(1H,dd,J=7.2,14.2 Hz), 3.33(1H,dd,J=5.0,14.2 Hz), 4.95–5.15(1H,m), 7.25(2H,d,J=8.2 Hz), 7.39(2H,d,J=3.0 Hz), 7.62(2H,d,J=8.2 Hz), 9.05(1H,t,J=3.0 Hz).

REFERENCE EXAMPLE 14-3
3-(2-Acetylthiopropyl)pyridazine

3-[2-(4-Toluenesulfonyloxy)propyl]pyridazine (2.53 g) was dissolved in acetone (50 ml). To the solution was added potassium thioacetate (1.48 g), and the mixture was stirred for 4.5 hours under reflux. The reaction mixture was concentrated under reduced pressure. To the concentrate was added water (30 ml), which was subjected to extraction with ethyl acetate. The extract solution was dried over anhydrous magnesium sulfate, which was concentrated under reduced pressure. The concentrate was purified by a silica gel column chromatography (developing solvent: ethyl acetate-hexane 4:1→1:0) to afford the title compound (1.18 g).

IR(KBr): 1688 cm$^{-1}$. $^1$H-NMR(CDCl$_3$)δ: 1.38(3H,d,J=7.0 Hz), 2.29(3H,s), 3.30(2H,d,J=7.6 Hz), 3.8–4.1(1H,m), 7.4–7.6(2H,m), 9.05–9.2(1H,m).

REFERENCE EXAMPLE 15-1
2-(2-Acetylthioethyl)imidazo[1,2-a]pyridine

The same reaction and purification as in Reference Example 6-2 were conducted, employing 2-(imidazo[1,2-a] pyridin-2-yl)ethanol (713 mg) in place of 2-(6-amino-2-pyridyl)ethanol, to afford the title compound (1.10 g).

$^1$H-NMR(CDCl$_3$)δ: 2.34(3H,s), 3.07(2H,t,J=7.2 Hz), 3.31 (2H,t,J=7.2 Hz), 6.7–6.8(1H,m), 7.1–7.2(1H,m), 7.41(1H,s), 7.45–7.6(1H,m), 8.0–8.1(1H,m).

REFERENCE EXAMPLE 15-2
2-(Imidazo[1,2-a]pyridin-2-yl)ethanethiol

The same reaction and purification as in Reference Example 6-3 were conducted, employing 2-(2-acetylthioethyl)imidazo[1,2-a]pyridine (870 mg) in place of 6-(2-acetylthioethyl)-2-pyridylamine, to afford the title compound (0.78 g).

$^1$H-NMR(CDCl$_3$)δ: 1.50(1H,t,J=7.8 Hz), 2.9–3.2(4H,m), 6.7–6.8 (1H,m), 7.1–7.2(1H,m), 7.44(1H,s), 7.45–7.6(1H, m), 8.0–8.1(1H,m).

REFERENCE EXAMPLE 16-1
N-(2-pyrazinylmethyl)-3-chloropropionamide

To an aqueous solution of sodium hydroxide (2.31 g) in water (30 ml) was added 2-aminomethylpyrazine hydrochloride (7.0 g) under ice cooling, to which 3-chloropropionylchloride (5.05 g) and solution of sodium hydroxide (2.31 g) in water (30 ml) were simultaneously added dropwise over 30 minutes under stirring. The mixture was stirred for 1 hour at room temperature, followed by extraction with ethyl acetate-THF (1:1, 100 ml×2). The aqueous layer was subjected to salting out with sodium chloride, followed by extraction with ethyl acetate-THF (1:1, 100 ml×2). The organic layers were combined and dried over magnesium sulfate, followed by concentration under reduced pressure. The concentrate was subjected to column chromatography [carrier: silica gel, 200 g; developing agent: ethyl acetate→ethyl acetate-ethanol (4:1)]. The eluent was concentrated and the resulting solid was washed with hexane to give the title compound (4.50 g) as colorless solid product.

IR(KBr): 3287, 1661, 1549, 1406 cm$^{-1}$. $^1$H-NMR (CDCl$_3$) δ: 2.75(2H,t,J=6.4 Hz), 3.85(2H,t,J=6.4 Hz), 4.66 (2H,d,J=5.4 Hz), 7.60–7.85(1H,m), 8.52(2H,s), 8.64(1H,s).

REFERENCE EXAMPLE 16-2
3-(2-Chloroethyl)imidazo[1,5-a]pyrazine

To a solution of N-(2-pyrazinylmethyl)-3-chloropropionamide (4.52 g) in dichloromethane (30 ml) was added phosphorus oxychloride (1.29 g) under ice cooling. The mixture was stirred for 3 days at room temperature. The mixture was concentrated, and the residue was poured into ice water (400 ml), followed by neutralization with sodium carbonate. The reaction mixture was subjected to salting out with sodium chloride, and extracted with ethyl acetate-THF (1:1, 150 ml×3). The organic layers were combined and dried over magnesium sulfate. The solvent was distilled off under reduced pressure. The residue was subjected to flash column chromatography [carrier: silica gel, 100 g, developing solvent: ethyl acetate→ethyl acetate-ethanol (9:1)]. The eluate was concentrated and residual solid was washed with diethylether to give the title compound (3.07 g) as colorless solid product.

IR(KBr): 3400, 1615, 1354, 910 cm$^{-1}$. $^1$H-NMR(CDCl$_3$) δ: 3.48(2H,t,J=6.8 Hz), 4.03(2H,t,J=6.8 Hz), 7.56(1H,d,J= 5.0 Hz), 7.70–7.80(1H,m), 7.79(1H,s), 8.95(1H,d,J=1.6 Hz).

REFERENCE EXAMPLE 16-3
3-(2-Acetylthioethyl)imidazo[1,5-a]pyrazine

To a solution of 3-(2-chloroethyl)imidazo[1,5-a]pyrazine (1.51 g) in DMF (10 ml) was added potassium thioacetate (1.23 g). The mixture was stirred for 4 hours at room temperature. To the reaction mixture was added water. The mixture was subjected to extraction with ethyl acetate (50 ml×4). The organic layer was dried over anhydrous magnesium sulfate. The solvent was distilled off under reduced pressure. The residue was subjected to column chromatography (carrier: silica gel, 60 g, developing solvent: ethyl acetate) to give the title compound (1.65 g) as colorless solid product.

IR(KBr): 3400, 1686, 1615, 1354, 1136, 910 cm$^{-1}$.
$^1$H-NMR(CDCl$_3$) δ: 2.37(3H,s), 3.30(4H,s), 7.57(1H,d,J=5.2 Hz), 7.75(1H,s), 7.87(1H,dd,J=5.2,2.0 Hz), 8.93(1H,d, J=2.0 Hz).

REFERENCE EXAMPLE 17-1
2-Cyano-N-(2-pyridylmethyl)acetamide

Cyanoacetic acid (8.51 g) was dissolved in dichloromethane (400 ml). To the solution was added 2-aminomethylpyridine (10.81 g). The mixture was stirred for a while, to which was then added 1-ethyl-3-(3-dimethylaminopropyl)carbodiimide hydrochloride (19.17 g). The mixture was stirred for 15 minutes at 25° C. To the reaction mixture was added a saturated aqueous solution of sodium hydrogencarbonate (200 ml). The mixture was shaken and left standing. The aqueous layer was subjected to extraction with ethyl acetate (200 ml) three times. The organic layers were combined and dried over anhydrous magnesium sulfate, followed by concentration to afford the title compound (15.51 g).

$^1$H-NMR(CDCl$_3$)δ: 3.47(2H,s), 4.60(2H,d,J=4.6 Hz), 7.2–7.3(2H,m), 7.5–7.8(2H,m), 8.5–8.6(1H,m).

REFERENCE EXAMPLE 17-2
2-(Imidazo[1,5-a]pyridin-3-yl)acetonitrile

2-Cyano-N-(2-pyridylmethyl)acetamide (15.51 g) was dissolved in chloroform (80 ml). To the solution was added phosphorus oxychloride (40 ml), which was refluxed for 4 hours. The reaction mixture was added to ice-water in limited amounts, to which was added a 25% aqueous ammonia (140 ml) to neutralize, which was then shaken. The aqueous layer was subjected to extraction with ethyl acetate (150 ml) twice. The organic layers were combined and dried over anhydrous magnesium sulfate, followed by concentration. The concentrate was purified by means of a column chromatography (carrier: silica gel, 250 g, developing solvent: ethyl acetate) to afford the title compound (5.00 g).

$^1$H-NMR(CDCl$_3$)δ: 4.21(2H,s), 6.7–6.9(2H,m), 7.45(1H, s), 7.45–7.55(1H,m), 7.8–7.9(1H,m).

REFERENCE EXAMPLE 17-3
Methyl 2-(imidazo[1,5-a]pyridin-3-yl)acetate 2-(Imidazo[1,5-a]pyridin-3-yl)acetonitrile (4.65 g) was dissolved in acetic acid (26 ml). To the solution was added 50%(v/v) sulfuric acid (52 ml), and the mixture was stirred for 3 hours at 100° C., followed by distilling off acetic acid under reduced pressure. To the residue was added, in limited amounts, sodium hydrogencarbonate, and the mixture was concentrated to dryness. To the residue was added methanol (200 ml), then insolubles were filtered off. To the filtrate was added a 4N HCl ethyl acetate solution (40 ml). The mixture was stirred for 15 hours at 25° C., followed by concentration under reduced pressure. To the concentrate were added a 5% aqueous solution of sodium hydrogencarbonate (100 ml) and ethyl acetate (200 ml). The mixture was shaken and left standing to form two layers. The organic layer was dried over anhydrous magnesium sulfate and, then, concentrated to afford the title compound (1.85 g).

$^1$H-NMR(CDCl$_3$)δ: 3.72(3H,s), 4.14(2H,s), 6.55–6.8(2H, m), 7.41(1H,s), 7.4–7.5(1H,m), 7.75–7.9(1H,m).

REFERENCE EXAMPLE 17-4
2-(Imidazo[1,5-a]pyridin-3-yl)ethanol

Methyl 2-(imidazo[1,5-a]pyridin-3-yl)acetate (1.85 g) was dissolved in methanol (30 ml). To the solution was added sodium borohydride (3.68 g), and the mixture was stirred for one hour at 60° C. To the reaction mixture was added water (20 ml), which was concentrated under reduced pressure. The concentrate was subjected to extraction twice with ethyl acetate (40 ml). The organic layers were combined and dried over anhydrous magnesium sulfate, followed by concentration to afford the title compound (1.39 g).

$^1$H-NMR(CDCl$_3$+DMSO-d$_6$)δ: 3.15(2H,t,J=5.8 Hz), 4.15 (2H,t,J=5.8 Hz), 6.5–6.8(2H,m), 7.33(1H,s), 7.35–7.5(1H, m), 7.75–7.85(1H,m).

REFERENCE EXAMPLE 17-5
3-(2-Acetylthioethyl)imidazo[1,5-a]pyridine

The same reaction and purification as in Reference Example 6-2 were conducted, employing 2-(imidazo[1,5-a]pyridin-3-yl)ethanol (1.19 g) in place of 2-(6-amino-2-pyridyl)ethanol, to afford the title compound (0.60 g).

$^1$H-NMR(CDCl$_3$)δ: 2.37(3H,s), 3.2–3.4(4H,m), 6.55–6.75(2H,m), 7.37(1H,s), 7.35–7.5(1H,m), 7.9–8.0(1H, m).

REFERENCE EXAMPLE 17-6
2-(Imidazo[1,5-a]pyridin-3-yl)ethanethiol

The same reaction and purification as in Reference Example 6-3 were conducted, employing 3-(2-acetylthioethyl)imidazo[1,5-a]pyridine (0.60 g) in place of 6-(2-acetylthioethyl)-2-aminopyridine, to afford the title compound (0.46 g).

$^1$H-NMR(CDCl$_3$)δ: 1.72(1H,t,J=8.0 Hz), 3.0–3.45(4H, m), 6.5–6.75(2H,m), 7.39(1H,s), 7.3–7.5(1H,m), 7.7–7.85 (1H,m).

REFERENCE EXAMPLE 18-1
2-(Imidazo[1,2-b]pyridazin-2-yl)ethanol

To a solution of ethyl imidazo[1,2-b]pyridazin-2-yl acetate (3.10 g, synthesized by the method disclosed in IL FARMACO, 50, 349 (1995)) in methanol (60 ml) was added, at 0° C., sodium borohydride (5.50 g). The reaction mixture was heated for 15 minutes under reflux, which was then cooled to 0° C., followed by addition of water (50 ml). The mixture was stirred for 10 minutes at room temperature. The reaction mixture was concentrated, which was subjected to extraction three times with ethyl acetate-tetrahydrofuran (1:1). The organic layers were combined, dried over anhydrous magnesium sulfate and then concentrated to give white crystals. The crystalline product was washed with ethyl acetate, then, with diisopropyl ether to afford the title compound (1.66 g).

IR(KBr): 3189, 1348, 1061, 804 cm$^{-1}$. $^1$H-NMR(CDCl$_3$) δ: 3.06(2H,t,J=5.6 Hz), 4.04(2H,t,J=5.6 Hz), 7.02(1H,dd,J= 9.2,4.4 Hz), 7.83(1H,s), 7.87(1H,dd,J=9.2,1.4 Hz), 8.27(1H, dd,J=4.4,1.4 Hz).

REFERENCE EXAMPLE 18-2
2-(2-Acetylthioethyl)imidazo[1,2-b]pyridazine

The compound produced in REFERENCE EXAMPLE 18-1 (1.58 g) and triethylamine (1.61 ml) were dissolved in dimethylformamide (20 ml). To the solution was added, at 0°

C., methanesulfonyl chloride (0.90 ml). The reaction mixture was stirred for 30 minutes at the same temperature, which was then poured into a saturated aqueous solution of sodium hydrogencarbonate. The mixture was subjected to extraction three times with ethyl acetate. The organic layers were combined, dried over anhydrous magnesium sulfate and, then, concentrated. The concentrate was dissolved in dimethylformamide (50 ml), to which was added, at 0° C., potassium thioacetate (1.20 g). The reaction mixture was stirred for 6 hours at room temperature, which was stirred for 6 hours at room temperature, followed by concentration. The concentrate was poured into water, which was subjected to extraction three times with ethyl acetate. The organic layers were combined, washed twice with a saturated aqueous saline solution and dried over anhydrous magnesium sulfate, followed by concentration to afford the title compound (1.54 g) as a pale brown crystalline product.

IR(KBr): 1688, 1530, 1337, 1138, 799 cm$^{-1}$. $^1$H-NMR (CDCl$_3$)δ: 2.34(3H,s), 3.12(2H,d,J=7.0 Hz), 3.33(2H,d,J= 7.0 Hz), 7.00(1H,dd,J=9.2,4.4 Hz), 7.82(1H,s), 7.87(1H,dd, J=9.2,1.8 Hz), 8.26(1H,dd,J=4.4,1.8 Hz).

REFERENCE EXAMPLE 19-1
Ethyl imidazo[2,1-b][1,3,4]thiadiazol-6-yl acetate

A mixture solution of 2-amino-1,3,4-thiadiazole (15.17 g), ethyl 4-chloroacetoacetate (25.15 g) and ethanol (200 ml) was heated for 24 hours under reflux. The solvent was distilled off, and the residue was dissolved in water, which was neutralized with a saturated aqueous solution of sodium hydrogencarbonate, followed by extraction with ethyl acetate. The organic layer was washed with water, then, with a saturated aqueous saline solution, which was dried over anhydrous magnesium sulfate, followed by concentration. The concentrate was purified by means of a column chromatography (carrier: silica gel, developing solvent: ethyl acetate-hexane, 1:1) to afford the title compound (8.55 g) as an oily product.

IR(KBr): 1732, 1030, 864 cm$^{-1}$. $^1$H-NMR(CDCl$_3$)δ: 1.29 (3H,t,J=7.0 Hz), 3.77(2H,s), 4.21(2H,q,J=7.0 Hz), 7.80(1H, s), 8.50(1H,s).

REFERENCE EXAMPLE 19-2
2-(Imidazo[2,1-b][1,3,4]thiadiazol-6-yl)ethanol

To a solution of the compound (3.00 g) produced in Reference Example 19-1 in methanol (50 ml) was added, at 0° C., sodium borohydride (4.00 g). The reaction mixture was heated for 15 minutes under reflux, which was then cooled, followed by addition of a 10% aqueous solution of citric acid. The mixture was concentrated, which was subjected to extraction with ethyl acetate-tetrahydrofuran (2:1) three times. The organic layers were combined, which was dried over anhydrous magnesium sulfate, followed by concentration. To the concentrate was added ethyl acetate, and insolubles were filtered off. The filtrate was concentrated, which was purified by means of a column chromatography (carrier: silica gel, developing solvent: ethyl acetate) to afford the title compound (0.74 g) as a white crystalline product.

IR(KBr): 3252, 1462, 1049 cm$^{-1}$. $^1$H-NMR(CDCl$_3$)δ: 2.93(2H,t,J=5.8 Hz), 3.97(2H,t,J=5.8 Hz), 7.65(1H,s), 8.50 (1H,s).

REFERENCE EXAMPLE 19-3
6-(2-Acetylthioethyl)imidazo[2,1-b][1,3,4]thiadiazole The compound (0.74 g) produced in Reference Example 19-2 and triethylamine (1.03 ml) were dissolved dimethylformamide (10 ml). To the solution was added, at 0° C., methanesulfonyl chloride (0.58 ml). The reaction mixture was stirred for 30 minutes at the same temperature, which was poured into a saturated aqueous solution of sodium hydrogencarbonate, followed by extraction three times with ethyl acetate. The organic layers were combined and dried over anhydrous magnesium sulfate, followed by concentration. The concentrate was dissolved in dimethylformamide (50 ml), to which was added, at 0° C., potassium thioacetate (1.00 g). The reaction was stirred for 16 hours at room temperature, which was concentrated. The concentrate was poured into water, which was subjected to extraction with ethyl acetate. The organic layer was washed with water and a saturated aqueous saline solution, which was dried over magnesium sulfate, followed by concentration. The concentrate was purified by means of a column chromatography (carrier: silica gel, developing solvent: ethyl acetate-hexane, 2:1) to afford the title compound (0.56 g) as a colorless crystalline product.

IR(KBr): 1686, 1489, 1460, 1134, 862 cm$^{-1}$. $^1$H-NMR (CDCl$_3$)δ: 2.34(3H,s), 2.98(2H,t,J=7.1 Hz), 3.26(2H,t,J=7.1 Hz), 7.64(1H,s), 8.49(1H,s).

REFERENCE EXAMPLE 20-1
Ethyl 5-aminoimidazo[1,2-a]pyridin-2-yl acetate

A mixture of 2,6-diaminopyridine (16.37 g), ethyl 4-chloroacetoacetate (24.70 g) and 1,2-dimethoxyethane (250 ml) was stirred for 3 hours at room temperature, which was heated for 18 hours under reflux. The reaction mixture was cooled, and, then, the supernatant was removed. The residue was dissolved in water, which was neutralized with a saturated aqueous solution of sodium hydrogencarbonate, followed by extraction with ethyl acetate. The organic layer was washed with a saturated aqueous saline solution, dried over anhydrous magnesium sulfate and, then, concentrated. The resulting pale green crystalline product was washed with ethyl acetate and, then, with diisopropyl ether to afford the title compound (8.58 g).

IR(KBr): 3372, 3140, 1725, 1545, 1508, 1188, 733 cm$^{-1}$. $^1$H-NMR(CDCl$_3$)δ: 1.29(3H,t,J=7.2 Hz), 3.89(2H,s), 4.22 (2H,q,J=7.2 Hz), 4.26(2H,brs), 6.05(1H,t,J=4.4 Hz), 7.01 (2H,d,J=4.4 Hz), 7.39(1H,s).

REFERENCE EXAMPLE 20-2
2-(5-Aminoimidazo[1,2-a]pyridin-2-yl)ethanol

To a solution of the compound (2.19 g) produced in Reference Example 20-1 in tetrahydrofuran (100 ml) was added, in limited amounts, at −15° C., lithium aluminium hydride (455 mg). The mixture was stirred for 0.5 hour at the same temperature. To the reaction mixture was added, in small amounts, water (2 ml). Insolubles were filtered off, and the filtrate was concentrated to afford the title compound (1.86 g) as a brown solid product.

IR(KBr): 3445, 3310, 3185, 1647, 1516, 1339, 1051, 770, 737 cm$^{-1}$. $^1$H-NMR(CDCl$_3$+DMSO-d$_6$)δ: 2.98(2H,t,J=6.4 Hz), 3.92(2H,t,J=6.4 Hz), 4.63(1H,br), 5.73(2H,br), 6.01 (1H,d,J=7.2 Hz), 6.87(1H,d,J=8.8 Hz), 7.06(1H,dd,J=8.8, 7.2 Hz), 7.51(1H,s).

REFERENCE EXAMPLE 20-3
2-(2-Acetylthioethyl)-5-aminoimidazo[1,2-a]pyridine

To a solution of triphenylphosphine (3.41 g) in tetrahydrofuran (30 ml) was added dropwise, at −15° C., diisopropyl azodicarboxylate (2.56 ml). The mixture was then stirred for 10 minutes at the same temperature. To the reaction mixture were added a solution of the compound (1.86 g) produced in Reference Example 20-2 in tetrahydrofuran (20 ml) and thioacetic acid (0.93 ml). The mixture was stirred for 1 hour at temperatures ranging from −15° C. to 0° C. The reaction mixture was concentrated, which was diluted with ethyl acetate and washed with water, a saturated aqueous solution of sodium hydrogencarbonate and, then a saturated aqueous saline solution, followed by drying over anhydrous magnesium sulfate and concentration. The concentrate was purified by means of a column chromatography (carrier: silica gel, developing solvent: ethyl acetate) to afford the title compound (1.39 g).

IR(KBr): 3333, 3150, 1684, 1541, 1510, 1121 cm$^{-1}$. $^1$H-NMR(CDCl$_3$)δ: 2.33(3H,s), 3.08(2H,t,J=6.8 Hz), 3.31 (2H,t,J=6.8 Hz), 4.34(2H,br), 6.06(1H,t,J=4.2 Hz), 7.10(2H, d,J=4.2 Hz), 7.20(1H,s).

REFERENCE EXAMPLE 21
5-(2-Acetylthioethyl)imidazo[1,2-a]pyridine

To a solution of triphenyl phosphine (4.20 g) in tetrahydrofuran (30 ml) was added dropwise, at −15° C., diisopropyl azodicarboxylate (3.16 ml). The mixture was stirred for 10 minutes at the same temperature. To the reaction mixture were, then, added a solution of 2-(imidazo[1,2-a]pyridin-5-yl)ethanol (1.00 g) in dimethylformamide (20 ml) and thioacetic acid (1.14 ml). The reaction mixture was stirred for 0.5 hour at −15° C. and, then, for 20 hours at room temperature. The reaction mixture was concentrated, which was diluted with ethyl acetate and washed with water, a saturated aqueous solution of sodium hydrogencarbonate and, then, with a saturated aqueous saline solution, followed by drying over anhydrous magnesium sulfate and concentration. The concentrate was purified by means of a column chromatography (carrier: silica gel, developing solvent: ethyl acetate-hexane, 1:1) to afford the title compound (0.52 g).

IR(KBr): 1686, 1437, 1184, 1119 cm$^{-1}$. $^1$H-NMR(CDCl$_3$) δ: 2.40(3H,s), 3.12–3.30(4H,m), 6.65(1H,d,J=7.0 Hz), 7.16 (1H,dd,J=9.0,7.0 Hz), 7.41–7.72(3H,m), 7.86(1H,s).

REFERENCE EXAMPLE 22-1
Ethyl imidazo[1,2-a]pyrazin-2-yl acetate

A mixture of 2-aminopyrazine (5.00 g), ethyl 4-chloroacetoacetate (9.05 g) and ethanol (50 ml) was heated for 44 hours under reflux. The solvent was distilled off, and the residue was dissolved in water, which was neutralized with a saturated aqueous solution of sodium hydrogencarbonate, followed by extraction three times with ethyl acetate-tetrahydrofuran (1:1). The organic layers were combined, which was washed with water and, then, with a saturated aqueous saline solution, followed by drying over anhydrous magnesium sulfate and, then, concentration. The concentrate was purified by means of a column chromatography (carrier: silica gel, developing solvent: ethyl acetate) to afford the title compound (2.03 g).

IR(KBr): 1732, 1534, 1493, 1291, 1203, 1167, 1034 cm$^{-1}$. $^1$H-NMR(CDCl$_3$)δ: 1.30(3H,t,J=7.0 Hz), 3.94(2H,s), 4.23 (2H,q,J=7.0 Hz), 7.74(1H,s), 7.87(1H,d,J=4.6 Hz), 8.03(1H, dd,J=4.6,1.6 Hz), 9.04(1H,d,J=1.6 Hz).

REFERENCE EXAMPLE 22-2
2-(Imidazo[1,2-a]pyrazin-2-yl)ethanol

The same reaction and purification as in Reference Example 18-1 were conducted, employing the compound produced in Reference Example 22-1, to afford the title compound.

$^1$H-NMR(CDCl$_3$+DMSO-d$_6$)δ: 3.07(2H,t,J=6.0 Hz), 3.98 (2H,t,J=6.0 Hz), 7.68(1H,s), 7.83(1H,d,J=4.4 Hz), 8.14(1H, dd,J=4.4,1.4 Hz), 8.96(1H,d,J=1.4 Hz).

REFERENCE EXAMPLE 22-3
2-(2-Acetylthioethyl)imidazo[1,2-a]pyrazine

The same reaction and purification as in Reference Example 21 were conducted, employing the compound produced in Reference Example 22-2, to afford the title compound.

IR(KBr): 1684, 1491, 1358, 1136, 835, 629 cm$^{-1}$. $^1$H-NMR(CDCl$_3$)δ: 2.34(3H,s), 3.14(2H,t,J=6.6 Hz), 3.32 (2H,t,J=6.6 Hz), 7.54(1H,s), 7.86(1H,d,J=4.8 Hz), 8.01(1H, dd,J=4.8,1.4 Hz), 9.02(1H,d,J=1.4 Hz).

REFERENCE EXAMPLE 23-1
Ethyl imidazo[1,2-a]pyridin-3-yl acetate

A mixture of (imidazo[1,2-a]pyridin-3-ylmethyl) trimethyl ammonium iodide (9.85 g), sodium cyanide (4.57 g) and water (100 ml) was heated for 3.5 hours under reflux. The reaction mixture was concentrated, which was dissolved in a small volume of water, followed by adjusting the pH to 5–6 with acetic acid. To the reaction mixture was added ethanol, and the mixture was concentrated to dryness. The concentrate was dissolved in dimethylformamide (70 ml). To the solution were added potassium carbonate (15 g) and ethyl iodide (6 ml). The reaction mixture was stirred for one hour at room temperature, which was poured into water, followed by extraction with ethyl acetate. The organic layer was washed with water and a saturated aqueous saline solution, which was dried over anhydrous magnesium sulfate and, then, concentrated to afford the title compound (0.76 g) as an oily product.

IR(KBr): 1730, 1503, 1026, 754 cm$^{-1}$. $^1$H-NMR(CDCl$_3$) δ: 1.25(3H,t,J=7.2 Hz), 3.93(2H,s), 4.17(2H,q,J=7.2 Hz), 6.85(1H,t,J=7.0 Hz), 7.18(1H,dd,J=9.2,7.0 Hz), 7.56(1H,s), 7.63(1H,d,J=9.2 Hz), 8.06(1H,d,J=7.0 Hz).

REFERENCE EXAMPLE 23-2
2-(Imidazo[1,2-a]pyridin-3-yl)ethanol

The same reaction and purification as in Reference Example 18-1 were conducted, employing the compound produced in REFERENCE EXAMPLE 23-1, to afford the title compound.

IR(KBr): 3360, 1505, 1053, 752 cm$^{-1}$. $^1$H-NMR(CDCl$_3$) δ: 3.15(2H,t,J=6.2 Hz), 4.01(2H,t,J=6.2 Hz), 6.81(1H,t,J= 7.0 Hz), 7.14(1H,dd,J=9.2,7.0 Hz), 7.45(1H,s), 7.57(1H,d, J=9.2 Hz), 8.05(1H,d,J=7.0 Hz).

REFERENCE EXAMPLE 23-3
3-(2-Acetylthioethyl)imidazo[1,2-a]pyridine

The same reaction and purification as in Reference Example 20-3 were conducted, employing the compound produced in Reference Example 23-2, to afford the title compound.

IR(KBr): 1686, 1134, 754 cm$^{-1}$. $^1$H-NMR(CDCl$_3$)δ: 2.38 (3H,s), 3.15(4H,s), 6.88(1H,t,J=7.0 Hz), 7.19(1H,dd,J=9.2, 7.0 Hz), 7.46(1H,s), 7.62(1H,d,J=9.2 Hz), 8.24(1H,d,J=7.0 Hz).

REFERENCE EXAMPLE 24-1
2-Cyano-2'-(2-pyridyl)acetohydrazide

The same reaction and purification as in Reference Example 17-1 were conducted, employing 2-hydrazinopyridine (10.0 g) in place of 2-aminomethylpyridine, to afford the title compound (9.48 g).

$^1$H-NMR(CDCl$_3$+DMSO-d$_6$)δ: 3.54,3.64(2H,each s), 6.65–6.9(2H,m), 7.45–7.65(1H,m), 8.1–8.2(1H,m).

REFERENCE EXAMPLE 24-2
2-([1,2,4]Triazolo[4,3-a]pyridin-3-yl)acetonitrile

The same reaction and purification as in Reference Example 17-2 were conducted, employing 2-cyano-2'-(2-pyridyl)acetohydrazide (8.34 g) in place of 2-cyano-N-(2-pyridylmethyl)acetamide, to afford the title compound (6.13 g).

$^1$H-NMR(CDCl$_3$)δ: 4.39(2H,s), 7.0–7.1(1H,m), 7.3–7.45 (1H,m), 7.8–7.9(1H,m), 8.1–8.2(1H,m).

REFERENCE EXAMPLE 24-3
Methyl ([1,2,4]triazolo[4,3-a]pyridin-3-yl)acetate

The same reaction and purification as in Reference Example 17-3 were conducted, employing 2-(1,2,4-triazolo[4,3-a]pyridin-3-yl)acetonitrile (4.74 g) in place of 2-(imidazo[1,5-a]pyridin-3-yl)acetonitrile, to afford the title compound (3.08 g).

$^1$H-NMR(CDCl$_3$)δ: 3.75(3H,s), 4.28(2H,s), 6.85–6.95 (1H,m), 7.2–7.35(1H,m), 7.75–7.85(1H,m), 8.0–8.1(1H,m).

REFERENCE EXAMPLE 24-4
2-([1,2,4]Triazolo[4,3-a]pyridin-3-yl)ethanol

The same reaction an d purification as in Reference Example 17-4 were conducted, employing methyl 2-(1,2,4-triazolo[4,3-a]pyridin-3-yl)acetate (2.05 g) in place of methyl 2-(imidazo[1,5-a]pyridin-3-yl)acetate, to afford the title compound (2.10 g).

$^1$H-NMR(DMSO-d$_6$)δ: 3.37(2H,t,J=6.6 Hz), 3.96(2H,dt, J=5.2,6.6 Hz), 5.03(1H,t,J=5.2 Hz), 7.0–7.1(1H,m), 7.35–7.5(1H,m), 7.75–7.9(1H,m), 8.5–8.6(1H,m).

REFERENCE EXAMPLE 24-5
3-(2-Acetylthioethyl)[1,2,4]triazolo[4,3-a]pyridine

The same reaction and purification as in Reference Example 6-2 were conducted, employing 2-([1,2,4]triazolo[4,3-a]pyridin-3-yl)ethanol (1.36 g) in place of 2-(6-amino-2-pyridyl)ethanol, to afford the title compound (0.87 g).

$^1$H-NMR(CDCl$_3$)δ: 2.39(3H,s), 3.25–3.5(4H,m), 6.85–7.0(1H,m), 7.2–7.35(1H,m), 7.7–7.8(1H,m), 8.2–8.3 (1H,m).

REFERENCE EXAMPLE 24-6
2-([1,2,4]Triazolo[4,3-a]pyridin-3-yl)ethanethiol

The same reaction and purification as in Reference Example 6-3 were conducted, employing 3-(2-acetylthioethyl)[1,2,4]triazolo[4,3-a]pyridine (0.93 g) in place of 6-(2-acetylthioethyl)-2-aminopyridine, to afford the title compound (678 mg).

$^1$H-NMR(CDCl$_3$)δ: 1.81(1H,t,J=8.4 Hz), 3.1–3.5(4H,m), 6.8–6.95(1H,m), 7.2–7.35(1H,m), 7.7–7.8(1H,m), 7.9–8.0 (1H,m).

REFERENCE EXAMPLE 25-1
4-Nitrobenzyl 4-bromo-3-oxopentanoate

2-Bromopropionyl chloride (8.57 g) was dissolved in acetonitrile (200 ml). To the solution were added, at 0° C., imidazole (6.81 g) and magnesium p-nitrobenzyl malonate (25.0 g). The mixture was stirred for 6 hours at 25° C. Insolubles were filtered off, and the filtrate was concentrated. To the concentrate were added water (100 ml) and ethyl ether (100 ml). The mixture was shaken and left standing to form two layers. The organic layer was dried over anhydrous magnesium sulfate, which was then concentrated under reduced pressure. The concentrate was purified by means of a column chromatography (carrier: silica gel, 50 g, developing solvent: hexane-ethyl acetate, 2:1) to afford the title compound (1.92 g).

$^1$H-NMR(CDCl$_3$)δ: 1.64(3H,d,J=7.0 Hz), 3.80(1H,d,J= 16.4 Hz), 3.90(1H,d,J=16.4 Hz), 4.49(1H,q,J=7.0 Hz), 5.29 (2H,s), 7.54(2H,d,J=8.8 Hz), 8.24(2H,d,J=8.8 Hz).

REFERENCE EXAMPLE 25-2
4-Nitrobenzyl 2-(3-methylimidazo[1,2-a]pyridin-2-yl) acetate 4-Nitrobenzyl 4-bromo-3-oxopentanoate (1.02 g) and 2-aminopyridine (436 mg) were dissolved in 1,2-dimethoxyethane (20 ml). The solution was heated for 15 hours under reflux. The reaction mixture was concentrated, to which were added 1N HCl (10 ml) and ethyl acetate (10 ml). The mixture was shaken and left standing to form two layers. To the aqueous layer was added sodium hydrogencarbonate to adjust its pH to 7, followed by extraction with ethyl acetate. The extract was dried over anhydrous magnesium sulfate, which was concentrated under reduced pressure. The concentrate was purified by means of a column chromatography (carrier: silica gel, 30 g, developing: ethyl acetate) to afford the title compound (0.27 g).

$^1$H-NMR(CDCl$_3$)δ: 2.44(3H,s), 3.93(2H,s), 5.26(2H,s), 6.8–6.9(1H,m), 7.1–7.25(1H,m), 7.50(2H,d,J=8.8 Hz), 7.5–7.6(1H,m), 7.8–7.9(1H,m), 8.19(2H,d,J=8.8 Hz).

REFERENCE EXAMPLE 25-3
2-(3-Methylimidazo[1,2-a]pyridin-2-yl)ethanol

The same reaction and purification as in Reference Example 17-4 were conducted, employing 4-nitrobenzyl 2-(3-methylimidazo[1,2-a]pyridin-2-yl)acetate (0.27 g) in place of methyl 2-(imidazo[1,5-a]pyridin-3-yl)acetate, to afford the title compound (114 mg).

$^1$H-NMR(CDCl$_3$)δ: 2.42(3H,s), 2.97(2H,t,J=5.6 Hz), 4.02 (2H,t,J=5.6 Hz), 6.75–6.9(1H,m), 7.1–7.2(1H,m), 7.45–7.6 (1H,m), 7.8–7.9(1H,m).

REFERENCE EXAMPLE 25-4
2-(2-Acetylthioethyl)-3-methylimidazo[1,2-a]pyridine

The same reaction and purification as in Reference Example 6-2 were conducted, employing 2-(3-methylimidazo[1,2-a]pyridin-2-yl)ethanol (307 mg) in place of 2-(6-amino-2-pyridyl)ethanol, to afford the title compound (441 mg).

$^1$H-NMR(CDCl$_3$)δ: 2.33(3H,s), 2.44(3H,s), 3.04(2H,t,J= 7.2 Hz), 3.29(2H,t,J=7.2 Hz), 6.75–6.9(1H,m), 7.05–7.2(1H, m), 7.4–7.6(1H,m), 7.75–7.9(1H,m).

REFERENCE EXAMPLE 25-5
2-(3-Methylimidazo[1,2-a]pyridin-2-yl)ethanethiol

The same reaction and purification as in Reference Example 6-3 were conducted, employing 2-(2-acetylthioethyl)-3-methylimidazo[1,2-a]pyridine (441 mg) in place of 6-(2-acetylthioethyl)-2-aminopyridine, to afford the title compound (403 mg).

$^1$H-NMR(CDCl$_3$)δ: 1.46(1H,t,J=7.8 Hz), 2.45(3H,s), 2.9–3.2(4H,m), 6.75–6.9(1H,m), 7.1–7.2(1H,m), 7.8–7.9 (1H,m).

REFERENCE EXAMPLE 26-1
Ethyl 6-nitroimidazo[1,2-a]pyridin-2-yl acetate

A mixture of 2-amino-5-nitropyridine (16.28 g), ethyl 4-chloroacetoacetate (30.60 g) and ethanol (150 ml) was heated for 24 hours under reflux. The reaction mixture was cooled and, then, resulting crystalline precipitate was collected by filtration. The crystals were dissolved in water, and the solution was neutralized with a saturated aqueous solution of sodium hydrogencarbonate, followed by extraction with ethyl acetate. The organic layer was dried over anhydrous magnesium sulfate and, then, concentrated to give pale brown crystals. The crystals were washed with diisopropyl ether to afford the title compound (15.75 g), m.p.101–102° C. (ethanol).

IR(KBr): 1721, 1348, 1333, 1209, 747 cm$^{-1}$. $^1$H-NMR (CDCl$_3$)δ: 1.31(3H,t,J=7.0 Hz), 3.92(2H,s), 4.24(2H,q,J=7.0 Hz), 7.62(1H,d,J=10.0 Hz), 7.84(1H,s), 7.95(1H,dd,J=10.0, 2.2 Hz), 9.23(1H,d,J=2.2 Hz). Elemental Analysis for C$_{11}$H$_{11}$N$_3$O$_4$: Calcd.: C, 53.01; H, 4.45; N, 16.86. Found : C, 52.85; H, 4.54; N, 16.77.

REFERENCE EXAMPLE 26-2
Ethyl 6-aminoimidazo[1,2-a]pyridin-2-yl acetate

The compound (6.13 g) produced in Reference Example 26-1 was dissolved in methanol (220 ml). To the solution was added 5% palladium carbon (2.98 g). The mixture was stirred for one hour at room temperature under hydrogen atmosphere. The catalyst was filtered off, and the filtrate was concentrated to leave pale green crystals. The crystals were washed with diisopropyl ether to afford the title compound (5.02 g).

IR(KBr): 3393, 3310, 3183, 1728, 1505, 1252 cm$^{-1}$.
$^1$H-NMR(CDCl$_3$)δ: 1.28(3H,t,J=7.0 Hz), 3.39(2H,br), 3.81 (2H,s), 4.20(2H,q,J=7.0 Hz), 6.76(1H,dd,J=9.2,2.0 Hz), 7.38(1H,d,J=9.2 Hz), 7.42(1H,s), 7.52(1H,d,J=2.0 Hz).

REFERENCE EXAMPLE 26-3
2-(6-Aminoimidazo[1,2-a]pyridin-2-yl)ethanol

The same reaction and purification as in Reference Example 20-2 were conducted, employing the compound produced in Reference Example 26-2, to afford the title compound.

IR(KBr): 3339, 3220, 3133, 1507, 1047 cm$^{-1}$. $^1$H-NMR (CDCl$_3$+DMSO-$_6$)δ: 2.94(2H,t,J=6.0 Hz), 3.76(2H,br), 3.93 (2H,t,J=6.0 Hz), 6.80(1H,dd,J=9.4,2.0 Hz), 7.28(1H,s), 7.32 (IH,d,J=9.4 Hz), 7.57(1H,d,J=2.0 Hz).

REFERENCE EXAMPLE 26-4
2-(2-Acetylthioethyl)-6-aminoimidazo[1,2-a]pyridine

The same reaction and purification as in Reference Example 21 were conducted, employing the compound produced in Reference Example 26-3, to afford the title compound.

IR(KBr): 3310, 3185, 1688, 1503, 1188, 1142, 631 cm$^{-1}$.
$^1$H-NMR(CDCl$_3$)δ: 2.33(3H,s), 3.01(2H,t,J=7.2 Hz), 3.28 (2H,t,J=7.2 Hz), 3.20–3.60(2H,br), 6.76(1H,dd,J=9.2,2.2 Hz), 7.24(1H,s), 7.37(1H,d,J=9.2 Hz), 7.52(1H,d,J=2.2 Hz).

REFERENCE EXAMPLE 27-1
Ethyl 8-aminoimidazo[1,2-a]pyridin-2-yl acetate

A mixture of 2,3-diaminopyridine (5.20 g), ethyl 4-bromoacetoacetate (10.50 g) and ethanol (60 ml) was stirred for one hour at room temperature, which was the heated for 16 hours under reflux. The solvent was distilled off, and the residue was dissolved in water. The solution was neutralized with a saturated aqueous solution of sodium hydrogencarbonate, followed by extraction with ethyl acetate. The organic layer was washed with a saturated aqueous saline solution, dried over anhydrous magnesium sulfate and concentrated. The concentrate was purified by means of a column chromatography (carrier: silica gel, developing solvent: ethyl acetate-hexane, 3:2) to afford the title compound (1.70 g) as an oily product.

IR(KBr): 3449, 3362, 3210, 1732, 1557, 1495, 1323, 1175, 1032, 741 cm$^{-1}$. $^1$H-NMR(CDCl$_3$)δ: 1.29(3H,t,J=7.0 Hz), 3.84(2H,s), 4.20(2H,q,J=7.0 Hz), 4.46(2H,br), 6.29 (1H,dd,J=6.9,1.0 Hz), 6.58(1H,t,J=6.9 Hz), 7.51(1H,s), 7.54 (1H,dd,J=6.9,1.0 Hz).

REFERENCE EXAMPLE 27-2
2-(8-Aminoimidazo[1,2-a]pyridin-2-yl)ethanol

The same reaction and purification as in Reference Example 20-2 were conducted, employing the compound produced in Reference Example 27-1, to afford the title compound.

$^1$H-NMR(DMSO-d$_6$)δ: 2.80(2H,t,J=7.0 Hz), 3.71(2H,t,J= 7.0 Hz), 5.47(2H,br), 6.18(1H,d,J=7.0 Hz), 6.54(1H,t,J=7.0 Hz), 7.55(1H,s), 7.68(1H,d,J=7.0 Hz).

REFERENCE EXAMPLE 27-3
2-(2-Acetylthioethyl)-8-aminoimidazo[1,2-a]pyridine

The same reaction and purification as in Reference Example 20-3 were conducted, employing the compound produced in Reference Example 27-2, to afford the title compound.

IR(KBr): 3439, 3056, 1686 cm$^{-1}$. $^1$H-NMR(CDCl$_3$)δ: 2.34(3H,s), 3.04(2H,t,J=7.0 Hz), 3.30(2H,t,J=7.0 Hz), 4.44 (2H,br), 6.29(1H,d,J=7.0 Hz), 6.56(1H,t,J=7.0 Hz), 7.33 (1H,s), 7.55(1H,d,J=7.0 Hz).

REFERENCE EXAMPLE 28
5-(2-Acetylthioethyl)imidazo[5,1-b]thiazole 2-(Imidazo[5,1-b]thiazol-5-yl)ethanol (841 mg) was subjected to the same reaction and purification as in Reference Example 6-2 to afford the title compound (1095 mg).

IR(KBr): 1686 cm$^{-1}$. $^1$H-NMR(CDCl$_3$)δ: 2.37(3H,s), 3.1–3.3(4H,m), 6.82(1H,d,J=4.1 Hz), 6.99(1H,s), 7.52(1H, d,J=4.1 Hz).

REFERENCE EXAMPLE 29-1
Ethyl imidazo[1,2-a]pyrimidin-2-yl acetate

Employing 2-aminopyrimidine, the same reaction and purification as in Reference Example 27-1 was conducted to afford the title compound.

IR(KBr): 1732, 1507, 1267, 1173, 1030, 768 cm$^{-1}$.
$^1$H-NMR(CDCl$_3$)δ: 1.30(3H,t,J=7.2 Hz), 3.94(2H,s), 4.22 (2H,q,J=7.2 Hz), 6.86(1H,dd,J=7.0,4.0 Hz), 7.61(1H,s), 8.39(1H,dd,J=7.0,1.8 Hz), 8.53(1H,dd,J=4.0,1.8 Hz).

REFERENCE EXAMPLE 29-2
2-(Imidazo[1,2-a]pyrimidin-2-yl)ethanol

To a solution of the compound (4.60 g) produced in Reference Example 29-1 in tetrahydrofuran (150 ml) was added dropwise, at temperatures ranging from −75 to 65° C., a 1.5M toluene solution of diisobutyl aluminium hydride (45 ml). The mixture was stirred for two hours at the same temperature range, which was warmed up to −40° C. in the course of one hour, followed by stirring for one hour at −40° C. To the reaction mixture was added water (5 ml) dropwise to raise the temperature up to room temperature. The resulting insolubles were filtered off, and the filtrate was concentrated. The concentrate was purified by means of a column chromatography (carrier: silica gel, developing solvent: ethyl acetate-methanol, 5:1) to give pale brown crystals. The crystalline product was washed with ethyl acetate, then, with ether to afford the title compound (0.59 g).

IR(KBr): 3223, 1514, 1267, 1063, 760 cm$^{-1}$. $^1$H-NMR (CDCl$_3$)δ: 3.05(2H,t,J=5.8 Hz), 4.05(2H,t,J=5.8 Hz), 6.86 (1H,dd,J=6.8,4.0 Hz), 7.39(1H,s), 8.39(1H,dd,J=6.8,2.0 Hz), 8.52(1H,dd,J=4.2,2.0 Hz).

REFERENCE EXAMPLE 29-3
2-(2-Acetylthioethyl)imidazo[1,2-a]pyrimidine

The same reaction and purification as in Reference Example 21 were conducted, employing the compound produced in Reference Example 29-2, to afford the title compound, m.p.122.0–123.5° C. (ethyl acetate).

IR(KBr): 1686, 1508, 1348, 1138, 797, 629 cm$^{-1}$.
$^1$H-NMR(CDCl$_3$)δ: 2.34(3H,s), 3.12(2H,t,J=7.0 Hz), 3.35 (2H,t,J=7.0 Hz), 6.84(1H,dd,J=6.6,4.2 Hz), 7.37(1H,s), 8.36 (1H,dd,J=6.6,2.2 Hz), 8.51(1H,dd,J=4.2,2.2 Hz).

REFERENCE EXAMPLE 30
2-(2-Acetylthioethyl)-5-ureidoimidazo[1,2-a]pyridine

To a solution of the compound (2.05 g) produced in Reference Example 20-3 in tetrahydrofuran (30 ml) was added dropwise, at −15° C., chlorosulfonyl isocyanate (1.12 ml). The mixture was stirred for one hour at 0° C., to which was added 1N HCl (16 ml), followed by stirring for 15 hours at room temperature. The reaction mixture was diluted with water, which was neutralized with a saturated aqueous solution of sodium hydrogencarbonate, followed by extraction with ethyl acetate-tetrahydrofuran (1:1) four times. The organic layers were combined, dried over anhydrous magnesium sulfate and concentrated. The concentrate was purified by means of a column chromatography (carrier:silica gel, developing solvent: ethyl acetate-methanol, 10:1) to give white crystals. The crystalline product was washed with ether to afford the title compound (0.35 g).

IR(KBr): 3362, 3144, 1676, 1541, 1512, 1146, 777, 631 cm$^{-1}$. $^1$H-NMR(DMSO-d$_6$)δ: 2.34(3H,s), 2.97(2H,t,J=7.2 Hz), 3.24(2H,t,J=7.2 Hz), 6.43(2H,brs), 7.14–7.30(3H,m), 7.68(1H,s), 8.91(1H,brs).

REFERENCE EXAMPLE 31-1

1-Imidazo[1,5-a]pyridin-1-yl-2-(4-methoxybenzylthio)ethanone

To a DMF solution (4 ml) of 4-methoxytoluene thiol (0.86 ml) was added 60% sodium hydride (181 mg). The mixture was stirred for 10 minutes at room temperature and for 20 minutes at 70° C. The reaction mixture was cooled to 0° C., to which was added 2-chloro-1-imidazo[1,5-a]pyridin-1-yl ethanone (800 mg). The mixture was stirred for one hour under ice-cooling. To the reaction mixture was added ice-water, which was subjected to extraction with ethyl acetate. The extract was dried over magnesium sulfate, which was then concentrated under reduced pressure. The concentrate was purified by means of a flash column chromatography (carrier: silica gel, 30 g, developing solvent: ethyl acetate-hexane, 1:2→2:3) to afford the title compound (800 mg) as a colorless solid product.

IR(KBr): 1640, 1512, 1420, 1242 cm$^{-1}$. $^1$H-NMR(CDCl$_3$)δ: 3.79(3H,s), 3.83(2H,s), 3.87(2H,s), 6.84(2H,d,J=8.6 Hz), 6.80–6.95(1H,m), 7.15–7.30(1H,m), 7.34(2H,d,J=8.6 Hz), 8.05–8.15(2H,m), 8.35–8.45(1H,m).

REFERENCE EXAMPLE 31-2

1-[2-(4-Methoxybenzylthio)ethyl]imidazo[1,5-a]pyridine

To a solution of the compound (2.67 g) produced by the method described in Reference Example 31-1 in diethyleneglycol dimethyl ether (30 ml) were added, under ice-cooling, sodium borohydride (1.29 g) and a boron trifluoride diethyl ether complex (4.21 ml), successively. The mixture was stirred for 3 days at room temperature. The reaction mixture was concentrated under reduced pressure, to which was added, under ice-cooling, methanol (30 ml). The mixture was heated for 10 minutes under reflux. The reaction mixture was then cooled to room temperature, which was concentrated under reduced pressure. To the concentrate was added ethyl acetate, which was washed with a saturated aqueous solution of sodium hydrogencarbonate and a saturated aqueous saline solution, successively. The organic layer was dried over anhydrous magnesium sulfate. The solvent was distilled off under reduced pressure. The residue was purified by means of a flash column chromatography (carrier: silica gel, 60 g, developing solvent: ethyl acetate-hexane, 1:2) to afford the title compound (1.60 g) as a colorless oily product.

IR(KBr): 1609, 1510, 1246, 1174 cm$^{-1}$. $^1$H-NMR(CDCl$_3$) δ: 2.89(2H,t,J=7.2 Hz), 3.26(2H,t,J=7.2 Hz), 3.68(2H,s), 3.79(3H,s), 6.65–6.90(4H,m), 7.22(2H,d,J=8.8 Hz), 7.38 (1H,d,J=7.0 Hz), 7.83(1H,dt,J=7.0,1.2 Hz), 8.34(1H,s).

REFERENCE EXAMPLE 32-1

Ethyl 3-nitroimidazo[1,2-a]pyridin-2-yl acetate

Ethyl imidazo[1,2-a]pyridin-2-yl acetate (7.56 g) was dissolved in conc. sulfuric acid (7.4 ml), to which was added dropwise, at −15° C., fuming nitric acid (6.0 ml). The reaction mixture was stirred for 0.5 hour at 0° C., which was poured into ice-water and neutralized with 6N sodium hydroxide, followed by extraction with ethyl acetate. The organic layer was dried over anhydrous magnesium sulfate, followed by concentration to leave yellow crystals. The crystalline product was washed with ethanol, then, with ether to afford the title compound (4.83 g).

IR(KBr): 1728, 1383, 1229, 1211, 766 cm$^{-1}$. $^1$H-NMR(CDCl$_3$)δ: 1.30(3H,t,J=7.2 Hz), 4.24(2H,q,J=7.2 Hz), 4.28 (2H,s), 7.30(1H,t,J=7.0 Hz), 7.66(1H,dd,J=9.2,7.0 Hz), 7.82 (1H,d,J=9.2 Hz), 9.46(1H,d,J=7.0 Hz). Melting point 150–153° C. (ethanol) Elemental Analysis for C$_{11}$H$_{11}$N$_3$O$_4$: Calcd.: C, 53.01; H, 4.45; N, 16.86. Found : C, 52.82; H, 4.30; N, 16.87.

REFERENCE EXAMPLE 32-2

Ethyl 3-aminoimidazo[1,2-a]pyridin-2-yl acetate

The compound (3.00 g) produced in Reference Example 32-1 was dissolved in methanol (250 ml). To the solution was added 5% palladium carbon (1.50 g), and the mixture was stirred for 12 hours at room temperature under hydrogen atmosphere. The catalyst was filtered off, and the filtrate was concentrated. The concentrate was purified by means of a column chromatography (carrier: silica gel, developing solvent: ethyl acetate-methanol, 5:1) to give pale yellow crystals. The crystalline product was washed with diisopropyl ether to afford the title compound (1.31 g), m.p.131.5–133.5° C. (ethyl acetate).

IR(KBr): 3374, 3185, 1717, 1194, 745 cm$^{-1}$. $^1$H-NMR(CDCl$_3$)δ: 1.27(3H,t,J=7.2 Hz), 3.36(2H,br), 3.84(2H,s), 4.17(2H,q,J=7.2 Hz), 6.76(1H,t,J=6.8 Hz), 7.06(1H,dd,J=9.0,6.8 Hz), 7.43(1H,d,J=9.0 Hz), 7.97(1H,d,J=6.8 Hz). Elemental Analysis for C$_{11}$H$_{13}$N$_3$O$_2$: Calcd.: C, 60.26; H, 5.98; N, 19.17. Found : C, 60.11; H, 5.75; N, 19.20.

REFERENCE EXAMPLE 32-3

2-(3-Aminoimidazo[1,2-a]pyridin-2-yl)ethanol

The same reaction and purification as in Reference Example 20-2 were conducted, employing the compound produced in Reference Example 32-2, to afford the title compound.

$^1$H-NMR(CDCl$_3$)δ: 2.93(2H,t,J=5.8 Hz), 3.32(2H,br), 3.95(2H,t,J=5.8 Hz), 6.70(1H,t,J=7.0 Hz), 6.99(1H,dd,J=8.8,7.0 Hz), 7.33(1H,d,J=8.8 Hz), 7.90(1H,d,J=7.0 Hz).

REFERENCE EXAMPLE 32-4.

2-(2-Acetylthioethyl)-3-aminoimidazo[1,2-a]pyridine

The same reaction and purification as in Reference Example 20-3 were conducted, employing the compound produced in Reference Example 32-3, to afford the title compound.

IR(KBr): 3374, 3187, 1667, 1584, 1254, 1142, 1109, 737 cm$^{-1}$. $^1$H-NMR(CDCl$_3$)δ: 2.35(3H,s), 3.04(2H,t,J=7.0 Hz), 3.18(2H,br), 3.27(2H,t,J=7.0 Hz), 6.79(1H,t,J=6.8 Hz), 7.07 (1H,dd,J=9.2,6.8 Hz), 7.45(1H,d,J=9.2 Hz), 8.00(1H,d,J=6.8 Hz).

REFERENCE EXAMPLE 33-1

2-(Isoquinolin-1-yl)ethanol

Employing ethyl isoquinolin-1-ylacetate, the same reaction and purification as in Reference Example 18-1 were conducted to give the title compound.

IR(KBr): 3140, 1055, 747 cm$^{-1}$. $^1$H-NMR(CDCl$_3$) δ: 3.50(2H,t,J=5.4 Hz), 4.24(2H,t,J=5.4 Hz), 4.50–5.10(1H, br), 7.54–7.74(3H,m), 7.83(1H,d,J=7.8 Hz), 8.12(1H,d,J= 8.0 Hz), 8.40(1H,d,J=5.8 Hz).

REFERENCE EXAMPLE 33-2

1-(2-Acetylthioethyl)isoquinoline

Employing the compound produced in Reference Example 33-1, the same reaction and purification as in Reference Example 18-2 were conducted to give the title compound.

IR(KBr): 1680, 1138, 831, 635 cm$^{-1}$. $^1$H-NMR(CDCl$_3$) δ: 2.36(3H,s), 3.39–3.65(4H,m), 7.55(1H,d,J=5.8 Hz), 7.63–7.86(3H,m), 8.29(1H,d,J=7.8 Hz), 8.46(1H,d,J=5.8 Hz).

REFERENCE EXAMPLE 34

2-(2-Benzoylthioethyl)-1-methylimidazole

Triphenylphosphine (10.48 g) was dissolved in tetrahydrofuran (120 ml). To the solution were added diisopropyl azodicarboxylate (8.07 g) at 0° C. The mixture was stirred for 15 minutes at the same temperature. To the mixture were added a solution of 2-(1-methyl-2-imidazolyl)ethanol (2.52 g) in tetrahydrofuran (10 ml) and thiobenzoic acid (4.7 ml) in the order mentioned. The mixture was stirred for 2.5 hours at 0° C. and then for 1 hour at room temperature. The reaction mixture was diluted with ethyl acetate, then washed with saturated solution of sodium hydrogencarbonate in water and saturated solution of sodium chloride in water in the order mentioned. The residue was dried over anhydrous sodium sulfate and concentrated under reduced pressure, which was then subjected to column chloromatography on silica gel (developing solvent: ethyl acetate-methanol: 100:0→93:7) to give the title compound (3.52 g).

IR(KBr): 1659 cm$^{-1}$. $^1$H-NMR(CDCl$_3$) δ: 3.06(2H,t,J=7.5 Hz), 3.45(2H,t,J=7.5 Hz), 3.66(3H,s), 6.83(1H,d,J=1.2 Hz), 6.97(1H,d,J=1.2 Hz), 7.4–7.65(3H,m), 7.9–8.05(2H, m).

REFERENCE EXAMPLE 35-1

2-(1-Phenylimidazol-2-yl)ethanol

1-Phenylimidazole (3.00 g) was dissolved in tetrahydrofuran. To the solution was added dropwise a solution of n-butyllithium (1.6 M) in hexane (16.9 ml) at −70° C. The mixture was stirred for 30 minutes at the same temperature, to which 50% solution (4.76 g) of ethyleneoxide in tetrahydrofuran. The mixture was warmed up to room temperature over 1 hour, and stirred 19 hours at the same temperature. To the reaction mixture was added water. The mixture was subjected to extraction with ethyl acetate. The extract was dried over anhydrous magnesium sulfate, followed by concentration under reduced pressure. The residue was subjected to column chromatography on silica gel (developing solvent: ethyl acetate-methanol 100:0→93:7) to give the title compound.

IR(KBr): 1503 cm$^{-1}$. $^1$H-NMR(CDCl$_3$) δ: 2.82(2H,t,J=5.5 Hz), 3.97(2H,t,J=5.5 Hz), 7.04(1H,d,J=1.2 Hz), 7.07 (1H,d,J=1.2 Hz), 7.2–7.6(5H,m).

REFERENCE EXAMPLE 35-2

2-(2-Acetylthioethyl)-1-phenylimidazole

Employing 2-(1-phenylimidazol-2-yl)ethanol (1.76 g), the same reaction and purification as in Reference Example 6-2 were conducted to give the title compound (1.85 g).

IR(KBr): 1690, 1501 cm$^{-1}$. $^1$H-NMR(CDCl$_3$) δ: 2.26(3H, s), 2.93(2H,t,J=6.9 Hz), 3.26(2H,t,J=6.9 Hz), 7.02(1H,d,J= 1.4 Hz), 7.10(1H,d,J=1.4 Hz), 7.25–7.65(5H,m).

WORKING EXAMPLE 1-1

4-nitrobenzyl (4R,5S,6S)-6-[(1R)-1-Hydroxyethyl]-4-methyl-7-oxo-3-[2-(2-thiazolyl)ethylthio]-1-azabicyclo[3.2.0]hepto-2-carboxylate To a solution of 2-(2-thiazolyl)ethanol (325 mg) in dichloromethane (4 ml) was added diisopropyl ethylamine (0.66 ml). To the mixture was added, at −70° C., trifluoromethanesulfonic anhydride (0.425 ml). The mixture was stirred for 15 minutes at the same temperature to give a solution of triflate compound. On the other hand, to a solution of 4-nitrobenzyl (4R,5R,6S)-3-[(diphenylphosphono)oxy]-6-[(R)-1-hydroxyethyl]-4-methyl-7-oxo-1-azabicyclo[3.2.0] hept-2-ene-2-carboxylate (1.00 g) in DMF (8 ml) was added dropwise, at −40° C., a solution of sodium hydrosulfide hydrate (0.20 g) in DMF (2 ml). To the mixture was added diisopropylethylamine (0.59 ml), which was stirred for 15 minutes at the same temperature. To the reaction mixture was added the solution of triflate compound prepared above, and the mixture was stirred for 30 minutes at temperatures ranging from −40 to −20° C. The reaction mixture was diluted with ethyl acetate (30 ml), which was washed three times with an aqueous saline solution (30 ml), followed by drying over anhydrous magnesium sulfate and concentration. The concentrate was purified by means of a column chromatography (carrier: silica gel, 50 g, developing solvent: ethyl acetate-acetone, 1:1) to afford the title compound (215 mg).

IR(neat): 1765, 1705 cm$^{-1}$. $^1$H-NMR(CDCl$_3$)δ: 1.26(3H, d,J=7.2 Hz), 1.36(3H,d,J=6.4 Hz), 1.75–1.85(1H,m), 3.2–3.4(4H,m), 3.27(1H,dd,J=2.6,6.8 Hz), 3.44(1H,dq,J= 9.2,7.2 Hz), 4.19(1H,dd,J=2.6,9.2 Hz), 4.15–4.35(1H,m), 5.24(1H,d,J=14.0 Hz), 5.52(1H,d,J=14.0 Hz), 7.25(1H,d,J= 3.4 Hz), 7.66(2H,d,J=8.4 Hz), 7.74(1H,d,J=3.4 Hz), 8.23 (2H,d,J=8.4 Hz).

WORKING EXAMPLE 1-2

Sodium (4R,5S,6S)-6-[(1R)-1-hydroxyethyl]-4-methyl-7-oxo-3-[2-(2-thiazolyl)ethylthio]-1-azabicyclo[3.2.0]hept-2-ene-2-carboxylate The compound produced in Working Example 1-1 (215 mg) was dissolved in a mixture of THF (15 ml) and a phosphate buffer solution (pH 7.0, 0.1M, 15 ml). To the solution was added 10% palladium-carbon (0.32 g). The mixture was stirred for one hour at room temperature under hydrogen atmosphere. The catalyst was filtered off and washed with water, and the filtrate was washed with diethyl ether (40 ml). The aqueous layer was concentrated under reduced pressure, which was purified by means of a column chromatography (carrier: HP20 SS, 50 ml, developing solvent: 10% aqueous solution of acetonitrile), followed by freeze-drying to afford the title compound (81 mg).

IR(KBr): 1745, 1590 cm$^{-1}$. $^1$H-NMR(D$_2$O)δ: 1.13(3H,d, J=7.2 Hz), 1.29(3H,d,J=6.6 Hz), 3.0–3.5(6H,m), 4.00(1H, dd,J=2.6,9.2 Hz), 4.22(1H,dq,J=6.2,6.6 Hz), 7.49(1H,d,J= 3.6 Hz), 7.76(1H,d,J=3.6 Hz).

WORKING EXAMPLE 2-1

4-Nitrobenzyl (4R,5S,6S)-6-[(1R)-1-hydroxyethyl]-4-methyl-7-oxo-3-[2-(1-triphenylmethyl-1,2,3-triazol-4-yl) ethylthio]-1-azabicyclo[3.2.0]hept-2-ene-2-carboxylate 2-(1-triphenylmethyl-1,2,3-triazol-4-yl)ethanol (2.15 g) was subjected to the same reaction and purification procedure as in Working Example 1-1 to afford the title compound (1.08 g ).

IR(neat): 1765, 1705, 1605 cm$^{-1}$. $^1$H-NMR(CDCl$_3$)δ: 1.21(3H,d,J=7.0 Hz), 1.33(3H,d,J=6.4 Hz), 2.85–3.4(4H,m), 3.22(1H,dd,J=2.4,6.8 Hz), 3.47(1H,dq,J=9.2,7.0 Hz), 4.05 (1H,dd,J=2.4,9.2 Hz), 4.17(1H,dq,J=6.8,6.4 Hz), 5.22(1H, d,J=14.0 Hz), 5.49(1H,d,J=14.0 Hz), 7.05–7.2(6H,m), 7.26 (1H,s), 7.25–7.4(9H,m), 7.65(2H,d,J=8.8 Hz), 8.21(2H,d,J= 8.8 Hz).

WORKING EXAMPLE 2-2

4-Nitrobenzyl (4R,5S,6S)-6-[(1R)-1-hydroxyethyl]-4-methyl-7-oxo-3-[2-(1,2,3-triazol-4-yl)ethylthio]-1-azabicyclo[3.2.0]hept-2-ene-2-carboxylate To a solution of the compound (1.08 g) produced by the method described in Working Example 2-1 in methanol (30 ml) was added 1N hydrochloric acid (0.20 ml). The mixture was stirred for one hour at room temperature. The reaction mixture was concentrated under reduced pressure, which was purified by means of a column chromatography (carrier: silica gel, 50 g, developing solvent: ethyl acetate) to afford the title compound (0.35 g).

IR(neat): 1760, 1700, 1515 cm$^{-1}$. $^1$H-NMR(CDCl$_3$)δ: 1.22(3H,d,J=7.4 Hz), 1.35(3H,d,J=6.2 Hz), 2.95–3.25 (4H;m), 3.26(1H,dd,J=2.6,6.4 Hz), 3.36(1H,dq,J=9.2,7.4 Hz), 4.16(1H,dd,J=2.6,9.2 Hz), 4.28(1H,dq,J=6.4,6.2 Hz), 5.24(1H,d,J=13.8 Hz), 5.50(1H,d,J=13.8 Hz), 7.54(1H,s), 7.65(2H,d,J=9.0 Hz), 8.22(2H,d,J=9.0 Hz).

WORKING EXAMPLE 2-3
Sodium (4R,5S,6S)-6-[(1R)-1-hydroxyethyl]-4-methyl-7-oxo-3-[2-(1,2,3-triazol-4-yl)ethylthio]-1-azabicyclo[3.2.0]hept-2-ene-carboxylate The compound produced by the method of Working Example 2-2 (0.44 g) was subjected to the same reaction and purification procedure as in Working Example 1-2 to afford the title compound (180 mg).

IR(KBr): 1745, 1585 cm$^{-1}$. $^1$H-NMR(D$_2$O)δ: 1.10(3H,d, J=7.4 Hz), 1.27(3H,d,J=6.4 Hz), 2.9–3.3(5H,m), 3.35(1H, dd,J=2.4,6.2 Hz), 3.94(1H,dd,J=2.4,9.0 Hz), 4.21(1H,dq,J= 6.2,6.4 Hz), 7.75(1H,s).

WORKING EXAMPLE 3-1
4-Nitrobenzyl (4R,5S,6S)-6-[(1R)-1-hydroxyethyl]-4-methyl-7-oxo-3-[2-(1-triphenylmethyl-3-pyrazolyl)ethylthio]-1-azabicyclo[3.2.0]hept-2-ene-2-carboxylate 2-(1-Triphenylmethyl-3-pyrazolyl)ethanol (2.15 g) was subjected to the same reaction and purification procedure as in Working Example 1-1 to afford the title compound (2.86 g).

IR(neat): 1765, 1705 cm$^{-1}$. $^1$H-NMR(CDCl$_3$)δ: 1.16(3H, d,J=7.4 Hz), 1.33(3H,d,J=6.2 Hz), 1.65–1.75(1H,m), 2.9–3.2(4H,m), 3.21(1H,dd,J=2.6,6.6 Hz), 3.35(1H,dq,J= 8.8,7.4 Hz), 4.08(1H,dd,J=2.6,8.8 Hz), 4.1–4.3(1H,m), 5.23 (1H,d,J=14.0 Hz), 5.51(1H,d,J=14.0 Hz), 6.05(1H,d,J=2.2 Hz), 7.05–7.2(6H,m), 7.22(1H,d,J=2.2 Hz), 7.2–7.35(9H, m), 7.65(2H,d,J=8.8 Hz), 8.21(2H,d,J=8.8 Hz).

WORKING EXAMPLE 3-2
4-Nitrobenzyl (4R,5S,6S)-6-[(1R)-1-hydroxyethyl]-4-methyl-7-oxo-3-[2-(3-pyrazolyl)ethylthio]-1-azabicyclo[3.2.0]hept-2-ene-2-carboxylate To a solution of the compound (1.46 g) produced by the method described in Working Example 3-1 in acetic acid (10 ml) was added water (4 ml). The mixture was stirred for 1.5 hour at room temperature. The reaction mixture was concentrated, and the concentrate was dissolved in ethyl acetate (10 ml). The solution was dried over anhydrous magnesium sulfate, which was then concentrated. The concentrate was purified by means of a column chromatography (carrier: silica gel, 50 g, developing solvent: ethyl acetate-acetone, 2:1) to give the title compound (147 mg).

IR(neat): 1760, 1705 cm$^{-1}$. $^1$H-NMR(CDCl$_3$)δ: 1.21(3H, d,J=7.2 Hz), 1.34(3H,d,J=6.4 Hz), 2.9–3.25(4H,m), 3.25 (1H,dd,J=2.4,6.6 Hz), 3.35(1H,dq,J=9.4,7.2 Hz), 4.16(1H, dd,J=2.4,9.4 Hz), 4.15–4.35(1H,m), 5.23(1H,d,J=13.6 Hz), 5.50(1H,d,J=13.6 Hz), 6.15(1H,d,J=2.2 Hz), 7.49(1H,d,J= 2.2 Hz), 7.65(2H,d,J=8.8 Hz), 8.21(2H,d,J=8.8 Hz).

WORKING EXAMPLE 3-3
Sodium (4R,5S,6S)-6-[(1R)-1-hydroxyethyl]-4-methyl-7-oxo-3-[2-(3-pyrazolyl)ethylthio]-1-azabicyclo[3.2.0]hept-2-ene-2-carboxylate The compound (221 mg) produced by the method described in Working Example 3-2 was subjected to the same reaction and purification procedure as in Working Example 1-2 to afford the title compound (44 mg).

IR(KBr): 1740, 1585 cm$^{-1}$. $^1$H-NMR(D$_2$O)δ: 1.12(3H,d, J=7.2 Hz), 1.29(3H,d,J=6.4 Hz), 2.9–3.3(4H,m), 3.23(1H, dq,J=9.2,7.2 Hz), 3.36(1H,dd,J=2.4,6.2 Hz), 4.00(1H,dd,J= 2.4,9.2 Hz), 4.23(1H,dq,J=6.2,6.4 Hz), 6.29(1H,d,J=2.2 Hz), 7.63(1H,d,J=2.2 Hz).

WORKING EXAMPLE 4-1
4-Nitrobenzyl (4R,5S,6S)-6-[(1R)-1-hydroxyethyl]-4-methyl-3-[(1R)-1-methyl-2-(2-pyridyl)ethylthio]-7-oxo-1-azabicyclo[3.2.0]hept-2-ene-2-carboxylate (S)-1-(2-Pyridyl)-2-propanol (170 mg) was subjected to the same reaction and purification procedure as in Working Example 1-1 to afford the title compound (210 mg).

IR(neat): 1765, 1705, 1515 cm$^{-1}$. $^1$H-NMR(CDCl$_3$)δ: 1.12(3H,d,J=7.4 Hz), 1.36(3H,d,J=6.0 Hz), 1.45(3H,d,J=6.6 Hz), 1.75(1H,br s), 2.92(1H,dd,J=9.2,14.0 Hz), 3.07(1H,dd, J=6.2,14.0 Hz), 3.23(1H,dd,J=2.6,6.8 Hz), 3.43(1H,dq,J= 9.0,7.4 Hz), 3.7–3.95(1H,m), 4.22(1H,dd,J=2.6,9.0 Hz), 4.15–4.35(1H,m), 5.21(1H,d,J=13.6 Hz), 5.51(1H,d,J=13.6 Hz)., 7.2–7.3(2H,m), 7.6–7.75(1H,m), 7.65(2H,d,J=8.8 Hz), 8.22(2H,d,J=8.8 Hz), 8.5–8.6(1H,m).

WORKING EXAMPLE 4-2
Sodium (4R,5S,6S)-6-[(1R)-1-hydroxyethyl]-4-methyl-3-[(1R)-1-methyl-2-(2-pyridyl)ethylthio]-7-oxo-1-azabicyclo[3.2.0]hept-2-ene-2-carboxylate The compound (380 mg) produced by the the method described in Working Example 4-1 was subjected to the same reaction and purification procedure as in Working Example 1-2 to afford the title compound (115 mg).

IR(KBr): 1745, 1590, 1390 cm$^{-1}$. $^1$H-NMR(D$_2$O)δ: 0.94 (3H,d,J=7.0 Hz), 1.26(3H,d,J=6.4 Hz), 1.39(3H,d,J=6.2 Hz), 2.89(1H,dd,J=9.6,14.0 Hz), 3.12(1H,dd,J=5.4,14.0 Hz), 3.35(1H,dd,J=2.4,6.2 Hz), 3.25–3.45(1H,m), 3.5–3.7(1H, m), 4.16(1H,dd,J=2.4,8.6 Hz), 4.21(1H,dq,J=6.2,6.4 Hz), 7.25–7.4(2H,m), 7.75–7.9(1H,m), 8.4–8.5(1H,m).

WORKING EXAMPLE 5-1
4-Nitrobenzyl (4R,5S,6S)-6-[(1R)-1-hydroxyethyl]-4-methyl-3-[(1S)-1-methyl-2-(2-pyridyl)ethylthio]-7-oxo-1-azabicyclo[3.2.0]hept-2-ene-2-carboxylate 1-(2-Pyridyl)-2-propanol (1.72 g) was subjected to the same reaction and purification procedure as in Working Example 1-1 to give a mixture (3.58 g) of two kinds of diastereomers of 4-nitrobenzyl ((4R,5S,6S)-6-[(1R)-1-hydroxyethyl]-4-methyl-3-[1-methyl-2-[2-pyridyl)ethylthio]-7-oxo-1-azabicyclo(3.2.0]hept-2-ene-2-carboxylate. This mixture was purified by means of a column chromatography (carrier: silica gel, 130 g, developing solvent: ethyl acetate-acetone, 9:1 to 1:1) to afford the title compound (0.56 g) and the compound (0.38 g) of Working Example 4-1.

IR(neat): 1765, 1705, 1515 cm$^{-1}$. $^1$H-NMR(CDCl$_3$)δ: 1.23(3H,d,J=7.4 Hz), 1.35(3H,d,J=7 Hz), 1.35(3H,d,J=7 Hz), 1.77(1H,br s), 2.99(1H,dd,J=7.4,13.8 Hz), 3.07(1H,dd, J=6.4,13.8 Hz), 3.23(1H,dd,J=2.4,6.8 Hz), 3.49(1H,dq,J= 9.2,7.4 Hz), 3.65–3.85 (1H,m), 3.98(1H,dd,J=2.4,9.2 Hz), 4.1–4.3(1H,m), 5.22(1H,d,J=13.6 Hz), 5.52(1H,d,J=13.6 Hz), 7.05–7.25(2H,m), 7.5–7.6(1H,m), 7.68(2H,d,J=8.8 Hz), 8.23(2H,d,J=8.8 Hz), 8.5–8.6(1H,m).

WORKING EXAMPLE 5-2
Sodium (4R,5S,6S)-6-[(1R)-1-hydroxyethyl]-4-methyl-3-[(1S)-1-methyl-2-(2-pyridyl)ethylthio]-7-oxo-1-azabicyclo[3.2.0]hept-2-ene-2-carboxylate The compound (0.56 g) produced by the method described in Working Example 5-1 was subjected to the same reaction and purification procedure as in Working Example 1-2 to afford the title compound (193 mg).

IR(KBr): 1745, 1590, 1390 cm$^{-1}$. $^1$H-NMR(D$_2$O)δ: 1.04 (3H,d,J=7.4 Hz), 1.23(3H,d,J=6.4 Hz), 1.40(3H,d,J=7.0 Hz), 2.90(1H,dd,J=10.0,13.4 Hz), 2.94(1H,dq,J=9.4,7.4 Hz), 3.20(1H,dd,J=4.6,13.4 Hz), 3.26(1H,dd,J=2.4,6.0 Hz), 3.45–3.65(1H,m), 3.57(1H,dd,J=2.4,9.4 Hz), 4.15(1H,dq,J=6.0,6.4 Hz), 7.25–7.4(2H,m), 7.65–7.8(1H,m), 8.4–8.5(1H, m).

WORKING EXAMPLE 6-1

4-Nitrobenzyl (4R,5S,6S)-[(1R)-1-hydroxyethyl]-4-methyl-3-[1-methyl-2-(1-triphenylmethyl-1,2,3-triazol-4-yl) ethylthio]-7-oxo-1-azabicyclo[3.2.0]hept-2-ene-2-carboxylate 1-(1-Triphenylmethyl-1,2,3-triazol-4-yl)-2-propanol was subjected to the same reaction and purification procedure as in Working Example 5-1 to afford diastereomer-1 and diastereomer-2 of the title compound.

Diastereomer-1

$^1$H-NMR(CDCl$_3$)δ: 1.19(3H,d,J=7.4 Hz), 1.29(3H,d,J=6.2 Hz), 1.36(3H,d,J=6.9 Hz), 2.90(1H,dd,J=7.2,14.7 Hz), 2.99(1H,dd,J=6.4,14.7 Hz), 3.19(1H,dd,J=2.4,6.9 Hz), 3.5–3.8(2H,m), 3.92(1H,dd,J=2.4,9.0 Hz), 4.0–4.15(1H,m), 5.18(1H,d,J=13.8 Hz), 5.47(1H,d,J=13.8 Hz), 7.0–7.4(16H, m), 7.63(2H,d,J=8.6 Hz), 8.18(2H,d,J=8.6 Hz).

Diastereomer-2

$^1$H-NMR(CDCl$_3$)δ: 1.10(3H,dd,J=7.3 Hz), 1.36(3H,d,J=6.4 Hz), 1.43(3H,d,J=6.7 Hz), 2.81(1H,dd,J=9.5,15.1 Hz), 3.03(1H,dd,J=5.2,15.1 Hz), 3.25(1H,dd,J=2.6,6.7 Hz), 3.39 (1H,dq,J=9.3,7.3 Hz), 3.55–3.8(1H,m), 4.23(1H,dd,J=2.6, 9.3 Hz), 4.15–4.35(1H,m), 5.22(1H,d,J=14.0 Hz), 5.50(1H, d,J=14.0 Hz), 7.05–7.4(16H,m), 7.66(2H,d,J=8.8 Hz), 8.21 (2H,d,J=8.8 Hz).

WORKING EXAMPLE 6-2

Sodium (4R,5S,6S)-6-[(1R)-1-hydroxyethyl]-4-methyl-3-[1-methyl-2-(1,2,3-triazol-4-yl) ethylthio]-7-oxo-1-azabicyclo[3.2.0]hept-2-ene-2-carboxylate Diastereomer-1 of the compound produced by the method described in Working Example 6-1 was subjected to the same reaction and purification procedure as i n Working Example 6-1. The resulting compound was subjected to the same reaction and purification procedure as in Working Example 2-3 to give Diastereomer-1 of the title compound. Diastereomer-2 of the compound produced by the method of Working Example 6-1 was also subjected to the same reaction and purification procedure as above to afford Diastereomer-2 of the title compound.

Diastereomer-1

IR(KBr): 1753, 1599, 1394 cm$^{-1}$. $^1$H-NMR(D$_2$O)δ: 1.10 (3H,d,J=7.2 Hz), 1.27(3H,d,J=6.3 Hz), 1.35(3H,d,J=7.0 Hz), 2.96(1H,dd,J=8.5,14.8 Hz), 3.0–3.2(1H,m), 3.18(1H,dd,J=5.0,14.8 Hz), 3.34(1H,dd, J=2.5,6.3 Hz), 3.45–3.65(1H,m), 3.81(1H,dd,J=2.5,9.2 Hz), 4.20(1H,dq,J=6.3, 6.3 Hz), 4.1–4.3(1H,m), 7.72(1H,s).

Diastereomer-2

IR(KBr): 1749, 1597, 1396 cm$^{-1}$. $^1$H-NMR(D$_2$O)δ: 1.03 (3H,d,J=7.4 Hz), 1.29(3H,d,J=6.3 Hz), 1.38(3H,d,J=6.4 Hz), 2.97(1H,dd,J=8.9,15.1 Hz), 3.11(1H,dd,J=5.4,15.1 Hz), 3.3–3.6(2H,m), 3.40(1H,dd,J=2.6,6.3 Hz), 4.20(1H,dd,J=2.6,9.0 Hz), 4.24(1H,dq,J=6.3,6.3 Hz), 7.85(1H,s).

WORKING EXAMPLE 7-1

4-Nitrobenzyl (4R,5S,6S)-3-[2-(6-amino-2-pyridyl) ethylthio]-6-[(1R)-1-hydroxyethyl]-4-methyl-7-oxo-1-azabicyclo[3.2.0]hept-2-ene-2-carboxylate In acetonitrile (30 ml) was dissolved 4-nitrobenzyl (4R, 5S,6S)-3-[(diphenylphosphono)oxy]-6-[(R)-1-hydroxyethyl]-4-methyl-7-oxo-1-azabicyclo[3.2.0]hept-2-ene-carboxylate (1.50 g). To the solution were added, at 0° C., 2-(6-amino-2-pyridyl)ethanethiol (0.43 g) and diisopropyl ethylamine (0.44 ml). The mixture was stirred for 16 hours at the same temperature. The reaction mixture was concentrated, which was shaken with ethyl acetate (50 ml) and water (50 ml). The organic layer was dried over anhydrous magnesium sulfate and, then, concentrated. The concentrate was purified by means of a column chromatography (carrier: silica gel, 50 g, developing solvent: acetic acid-acetone, 2:1) to afford the title compound (0.61 g).

IR(neat): 1760, 1700, 1610 cm$^{-1}$. $^1$H-NMR(CDCl$_3$)δ: 1.24(3H,d,J=7.2 Hz), 1.36(3H,d,J=6.4 Hz), 2.85–3.35(4H, m), 3.25(1H,dd,J=2.4,6.6 Hz), 3.46(1H,dq,J=9.2,7.2 Hz), 4.16(1H,dd,J=2.4,9.2 Hz), 4.26(1H,dq,J=6.6,6.4 Hz), 4.41 (2H,br s), 5.22(1H,d,J=13.8 Hz), 5.51(1H,d,J=13.8 Hz), 6.37(1H,d,J=7.6 Hz), 6.50(1H,d,J=7.2 Hz), 7.34(1H,dd,J=7.2,7.6 Hz), 7.65(2H,d,J=9.0 Hz), 8.22(2H,d,J=9.0 Hz).

WORKING EXAMPLE 7-2

Sodium (4R,5S,6S)-3-[2-(6-amino-2-pyridyl)ethylthio]-6-[(1R)-1-hydroxyethyl]-4-methyl-7-oxo-1-azabicyclo [3.2.0]hept-2-ene-2-carboxylate The compound (0.61 g) produced by the method of Working Example 7-1 was subjected to the same reaction and purification procedure as in Working Example 1-2 to afford the title compound (78 mg).

IR(KBr): 1745, 1580, 1465, 1390 cm$^{-1}$. $^1$H-NMR(D$_2$O)δ: 1.07(3H,d,J=7.4 Hz), 1.26(3H,d,J=6.2 Hz), 2.75–3.25(5H, m), 3.31(1H,dd,J=2.2,6.4 Hz), 3.87(1H,dd,J=2.2,9.0 Hz), 4.19(1H,dq,J=6.4,6.2 Hz), 6.59(1H,d,J=8.4 Hz), 6.68(1H,d, J=7.4 Hz), 7.48(1H,dd,J=7.4,8.4 Hz).

WORKING EXAMPLE 8-1

4-Nitrobenzyl (4R,5S,6S)-6-[(1R)-1-hydroxyethyl]-4-methyl-7-oxo-3-[2-(4-pyrimidinyl)ethylthio]-1-azabicyclo [3.2.0]hept-2-ene-2-carboxylate To a solution of 4-(2-acetylthioethyl)pyrimidine (547 mg) in methanol (15 ml) was added, at 0° C., sodium methylate (a 28% methanol solution, 579 mg). The mixture was stirred for 30 minutes at the same temperature. To the reaction mixture was added 2N hydrochloric acid (1.5 ml). The mixture was concentrated under reduced pressure. The concentrate was subjected to extraction with ethyl acetate (50 ml). The extract was dried over anhydrous magnesium sulfate, which was then concentrated. The concentrate and 4-nitrobenzyl (4R,5S,6S)-3-[(diphenylphosphono)oxy]-6-[(R)-1-hydroxyethyl]-4-methyl-7-oxo-1-azabicyclo[3.2.0] hept-2-ene-2-carboxylate (1.64 g) were dissolved in acetonitrile (30 ml). To the solution was added at 0° C. diisopropyl ethylamine (0.53 ml), and the mixture was stirred for 5 hours at 25° C. The reaction mixture was concentrated, which was shaken with ethyl acetate (50 ml) and water (50 ml). The organic layer was dried over anhydrous magnesium sulfate, which was then concentrated. The concentrate was purified by means of a column chromatography (carrier: silica gel, 100 g, developing solvent: ethyl acetate) to give the title compound (916 mg).

$^1$H-NMR(CDCl$_3$)δ: 1.27(3H,d,J=7.1 Hz), 1.37(3H,d,J=6.2 Hz), 3.0–3.4(5H,m), 3.49(1H,dq,J=9.2,7.1 Hz), 4.22(1H, dd,J=2.6,9.2 Hz), 4.15–4.35(1H,m), 5.23(1H,d,J=13.9 Hz), 5.51(1H,d,J=13.9 Hz), 7.21(1H,dd,J=1.3,5.1 Hz), 7.66(2H, d,J=8.9 Hz), 8.23(2H,d,J=8.9 Hz), 8.65(1H,d,J=5.1 Hz), 9.16(1H,d,J=1.3 Hz).

WORKING EXAMPLE 8-2

Sodium (4R,5S,6S)-6-[(1R)-1-hydroxyethyl]-4-methyl-7-oxo-3-[2-(4-pyrimidinyl)ethylthio]-1-azabicyclo[3.2.0] hept-2-ene-2-carboxylate The compound (600 mg) produced by the method of Working Example 8-1 was subjected to the same reaction and purification procedure as in Working Example 1-2 to afford the title compound (98 mg).

IR(KBr): 1749, 1589, 1394 cm$^{-1}$. $^1$H-NMR(D$_2$O)δ: 1.14 (3H,d,J=7.4 Hz), 1.29(3H,d,J=6.3 Hz), 3.0–3.4(5H,m), 3.39 (1H,dd,J=2.5,6.3 Hz), 3.98(1H,dd,J=2.5,9.2 Hz), 4.23(1H, dq,J=6.3,6.3 Hz), 7.52(1H,dd,J=1.1,5.3 Hz), 8.68(1H,d,J= 5.3 Hz), 9.07(1H,d,J=1.1 Hz).

WORKING EXAMPLE 9

Sodium (4R,5S,6S)-3-[2-(2-amino-4-thiazolyl)ethylthio]-6-[(1R)-1-hydroxyethyl]-4-methyl-7-oxo-1-azabicyclo[3.2.0]hept-2-ene-2-carboxylate Employing 4-(2-acetylthioethyl)-2-thiazolylamine (900 mg) in place of 4-(2-acetylthioethyl)pyrimidine, the same reaction and purification procedure as in Working Example 8-1 was conducted. The resultant compound was subjected to the same reaction and purification procedure as in Working Example 1-2 to afford the title compound (113 mg).

IR(KBr): 1740, 1590, 1520 cm$^{-1}$. $^1$H-NMR(D$_2$O)δ: 1.12 (3H,d,J=7 Hz), 1.29(3H,d,J=6 Hz), 2.7–3.3(5H,m), 3.37(1H, dd,J=3, 6 Hz), 4.06(1H,dd,J=3, 9 Hz), 4.1–4.3(1H,m), 6.37 (1H,s).

WORKING EXAMPLE 10-1

4-Nitrobenzyl (4R,5S,6S)-6-[(1R)-1-hydroxyethyl]-3-[1-(tert-butyldimethylsilyloxymethyl)-2-(2-pyridyl)ethylthio]-4-methyl-7-oxo-1-azabicyclo[3.2.0]hept-2-ene-2-carboxylate 1-(Tert-butyldimethylsilyloxy)-3-(2-pyridyl)-2-propanol (641 mg) was subjected to the same reaction and purification procedure as in Working Example 1-1 to afford diastereomer-1 (339 mg) and diastereomer-2 (339 mg) of the title compound, respectively.

Diastereomer-1

$^1$H-NMR(CDCl$_3$)δ: 0.04(6H,s), 0.88(9H,s), 0.99(3H,d,J= 7.4 Hz), 1.34(3H,d,J=6.2 Hz), 2.6–2.8(1H,m), 3.20(1H,dd, J=2.6,6.8 Hz), 3.2–3.4(1H,m), 3.4–3.6(1H,m), 3.6–3.9(2H, m), 3.8–3.95(1H,m), 4.1–4.2(1H,m), 4.2–4.3(1H,m), 5.21 (1H,d,J=13.9 Hz), 5.48(1H,d,J=13.9 Hz), 7.1–7.25(2H,m), 7.45–7.55(1H,m), 7.65(2H,d,J=8.7 Hz), 8.21(2H,d,J=8.7 Hz), 8.5–8.6(1H,m).

Diastereomer-2

$^1$H-NMR(CDCl$_3$)δ: 0.05(6H,s), 0.89(9H,s), 1.20(3H,d,J= 7.2 Hz), 1.33(3H,d,J=6.2 Hz), 2.8–3.0(1H,m), 3.19(1H,dd, J=2.6,6.4 Hz), 3.15–3.35(1H,m), 3.40(1H,dd,J=7.2,9.4 Hz), 3.7–3.9(3H,m), 3.89(1H,dd,J=2.6,9.4 Hz), 4.1–4.3(1H,m), 5.21(1H,d,J=13.7 Hz), 5.51(1H,d,J=13.7 Hz), 7.1–7.2(2H, m), 7.45–7.55(1H,m), 7.66(2H,d,J=8.9 Hz), 8.23(2H,d,J= 8.9 Hz), 8.5–8.6(1H,m).

WORKING EXAMPLE 10-2

Sodium (4R,5S,6S)-6-[(1R)-1-hydroxyethyl]-3-[1-hydroxymethyl-2-(2-pyridyl)ethylthio]-4-methyl-7-oxo-1-azabicyclo[3.2.0]hept-2-ene-2-carboxylate Diastereomer-1 (339 mg) of the compound produced by the method of Working Example 10-1 was dissolved in acetonitrile (5 ml). To the solution were added acetic acid (0.09 ml) and tetrabutylammonium fluoride (IM THF solution, 1.1 ml). The mixture was stirred for 7 hours at 25° C. The reaction mixture was concentrated, which was diluted with ethyl acetate, and washed with water, an aqueous solution of sodium hydrogencarbonate and an aqueous saline solution, successively. The solution was dried over anhydrous magnesium sulfate, which was concentrated. The concentrate was dissolved in a mixture of THF (20 ml) and a phosphate buffer solution (pH 7, 0.1M, 20 ml). To the solution was added 10% palladium carbon (0.40 g), and the mixture was stirred for one hour at room temperature under hydrogen atmosphere. The catalyst was filtered off and washed with water sufficiently. The filtrate was washed with diethyl ether (40 ml). The aqueous layer was concentrated under reduced pressure, which was purified by means of a column chromatography (carrier: HP20SS, 50 ml, developing solvent: 10% aqueous solution of acetonitrile), followed by freeze-drying to afford diastereomer-1 (118 mg) of the title compound. Diastereomer-2 (339 mg) of the compound produced by the method of Working Example 10-1 was also subjected to the same reaction and purification procedure to afford diastereomer-2 (83 mg) of the title compound.

Diastereomer-1

IR(KBr): 1747, 1593 cm$^{-1}$. $^1$H-NMR(D$_2$O)δ: 0.81(3H,d, J=7.0 Hz), 1.27(3H,d,J=6.6 Hz), 2.7–2.9(1H,m), 3.2–3.4 (3H,m), 3.5–3.65(1H,m), 3.78(2H,d,J=5.6 Hz), 4.15(1H,dd, J=2.6,9.4 Hz), 4.1–4.3(1H,m), 7.3–7.5(2H,m), 7.8–7.9(1H, m), 8.45–8.55 (1H,m).

Diastereomer-2

IR(KBr): 1747, 1593 cm$^{-1}$. $^1$H-NMR(D$_2$O)δ: 1.04(3H,d, J=7.4 Hz), 1.24(3H,d,J=6.2 Hz), 2.8–3.0(2H,m), 3.2–3.4 (2H,m), 3.56(1H,dd,J=2.6,9.4 Hz), 3.5–3.7(1H,m), 3.77(1H, dd,J=7.1,12.0 Hz), 3.94(1H,dd,J=4.6,12.0 Hz), 4.1–4.25 (1H,m), 7.3–7.4(2H,m), 7.7–7.8(1H,m), 8.45–8.55(1H,m).

WORKING EXAMPLE 11-1

4-Nitrobenzyl (4R,5S,6S)-3-[1-(tert-butyldimethylsilyloxymethyl)-2-(2-thiazolyl)ethylthio]-6-[(1R)-1-hydroxyethyl]-4-methyl-7-oxo-1-azabicyclo[3.2.0]hept-2-ene-2-carboxylate Employing 1-(tert-butyldimethylsilyloxy)-3-(2-thiazolyl)-2-propanol, the same reaction and purification procedure as in Working Example 10-1 was conducted to afford diastereomer-1 and diastereomer-2 of the title compound, respectively.

Diastereomer-1

$^1$H-NMR(CDCl$_3$)δ: 0.04(6H,s), 0.88(9H,s), 1.12(3H,d,J= 7.4 Hz), 1.35(3H,d,J=6.6 Hz), 2.95–3.15(1H,m), 3.25(1H, dd,J=2.6,6.6 Hz), 3.4–3.9(5H,m), 4.15–4.35(1H,m), 4.21 (1H,dd,J=2.6,9.3 Hz), 5.23(1H,d,J=13.9 Hz), 5.49(1H,d,J= 13.9 Hz), 7.24(1H,d,J=3.4 Hz), 7.65(2H,d,J=8.9 Hz), 7.73 (1H,d,J=3.4 Hz), 8.21(2H,d,J=8.9 Hz).

Diastereomer-2

$^1$H-NMR(CDCl$_3$)δ: 0.06(6H,s), 0.90(9H,s), 1.21(3H,d,J= 7.6 Hz), 1.33(3H,d,J=6.5 Hz), 3.1–4.0(6H,m), 3.23(1H,dd, J=2.6,6.5 Hz), 4.08(1H,dd,J=2.6,9.4 Hz), 4.15–4.35(1H,m), 5.23(1H,d,J=13.8 Hz), 5.51(1H,d,J=13.8 Hz), 7.22(1H,d,J= 3.2 Hz), 7.66(2H,d,J=8.9 Hz), 7.74(1H,d,J=3.2 Hz), 8.22 (2H,d,J=8.9 Hz).

WORKING EXAMPLE 11-2

Sodium (4R,5S,6S)-3-[1-hydroxymethyl-2-(2-thiazolyl)ethylthio]-6-[(1R)-1-hydroxyethyl]-4-methyl-7-oxo-1-azabicyclo[3.2.0]hept-2-ene-2-carboxylate Diastereomer-1 and diastereomer-2 of the compound produced by the method of Working Example 11-1 were respectively subjected to the same reaction and purification procedure as in Working. Example 10-2 to afford diastereomer-1 and diastereomer-2 of the title compound, respectively.

Diastereomer-1

IR(KBr): 1751, 1597, 1396 cm$^{-1}$. $^1$H-NMR(D$_2$O)δ: 0.95 (3H,d,J=7.0 Hz), 1.28(3H,d,J=6.2 Hz), 3.1–3.85(6H,m), 3.38(1H,dd,J=2.2,6.2 Hz), 4.18(1H,dd,J=2.2,9.0 Hz), 4.23 (1H,dq,J=6.2,6.2 Hz), 7.52(1H,d,J=3.5 Hz), 7.75(1H,d,J= 3.5 Hz).

Diastereomer-2

IR(KBr): 1749, 1601, 1396 cm$^{-1}$. $^1$H-NMR(D$_2$O)δ: 1.09 (3H,d,J=7.4 Hz), 1.27(3H,d,J=6.3 Hz), 3.0–4.0(6H,m), 3.33

(1H,dd,J=2.5,6.3 Hz), 3.84(1H,dd,J=2.5,9.5 Hz), 4.19(1H, dq,J=6.3,6.3 Hz), 7.47(1H,d,J=3.5 Hz), 7.77(1H,d,J=3.5 Hz).

WORKING EXAMPLE 12-1
4-Nitrobenzyl (4R,5S,6S)-6-[(1R)-1-hydroxyethyl]-3-[(1R)-1-methoxymethyl-2-(3-pyrazolyl)ethylthio]-4-methyl-7-oxo-1-azabicyclo[3.2.0]hept-2-ene-2-carboxylate The same reaction and purification as in Working Example 7-1 were conducted, employing (R)-1-methoxy-3-(3-pyrazolyl)-2-propanethiol (352 mg) in place of 2-(6-amino-2-pyridyl)ethanethiol, to afford the title compound (284 mg).

IR(neat): 1760, 1700 cm$^{-1}$. $^1$H-NMR(CDCl$_3$)δ: 1.16(3H, d,J=7.4 Hz), 1.33(3H,d,J=6.2 Hz), 2.91(1H,dd,J=7.2,14.8 Hz), 3.18(1H,dd,J=5.2,14.8 Hz), 3.21(1H,dd,J=2.6,6.2 Hz), 3.25(1H,dq,J=9.0,7.4 Hz), 3.40(3H,s), 3.57(2H,s), 3.5–3.65 (1H,m), 4.03(1H,dd,J=2.6,9.0 Hz), 4.24(1H,dq,J=6.2,6.2 Hz), 5.24(1H,d,J=13.8 Hz), 5.50(1H,d,J=13.8 Hz), 6.10(1H, d,J=2.2 Hz), 7.45(1H,d,J=2.2 Hz), 7.66(2H,d,J=8.8 Hz), 8.22(2H,d,J=8.8 Hz).

WORKING EXAMPLE 12-2
Sodium (4R,5S,6S)-6-[(1R)-1-hydroxyethyl]-3-[(1R)-1-methoxymethyl-2-(3-pyrazolyl)ethylthio]-4-methyl-7-oxo-1-azabicyclo[3.2.0]hept-2-ene-2-carboxylate The compound produced by the method of Working Example 12-1 (284 mg) was subjected to the same reaction and purification as in Working Example 1-2 to afford the title compound (130 mg).

IR(KBr): 1745, 1590, 1390 cm$^{-1}$. $^1$H-NMR(D$_2$O)δ: 1.08 (3H,d,J=7.4 Hz), 1.26(3H,d,J=6.2 Hz), 2.87(1H,dd,J=7.6, 15.0 Hz), 3.11(1H,dd,J=5.4,15.0 Hz), 3.0–3.2(1H,m), 3.32 (1H,dd,J=2.6,6.2 Hz), 3.41(3H,s), 3.45–3.8(3H,m), 3.85 (1H,dd,J=2.2,9.4 Hz), 4.19(1H,dq,J=6.2,6.2 Hz), 6.25(1H, d,J=1.8 Hz), 7.59(1H,d,J=1.8 Hz).

WORKING EXAMPLE 13-1
4-Nitrobenzyl (4R,5S,6S)-6-[(1R)-1-hydroxyethyl]-4-methyl-7-oxo-3-[2-(1H-1,2,4-triazol-3-yl)ethylthio]-1-azabicyclo[3.2.0]hept-2-ene-2-carboxylate The same reaction and purification as in Working Example 8-1 were conducted, employing 3-(2-acetylthioethyl)-1H-1,2,4-triazole (134 mg), to afford the title compound (31 mg).

$^1$H-NMR(CDCl$_3$)δ: 1.21(3H,d,J=7.2 Hz), 1.33(3H,d,J=6.4 Hz), 3.05–3.4(4H,m), 3.27(1H,dd,J=2.6,5.8 Hz), 3.37 (1H,dq,J=9.2,7.2 Hz), 4.17(1H,dd,J=2.6,8.8 Hz), 4.29(1H, dq,J=5.8,6.4 Hz), 5.21(1H,d,J=14.0 Hz), 5.45(1H,d,J=14.0 Hz), 7.62(2H,d,J=8.8 Hz), 8.11(1H,s), 8.20(2H,d,J=8.8 Hz).

WORKING EXAMPLE 13-2
Sodium (4R,5S,6S)-6-[(1R)-1-hydroxyethyl]-4-methyl-7-oxo-3-[2-(1H-1,2,4-triazol-3-yl)ethylthio]-1-azabicyclo[3.2.0]hept-2-ene-2-carboxylate The compound produced by the method of Working Example 13-1 (31 mg) was subjected to the same reaction and purification as in Working Example 1-2 to afford the title compound (9 mg).

$^1$H-NMR(D$_2$O)δ: 1.13(3H,d,J=7.2 Hz), 1.28(3H,d,J=6.2 Hz), 3.0–3.4(5H,m), 3.37(1H,dd,J=2.6,6.4 Hz), 4.02(1H,dd, J=2.6,8.8 Hz), 4.23(1H,dq,J=6.4,6.2 Hz), 8.26(1H,s).

WORKING EXAMPLE 14-1
4-Nitrobenzyl (4R,5S,6S)-6-[(1R)-1-hydroxyethyl]-3-[2-(4-imidazolyl)ethylthio]-4-methyl-7-oxo-1-azabicyclo[3.2.0]hept-2-ene-carboxylate 2-(4-Imidazolyl)ethanethiol (385 mg) was subjected to the same reaction and purification as in Working Example 7-1 to afford the title compound (418 mg).

IR(KBr): 1765, 1705, 1521 cm$^{-1}$. $^1$H-NMR(CDCl$_3$)δ: 1.20(3H,d,J=7.2 Hz), 1.35(3H,d,J=6.4 Hz), 2.8–3.45(6H,m), 4.05–4.35(2H,m), 5.22(1H,d,J=13.8 Hz), 5.51(1H,d,J=13.8 Hz), 6.83(1H,d,J=1.1 Hz), 7.62(1H,d,J=1.1 Hz), 7.66(2H,d, J=9.0 Hz), 8.22(2H,d,J=9.0 Hz).

WORKING EXAMPLE 14-2
Sodium (4R,5S,6S)-6-[(1R)-1-hydroxyethyl]-3-[2-(4-imidazolyl)ethylthio]-4-methyl-7-oxo-1-azabicyclo[3.2.0]hept-2-ene-carboxylate The compound produced by the method of Working Example 14-1 (400 mg) was subjected to the same reaction and purification as in Working Example 1-2 to afford the title compound (127 mg).

IR(KBr): 1761, 1593 cm$^{-1}$. $^1$H-NMR(D$_2$O)δ: 1.13(3H,d, J=7.4 Hz), 1.29(3H,d,J=6.6 Hz), 2.9–3.35(5H,m), 3.38(1H, dd,J=2.4,5.9 Hz), 3.99(1H,dd,J=2.4,9.2 Hz), 4.23(1H,dq,J= 5.9,6.6 Hz), 7.07(1H,s), 8.04(1H,s).

WORKING EXAMPLE 15-1
4-Nitrobenzyl (4R,5S,6S)-6-[(1R)-1-hydroxyethyl]-4-methyl-7-oxo-3-[2-(3-pyridazinyl)ethylthio]-1-azabicyclo[3.2.0]hept-2-ene-2-carboxylate 3-($^2$-Acetylthioethyl)pyridazine (547 mg) was subjected to the same reaction and purification as in Working Example 8-1 to afford the title compound (1188 mg).

IR(KBr): 1757, 1694, 1518 cm$^{-1}$. $^1$H-NMR(CDCl$_3$)δ: 1.24(3H,d,J=7.0 Hz), 1.36(3H,d,J=6.2 Hz), 3.2–3.65(6H,m), 4.22(1H,dd,J=2.5,9.3 Hz), 4.15–4.35(1H,m), 5.22(1H,d,J= 13.8 Hz), 5.51(1H,d,J=13.8 Hz), 7.35–7.55(2H,m), 7.66(2H, d,J=8.9 Hz), 8.23(2H,d,J=8.9 Hz), 9.15(1H,d,J=4.6 Hz).

WORKING EXAMPLE 15-2
Sodium ($^4$R,5S,$^6$S)-6-[(1R)-1-hydroxyethyl]-4-methyl-7-oxo-3-[2-(3-pyridazinyl)ethylthio]-1-azabicyclo[3.2.0]hept-2-ene-2-carboxylate The compound produced by the method of Working Example 15-1 (600 mg) was subjected to the same reaction and purification as in Working Example 1-2 to afford the title compound (287 mg).

IR(KBr): 1749, 1593 cm$^{-1}$. $^1$H-NMR(D$_2$O)δ: 1.11(3H, J=7.4 Hz), 1.28(3H,d,J=6.3 Hz), 3.05–3.5(6H,m), 3.87(1H, dd,J=2.4,9.4 Hz), 4.22(1H,dq,J=6.3,6.3 Hz), 7.65–7.8(2H, m), 9.08(1H,dd,J=2.4,4.2 Hz).

WORKING EXAMPLE 16-1
4-Nitrobenzyl ($^4$R,5S,6S)-6-[(1R)-1-hydroxyethyl]-4-methyl-3-[1-methyl-2-(3-pyridazinyl)ethylthio]-7-oxo-1-azabicyclo[3.2.0]hept-2-ene-2-carboxylate 3-(2-Acetylthiopropyl)pyridazine (981 mg) was subjected to the same reaction and purification as in Working Example 8-1 to afford a mixture of diastereomers of the title compound (1342 mg). This mixture (1200 mg) was subjected to a medium-pressure column chromatography (LiChroprep RP-18: Merck & Co., eluent: acetonitrile-water=45:55) to afford diastereomer-1 (429 mg) and diastereomer-2 (616 mg) of the title compound, separately.

Diastereomer-1
IR(KBr): 1769, 1709, 1522 cm$^{-1}$. $^1$H-NMR(CDCl$_3$)δ: 1.22(3H,d,J=7.4 Hz), 1.35(3H,d,J=6.4 Hz), 1.42(3H,d,J=7.0 Hz), 3.1–3.35(3H,m), 3.45–3.7(1H,m), 3.8–4.0(1H,m), 4.07 (1H,dd,J=2.6,9.6 Hz), 4.1–4.35(1H,m); 5.21(1H,d,J=13.8 Hz), 5.50(1H,d,J=13.8 Hz), 7.3–7.5(2H,m), 7.67(2H,d,J=8.8 Hz), 8.23(2H,d,J=8.8 Hz), 9.05–9.2(1H,m).

Diastereomer-2
IR(KBr): 1771, 1709, 1522 cm$^{-1}$. $^1$H-NMR(CDCl$_3$)δ: 1.08(3H,d,J=7.2 Hz), 1.36(3H,d,J=6.2 Hz), 1.52(3H,d,J=6.6 Hz), 3.04(1H,dd,J=9.9,14.5 Hz), 3.25(1H,dd,J=2.6,6.6 Hz), 3.25–3.55(2H,m), 3.85–4.1(1H,m), 4.15–4.35(2H,m), 5.21 (1H,d,J=14.0 Hz), 5.51(1H,d,J=14.0 Hz), 7.35–7.6(2H,m), 7.66(2H,d,J=8.9 Hz), 8.22(2H,d,J=8.9 Hz), 9.13(1H,dd,J=1.9,4.7 Hz).

WORKING EXAMPLE 16-2
Sodium (4R,5S,6S)-6-[(1R)-1-hydroxyethyl]-4-methyl-3-[1-methyl-2-(3-pyridazinyl)ethylthio]-7-oxo-1-azabicyclo[3.2.0]hept-2-ene-2-carboxylate (Diastereomer-1)

Diastereomer-1 of the compound produced in Working Example 16-1 (350 mg) was subjected to the same reaction and purification as in Working Example 1-2 to afford diastereomer-1 of the title compound (219 mg).

IR(KBr): 1749, 1599 cm$^{-1}$. $^1$H-NMR(D$_2$O)δ: 1.08(3H,d,J=7.4 Hz), 1.26(3H,d,J=6.4 Hz), 1.47(3H,d,J=7.0 Hz), 2.95–3.15(2H,m), 3.32(1H,dd,J=2.5,6.4 Hz), 3.49(1H,dd,J=4.5,13.5 Hz), 3.55–3.7(2H,m), 4.19(1H,dq,J=6.4,6.4 Hz), 7.66(1H,dd,J=4,9,8.3 Hz), 7.74(1H,d,J=8.3 Hz), 9.07(1H,d,J=4.9 Hz).

WORKING EXAMPLE 17
Sodium (4R,5S,6S)-6-[(1R)-1-hydroxyethyl]-4-methyl-3-[1-methyl-2-(3-pyridazinyl)ethylthio]-7-oxo-1-azabicyclo[3.2.0]hept-2-ene-carboxylate (Diastereomer-2)

Diastereomer-2 of the compound produced in Working Example 16-1 (400 mg) was subjected to the same reaction and purification as in Working Example 1-2 to afford diastereomer-2 of the title compound (240 mg) of the title compound.

IR(KBr): 1749, 1595 cm$^{-1}$. $^1$H-NMR(D$_2$O)δ: 0.93(3H,d,J=7.2 Hz), 1.28(3H,d,J=6.6 Hz), 1.45(3H,d,J=6.6 Hz), 3.10 (1H,dd,J=10.0,14.2 Hz), 3.25–3.45(3H,m), 3.55–3.75(1H,m), 4.1–4.3(1H,m), 4.18(1H,dd,J=2.8,9.8 Hz), 7.77(1H,dd,J=4.5,8.5 Hz), 7.84(1H,dd,J=2.1,8.5 Hz), 9.09(1H,dd,J=2.1,4.5 Hz).

WORKING EXAMPLE 18-1
4-Nitrobenzyl (4R,5S,6S)-6-[(R)-1-hydroxyethyl]-3-[2-(imidazo[1,2-a]pyridin-2-yl)ethylthio]-4-methyl-7-oxo-1-azabicyclo(3.2.0]hept-2-ene-2-carboxylate The same reaction and purification as in Working Example 7-1 were conducted, employing 2-(imidazo[1,2-a]pyridin-2-yl)ethanethiol (0.78 g) in place of 2-(6-amino-2-pyridyl)ethanethiol, to afford the title compound (328 mg).

IR(neat): 1760, 1700, 1515 cm$^{-1}$. $^1$H-NMR(CDCl$_3$)δ: 1.23(3H,d,J=7.6 Hz), 1.34(3H,d,J=6.2 Hz), 3.05–3.4(5H,m), 3.46(1H,dq,J=8.6,7.6 Hz), 4.06(1H,dd,J=2.6,8.4 Hz), 4.24 (1H,dq,J=6.6,6.2 Hz), 5.22(1H,d,J=13.8 Hz), 5.52(1H,d,J=13.8 Hz), 6.7–6.85(1H,m), 7.1–7.25(1H,m), 7.41(1H,s), 7.45–7.6(1H,m), 7.66(2H,d,J=9.0 Hz), 8.0–8.1(1H,m), 8.21 (1H,d,J=9.0 Hz).

WORKING EXAMPLE 18-2
Sodium (4R,5S,6S)-6-[(R)-1-hydroxyethyl]-3-[2-(imidazo[1,2-a]pyridin-2-yl)ethylthio]-4-methyl-7-oxo-1-azabicyclo[3.2.0]hept-2-ene-2-carboxylate The compound produced by the method of Working Example 18-1 (328 mg) was subjected to the same reaction and purification as in Working Example 1-2 to afford the title compound (115 mg).

IR(KBr): 1740, 1590 cm$^{-1}$. $^1$H-NMR(D$_2$O)δ: 1.06(3H,d,J=7.4 Hz), 1.21(3H,d,J=6.6 Hz), 2.95–3.25(5H,m), 3.26(1H,dd,J=2.4,6.4 Hz), 3.45(1H,dd,J=2.4,9.0 Hz), 4.10(1H,dq,J=6.4,6.6 Hz), 6.95–7.05(1H,m), 7.35–7.6(2H,m), 7.65(1H,s), 8.3–8.4(1H,m).

WORKING EXAMPLE 19-1
4-Nitrobenzyl (4R,5S,6S)-6-[(R)-1-hydroxyethyl]-3-[2-(imidazo[1,5-a]pyrazin-3-yl)ethylthio]-4-methyl-7-oxo-1-azabicyclo[3.2.0]hept-2-ene-2-carboxylate To a solution of 3-(2-acetylthioethyl)imidazo[1,5-a]pyrazine (1.01 g) in THF-methanol (1:1, 40 ml) was added sodium methoxide (41 ml) under ice cooling. The mixture was stirred for 1.5 hour at 0° C. To the mixture were added acetic acid (2.71 ml) and acetonitrile (40 ml) in the order mentioned. The mixture was concentrated under reduced pressure to volume 5 ml. Insolubles were filtered and washed with acetonitrile (40 ml). To the filtrate were added 4-nitrobenzyl (4R,5S,6S)-3-[(diphenylphosphono)oxy-6-[(R)-hydroxyethyl]-4-methyl-7-oxo-1-azabicyclo[3.2.0) hept-2-ene-2-carboxylate (2.71 g) and diisopropylethylamine (0.95 ml) under ice cooling. The mixture was stirred over night at room temperature, to which was added ethyl acetate. The mixture was washed with saturated aqueous solution of sodium hydrogencarbonate, and dried over anhydrous magnesium sulfate. The solvent was distilled off and the residue was subjected to flash column chromatography (carrier: silica gel, 50 g, developing solvent: ethyl acetate-ethanol, 9:1→ethyl acetate-ethanol, 4:1) to give the title compound (1.67 g) as colorless solid product.

IR(KBr): 3250, 1769, 1709, 1520, 1346 cm$^{-1}$. $^1$H-NMR (CDCl$_3$) δ: 1.20(3H,d,J=7.2 Hz), 1.34(3H,d,J=6.2 Hz), 1.95–2.05(1H,m), 3.15–3.55(6H,m), 4.03(1H,dd,J=9.8,2.8 Hz), 4.15–4.35(1H,m), 5.31(2H,ABq,J=14.0 Hz), 7.49(1H,d,J=5.0 Hz), 7.55–7.70(1H,m), 7.64(2H,d,J=8.8 Hz), 7.78 (1H,s), 8.21(2H,d,J=8.8 Hz), 8.92(1H,d,J=1.4 Hz).

WORKING EXAMPLE 19-2
Sodium (4R,5S,6S)-6-[(R)-1-hydroxyethyl]-3-[2-(imidazo[1,5-a]pyrazin-3-yl)ethylthio]-4-methyl-7-oxo-1-azabicyclo(3.2.0]hept-2-ene-2-carboxylate 4-Nitrobenzyl (4R,5S,6S)-6-[(R)-1-hydroxyethyl]-3-[2-(imidazo[1,5-a]pyrazin-3-yl)ethylthio]-4-methyl-7-oxo-1-azabicyclo[3.2.0]hept-2-ene-2-carboxylate (550 mg) produced in Working Example 19-1 was dissolved in a mixed solution of tetrahydrofuran (20 ml) and 0.2N-phosphate buffer solution (pH 7.0, 20 ml). To the solution was added 10% paradium carbon (280 mg). The mixture was stirred for 2 hours at room temperature under hydrogen atmosphere. The catalyst was filtered off and washed with water. The filtrate was washed with ethyl acetate. The aqueous layer was concentrated under reduced pressure. The residue was subjected to column chromatography (carrier: CHP-20P, 150 ml, developing solvent: water→5% ethanol→10% ethanol). The eluate was freeze-dried to give the title compound (273 mg) as colorless solid product.

IR(KBr): 3300, 1752, 1593, 1397 cm$^{-1}$. $^1$H-NMR(D$_2$O) δ: 1.00(3H,d,J=7.0 Hz), 1.24(3H,d,J=6.2 Hz), 2.60–2.85(1H,m), 3.10–3.60(6H,m), 4.05–4.25(1H,m), 7.42(1H,d,J=5.2 Hz), 7.95(1H,s), 8.08(1H,d,J=5.2 Hz), 8.93(1H,s).

WORKING EXAMPLE 20-1
4-Nitrobenzyl (4R,5S,6S)-6-[(R)-1-hydroxyethyl]-3-(2-(imidazo[1,5-a]pyridin-3-yl)ethylthio-4-methyl-7-oxo-1-azabicyclo[3.2.0]hept-2-ene-2-carboxylate The same reaction and purification as in Working Example 7-1 were conducted, employing 2-(imidazo[1,5-a]pyridin-3-yl)ethanethiol (0.46 g) in place of 2-(6-amino-2-pyridyl)ethanethiol, to afford the title compound (698 mg).

IR(neat): 1760, 1700, 1515 cm$^{-1}$. $^1$H-NMR(CDCl$_3$)δ: 1.18(3H,d,J=7.4 Hz), 1.33(3H,d,J=6.2 Hz), 3.15–3.5(6H,m), 3.99(1H,dd,J=2.6,9.4 Hz), 4.24(1H,dq,J=6.4,6.2 Hz), 5.19 (1H,d,J=14.0 Hz), 5.48(1H,d,J=14.0 Hz), 6.45–6.7(2H,m), 7.37(1H,s), 7.35–7.45(1H,m), 7.65(2H,d,J=8.8 Hz), 7.7–7.85(1H,m), 8.22(2H,d,J=8.8 Hz).

WORKING EXAMPLE 20-2
Sodium (4R,5S,6S)-6-[(R)-1-hydroxyethyl]-3-[2-(imidazo[1,5-a]pyridin-3-yl)ethylthio]-4-methyl-7-oxo-1-azabicyclo[3.2.0]hept-2-ene-2-carboxylate The compound produced by the method of Working Example 20-1 (698 mg) was subjected to the same reaction and purification as in Working Example 1-2 to afford the title compound (159 mg).

IR(KBr): 1745, 1590, 1390 cm$^{-1}$. $^{1}$H-NMR(D$_2$O)δ: 0.95 (3H,d,J=7.0 Hz), 1.22(3H,d,J=6.6 Hz), 2.44(1H,dq,J=9.0, 7.0 Hz), 3.1–3.6(6H,m), 4.11(1H,dq,J=5.8,6.6 Hz), 6.6–6.9 (2H,m), 7.46(1H,s), 7.45–7.55(1H,m), 8.05–8.15(1H,m).

WORKING EXAMPLE 21-1

4-Nitrobenzyl (4R,5S,6S)-6-[(1R)-1-hydroxyethyl]-3-[2-(imidazo[1,2-b]pyridazin-2-yl)ethylthio]-4-methyl-7-oxo-1-azabicyclo[3.2.0]hept-2-ene-2-carboxylate The compound produced in Reference Example 18-2 (1.11 g) was dissolved in methanol (12 ml), to which was added, at 0° C., a solution of sodium methoxide (0.27 g) in methanol (5 ml). The mixture was stirred for 30 minutes at the same temperature. To the reaction mixture was added 1N HCl (5 ml), which was then concentrated under reduced pressure. The concentrate was subjected to extraction with ethyl acetate-tetrahydrofuran (1:1). The extract was dried over anhydrous magnesium sulfate and, then, concentrated. The concentrate and 4-nitrobenzyl (4R,5S,6S)-3-[(diphenylphosphono)oxy]-6-[(1R)-1-hydroxyethyl]-4-methyl-7-oxo-1-azabicyclo[3.2.0] hept-2-ene-2-carboxylate (2.97 g) were dissolved in dimethylformamide (15 ml). To the solution was added diisopropyl ethylamine (0.87 ml). The mixture was stirred for 18 hours at 25° C. and, then, for 2 hours at 50° C. The reaction mixture was diluted with ethyl acetate, which was washed with water four times and once with a saturated aqueous saline solution, followed by drying over anhydrous magnesium sulfate and concentration. The concentrate was purified by means of a column chromatography (carrier: silica gel, developing solvent: ethyl acetate-ethanol, 9:1) to afford the title compound (1.00 g).

IR(KBr): 1763, 1707, 1524, 1343, 1209, 1138, 795 cm$^{-1}$. $^{1}$H-NMR(CDCl$_3$)δ: 1.26(3H,d,J=7.2 Hz), 1.36(3H,d,J=6.2 Hz), 3.12–3.55(6H,m), 4.07–4.31(2H,m), 5.13(1H,d,J=13.8 Hz), 5.51(1H,d,J=13.8 Hz), 7.03(1H,dd,J=9.2,4.6 Hz), 7.65 (2H,d,J=9.0 Hz), 7.82(1H,s), 7.87(1H,dd,J=9.2,1.6 Hz), 8.21(2H,d,J=9.0 Hz), 8.29(1H,dd,J=4.6,1.6 Hz).

WORKING EXAMPLE 21-2

Sodium (4R,5S,6S)-6-[(1R)-1-hydroxyethyl]-3-[2-(imidazo[1,2-b]pyridazin-2-yl)ethylthio]-4-methyl-7-oxo-1-azabicyclo[3.2.0]hept-2-ene-2-carboxylate The compound produced in Working Example 21-1 (0.60 g) was dissolved in a mixture of tetrahydrofuran (25 ml) and a 0.2M phosphate buffer solution (pH 7, 25 ml). To the solution was added 10% palladium carbon (0.61 g). The mixture was stirred for 1.5 hour at 25° C. under hydrogen atmosphere. The catalyst was filtered off and washed with water sufficiently. The filtrate was concentrated, which was washed twice with ethyl acetate. The aqueous layer was concentrated and purified by means of a column chromatography (carrier: CHP-20P, developing solvent: 5% aqueous solution of acetonitrile). The object fraction was freeze-dried to afford the title compound (0.25 g).

IR(KBr): 3360, 1752, 1591, 1397, 795 cm$^{-1}$. $^{1}$H-NMR (D$_2$O)δ: 1.09(3H,d,J=7.2 Hz), 1.24(3H,d,J=6.2 Hz), 3.07–3.33(5H,m), 3.30(1H,dd,J=6.2,2.4 Hz), 3.65(1H,dd,J=9.2,2.4 Hz), 4.15(1H,quint,J=6.2 Hz), 7.29(1H,dd,J=9.3,4.7 Hz), 7.98(1H,s), 8.01(1H,dd,J=9.3,1.5 Hz), 8.45(1H,dd,J=4.7,1.5 Hz). Elemental Analysis for C$_{18}$H$_{19}$N$_4$NaO$_4$S·1.5H$_2$O: Calcd.: C, 49.42; H, 5.07; N, 12.81. Found : C, 49.63; H, 5.37; N, 12.93.

WORKING EXAMPLE 22-1

4-Nitrobenzyl (4R,5S,6S)-6-[(1R)-1-hydroxyethyl]-3-[2-(imidazo[2,1-b][1,3,4]thiadiazol-6-yl)ethylthio]-4-methyl-7-oxo-1-azabicyclo[3.2.0]hept-2-ene-2-carboxylate Employing the compound produced in Reference Example 19-3, the same reaction and purification as in Working Example 21-1 was conducted to afford the title compound.

IR(KBr): 1765, 1701, 1518, 1342, 1209, 1138, 862 cm$^{-1}$. $^{1}$H-NMR(CDCl$_3$)δ: 1.26(3H,d,J=7.2 Hz), 1.36(3H,d,J=6.2 Hz), 2.98–3.35(5H,m), 3.41–3.56(1H,m), 4.15(1H,dd,J=9.0, 2.4 Hz), 4.20–4.30(1H,m), 5.23(1H,d,J=14.0 Hz), 5.51(1H, d,J=14.0 Hz), 7.63(1H,s), 7.66(2H,d,J=8.8 Hz), 8.22(2H,d, J=8.8 Hz), 8.51(1H,s).

WORKING EXAMPLE 22-2

Sodium (4R,5S,6S)-6-[(1R)-1-hydroxyethyl]-3-[2-(imidazo[2,1-b][1,3,4]thiadiazol-6-yl)ethylthio]-4-methyl-7-oxo-1-azabicyclo[3.2.0]hept-2-ene-2-carboxylate Employing the compound produced in Working Example 22-1, the same reaction and purification as in Working Example 21-2 were conducted to afford the title compound.

IR(KBr): 3340, 1746, 1591, 1397, 864 cm$^{-1}$. $^{1}$H-NMR (D$_2$O)δ: 1.11(3H,d,J=7.2 Hz), 1.27(3H,d,J=6.2 Hz), 2.97–3.35(6H,m), 3.81(1H,dd,J=9.2,1.4 Hz), 4.19(1H,quint, J=6.2 Hz), 7.81(1H,s), 8.93(1H,s). Elemental Analysis for C$_{16}$H$_{17}$N$_4$NaO$_4$S$_2$·1.5H$_2$O: Calcd.: C, 43.33; H, 4.55; N, 12.63. Found : C, 43.50; H, 4.33; N, 12.54.

WORKING EXAMPLE 23-1

4-Nitrobenzyl (4R,5S,6S)-3-[2-(5-aminoimidazo[1,2-a]pyridin-2-yl)ethylthio]-6-[(1R)-1-hydroxyethyl]-4-methyl-7-oxo-1-azabicyclo[3.2.0]hept-2-ene-2-carboxylate Employing the compound produced in Reference Example 20-3, the same reaction and purification as in Working Example 21-1 were conducted to afford the title compound.

IR(KBr): 3347, 3148, 1763, 1701, 1512, 1343, 1140, 735 cm$^{-1}$. $^{1}$H-NMR(CDCl$_3$+DMSO-d$_6$)δ: 1.22(3H,d,J=7.4 Hz), 1.32(3H,d, J=7.2 Hz), 3.06–3.55(6H,m), 4.10(1H,dd,J=9.2, 2.4 Hz), 4.06–4.22(1H,m), 5.18(2H,brs), 5.22(1H,d, J=14.0 Hz), 5.50(1H,d,J=14.0 Hz), 6.05(1H,d,J=7.2, 1.0 Hz), 6.98 (1H,dd,J=8.8,1.0 Hz), 7.12(1H,dd,J=8.8, 7.2 Hz), 7.40(1H, s), 7.66(2H,d,J=8.8 Hz), 8.19(2H,d,J=8.8 Hz).

WORKING EXAMPLE 23-2

Sodium (4R,5S,6S)-3-[2-(5-aminoimidazo[1,2-a]pyridin-2-yl)ethylthio]-6-[(1R)-1-hydroxyethyl]-4-methyl-7-oxo-1-azabicyclo[3.2.0]hept-2-ene-2-carboxylate Employing the compound produced in Working Example 23-1, the same reaction and purification as in Working Example 21-2 were conducted to afford the title compound.

IR(KBr): 3320, 3198, 1744, 1590, 1395, 774 cm$^{1}$. $^{1}$H-NMR(D$_2$O)δ: 1.06(3H,d,J=7.4 Hz), 1.20(3H,d,J=6.2 Hz), 3.00–3.30(6H,m), 3.43(1H,dd,J=9.0,2.4 Hz), 4.10(1H, quint,J=6.2 Hz), 6.34(1H,d,J=7.6 Hz), 7.02(1H,d,J=8.8 Hz), 7.41(1H,dd,J=8.8,7.6 Hz), 7.50(1H,s).

WORKING EXAMPLE 24-1

4-Nitrobenzyl (4R,5S,6S)-6-[(1R)-1-hydroxyethyl]-3-[2-(imidazo[1,2-a]pyridin-5-yl)ethylthio]-4-methyl-7-oxo-1-azabicyclo[3.2.0]hept-2-ene-2-carboxylate Employing the compound produced in Reference Example 21, the same reaction and purification as in Working Example 21-1 to afford the title compound.

IR(KBr): 1767, 1705, 1518, 1345, 1209, 1138, 739 cm$^{-1}$. $^{1}$H-NMR(CDCl$_3$)δ: 1.18(3H,d,J=7.4 Hz), 1.34(3H,d,J=6.2 Hz), 2.99–3.36(6H,M), 4.00(1H,d,J=9.4,1.4 Hz), 4.24(1H, quint,J=6.2 Hz), 5.23(1H,d,J=13.4 Hz), 5.51(1H,d,J=13.4 Hz), 6.68(1H,d,J=7.0 Hz), 7.15(1H,dd,J=9.2,7.0 Hz), 7.54–7.72(5H,m), 8.21(2H,d,J=8.6 Hz).

WORKING EXAMPLE 24-2

Sodium (4R,5S,6S)-6-[(1R)-1-hydroxyethyl]-3-[2-(imidazo[1,2-a]pyridin-5-yl)ethylthio]-4-methyl-7-oxo-1-azabicyclo[3.2.0]hept-2-ene-2-carboxylate Employing the compound produced in Working Example 24-1, the same reaction and purification as in Working Example 21-2 were conducted to afford the title compound.

IR(KBr): 1752, 1595, 1397, 1298, 1148, 783 cm$^{-1}$.
$^1$H-NMR(D$_2$O) δ: 0.97(3H,d,J=7.2 Hz), 1.22(3H,d,J=6.2 Hz), 2.59(1H,quint,J=7.2 Hz), 3.11–3.54(6H,m), 4.14(1H, quint,J=6.2 Hz), 6.95(1H,d,J=7.0 Hz), 7.39(1H,dd,J=9.0,7.0 Hz), 7.57(1H,d,J=9.0 Hz), 7.72(1H,s), 7.96(1H,s). Elemental Analysis for C$_{19}$H$_{20}$N$_3$NaO$_4$S·1.5H$_2$O: Calcd.: C, 52.29; H, 5.31; N, 9.63. Found :C, 52.27; H, 5.23; N, 9.34.

WORKING EXAMPLE 25-1
4-Nitrobenzyl (4R,5S,6S)-6-[(1R)-1-hydroxyethyl]-3-[2-(imidazo[1,2-a]pyrazin-2-yl)ethylthio]-4-methyl-7-oxo-1-azabicyclo[3.2.0]hept-2-ene-2-carboxylate Employing the compound produced in Reference Example 22-3, the same reaction and purification as in Working Example 21-1 were conducted to afford the title compound.

IR(KBr): 1736, 1705, 1526, 1333, 1154 cm$^{-1}$. $^1$H-NMR (CDCl$_3$)δ: 1.25(3H,d,J=7.4 Hz), 1.35(3H,d,J=6.2 Hz), 3.13–3.56(6H,m), 4.10–4.29(2H,m), 5.21(1H,d,J=13.8 Hz), 5.50(1H,d,J=13.8 Hz), 7.53(1H,s), 7.65(2H,d,J=8.8 Hz), 7.87(1H,d,J=4.8 Hz), 8.00(1H,d,J=4.8 Hz), 8.21(2H,d,J=8.8 Hz), 9.02(1H,s).

WORKING EXAMPLE 25-2
Sodium (4R,5S,6S)-6-[(1R)-1-hydroxyethyl]-3-[2-(imidazo[1,2-a]pyrazin-2-yl)ethylthio]-4-methyl-7-oxo-1-azabicyclo[3.2.0]hept-2-ene-2-carboxylate Employing the compound produced in Working Example 25-1, the same reaction and purification as in Working Example 21-2 were conducted to afford the title compound.

IR(KBr): 3360, 1744, 1593, 1397, 1292, 812 cm$^{-1}$.
$^1$H-NMR(D$_2$O)δ: 1.08(3H,d,J=7.2 Hz), 1.22(3H,d,J=6.2 Hz), 3.05–3.31(6H,m), 3.55(1H,dd,J=9.2,1.8 Hz), 4.14(1H, quint,J=6.2 Hz), 7.84(1H,s), 7.85(1H,d,J=4.6 Hz), 8.37(1H, d,J=4.6 Hz), 8.93(1H,s). Elemental Analysis for C$_{18}$H$_{19}$N$_4$NaO$_4$S·1.0H$_2$O: Calcd.: C, 50.46; H, 4.94; N, 13.08. Found : C, 50.82; H, 5.33; N, 13.02.

WORKING EXAMPLE 26-1
4-Nitrobenzyl (4R,5S,6S)-6-[(1R)-1-hydroxyethyl]-3-[2-(imidazo[1,2-a]pyridin-3-yl)ethylthio]-4-methyl-7-oxo-1-azabicyclo[3.2.0]hept-2-ene-2-carboxylate Employing the compound produced in Reference Example 23-3, the same reaction and purification as in Working Example 21-1 were conducted to afford the title compound.

IR(KBr): 1767, 1705, 1520, 1345, 1209, 1136, 737 cm$^{-1}$.
$^1$H-NMR(CDCl$_3$)δ: 1.17(3H,d,J=7.2 Hz), 1.34(3H,d,J=6.2 Hz), 3.02–3.36(6H,m), 3.92(1H,dd,J=9.2,2.4 Hz), 4.22(1H, quint,J=6.2 Hz), 5.21(1H,d,J=14.0 Hz), 5.49(1H,d,J=14.0 Hz), 6.77(1H,t,J=7.0 Hz), 7.17(1H,dd,J=9.2,7.0 Hz), 7.49 (1H,s), 7.60–7.67(3H,m), 7.98(1H,d,J=7.0 Hz), 8.22(2H,d, J=8.8 Hz).

WORKING EXAMPLE 26-2
Sodium (4R,5S,6S)-6-[(1R)-1-hydroxyethyl]-3-[2-(imidazo[1,2-a]pyridin-3-yl)ethylthio]-4-methyl-7-oxo-1-azabicyclo[3.2.0]hept-2-ene-2-carboxylate Employing the compound produced in Working Example 26-1, the same reaction and purification as in Working Example 21-2 were conducted to afford the title compound.

IR(KBr): 3360, 1748, 1593, 1395, 1315, 1140 758 cm$^{-1}$.
$^1$H-NMR(D$_2$O)δ: 0.96(3H,d,J=7.2 Hz), 1.22(3H,d,J=6.6 Hz), 2.70(1H,quint,J=7.2 Hz), 3.05–3.58(6H,m), 4.11(1H, quint,J=6.6 Hz), 6.96(1H,t,J=7.0 Hz), 7.37(1H,dd,J=9.2,7.0 Hz), 7.49(1H,s), 7.57(1H,d,J=9.2 Hz), 8.39(1H,d,J=7.0 Hz). Elemental Analysis for C$_{19}$H$_{20}$N$_3$NaO$_4$S·0.5H$_2$O: Calcd.: C, 54.54; H, 5.06; N, 10.04. Found : C, 54.25; H, 5.36; N, 9.94.

WORKING EXAMPLE 27-1
4-Nitrobenzyl (4R,5S,6S)-6-[(R)-1-hydroxyethyl]-4-methyl-7-oxo-3-[2-([1,2,4]triazolo[4,3-a]pyridin-3-yl)ethylthio]-1-azabicyclo[3.2.0]hept-2-ene-2-carboxylate The same reaction and purification as in Working Example 7-1 were conducted, employing 2-([1,2,4]triazolo[4,3-a]pyridin-3-yl)ethanethiol (678 mg) in place of 2-(6-amino-2-pyridyl)ethanethiol, to afford the title compound (1.28 g).

IR(KBr): 1767, 1705, 1520 cm$^{-1}$. $^1$H-NMR(CDCl$_3$)δ: 1.17(3H,d,J=7.4 Hz), 1.33(3H,d,J=6.4 Hz), 3.19(1H,dd,J=2.4,6.8 Hz), 3.2–3.65(5H,m), 3.98(1H,dd,J=2.4,9.4 Hz), 4.1–4.3(1H,m), 5.17(1H,d,J=13.6 Hz), 5.46(1H,d,J=13.6 Hz), 6.7–6.8(1H,m), 7.15–7.25(1H,m), 7.64(2H,d,J=8.8 Hz), 7.7–7.8(1H,m), 7.9–8.0(1H,m), 8.23(2H,d,J=8.8 Hz).

WORKING EXAMPLE 27-2
Sodium (4R,5S,6S)-6-[(R)-1-hydroxyethyl]-4-methyl-7-oxo-3-[2-(1,2,4]triazolo[4,3-a]pyridin-3-yl)ethylthio]-1-azabicyclo[3.2.0]hept-2-ene-2-carboxylate The compound produced by the method described in Working Example 27-1 (1.00 g) was subjected to the same reaction and purification as in Working Example 1-2 to afford the title compound (252 mg).

IR(KBr): 1744, 1593, 1395 cm$^{-1}$. $^1$H-NMR(D$_2$O)δ: 1.00 (3H,d,J=7.0 Hz), 1.26(3H,d,J=6.2 Hz), 2.78(1H,dq,J=8.6, 7.0 Hz), 3.1–3.7(6H,m), 4.16(1H,dq,J=6.2,6.2 Hz), 6.9–7.0 (1H,m), 7.35–7.5(1H,m), 7.55–7.65(1H,m), 8.25–8.35(1H, m).

WORKING EXAMPLE 28-1
4-Nitrobenzyl (4R,5S,6S)-[(R)-1-hydroxyethyl]-4-methyl-3-[2-(3-methylimidazo[1,2-a]pyridin-2-yl)ethylthio]-7-oxo-1-azabicyclo[3.2.0]hept-2-ene-2-carboxylate The same reaction and purification as in Working Example 7-1 were conducted, employing 2-(3-methylimidazo[1,2-a]pyridin-2-yl)ethanethio (403 mg) in place of 2-(6-amino-2-pyridyl)ethanethiol, to afford the title compound (130 mg).

IR(KBr): 1770, 1525 cm$^{-1}$. $^1$H-NMR(CDCl$_3$)δ: 1.17(3H, d,J=7.4 Hz), 1.29(3H,d,J=6.2 Hz), 2.35(3H,s), 3.0–3.4(6H, m), 3.65–3.8(1H,m), 4.14(1H,dq,J=6.2,7.6 Hz), 5.22(1H,d, J=14.0 Hz), 5.50(1H,d,J=14.0 Hz), 6.75–6.9(1H,m), 7.1–7.25(1H,m), 7.5–7.6(1H,m), 7.65(2H,d,J=8.4 Hz), 7.75–7.85(1H,m), 8.21(2H,d,J=8.4 Hz).

WORKING EXAMPLE 28-2
Sodium (4R,5S,6S)-6-[(R)-1-hydroxyethyl]-4-methyl-3-[2-(3-methylimidazo[1,2-a]pyridin-2-yl)ethylthio]-7-oxo-1-azabicyclo[3.2.0]hept-2-ene-2-carboxylate The compound produced by the method described in Working Example 28-1 (130 mg) was subjected to the same reaction and purification as in Working Example 1-2 to afford the title compound (27 mg).

IR(KBr): 1752, 1591, 1393 cm$^{-1}$. $^1$H-NMR(D$_2$O)δ: 1.06 (3H,d,J=7.4 Hz), 1.18(3H,d,J=6.4 Hz), 2.45(3H,s), 2.85–3.4 (7H,m), 4.08(1H,dq,J=6.4,5.6 Hz), 7.3–7.4(1H,m), 7.7–7.8 (2H,m), 8.3–8.4(1H,m).

WORKING EXAMPLE 29-1
4-Nitrobenzyl (4R,5S,6S)-3-[2-(6-aminoimidazo[1,2-a]pyridin-2-yl)ethylthio]-6-[(1R)-1-hydroxyethyl]-4-methyl-7-oxo-1-azabicyclo[3.2.0]hept-2-ene-2-carboxylate Employing the compound produced in Reference Example 26-4; the same reaction and purification as in Working Example 21-1 were conducted to afford the title compound.

IR(KBr): 3343, 1765, 1703, 1518, 1345, 1209, 1140, 737 cm$^{-1}$. $^1$H-NMR(CDCl$_3$)δ: 1.21(3H,d,J=7.2 Hz), 1.33(3H,d, J=6.4 Hz), 3.01–3.49(8H,m), 4.03(1H,dd,J=9.0,2.4 Hz), 4.24(1H,quint,J=6.4 Hz), 5.21(1H,d,J=13.8 Hz), 5.51(1H,d, J=13.8 Hz), 6.79(1H,dd,J=9.4,2.2 Hz), 7.22(1H,s), 7.37(1H, d,J=9.4 Hz), 7.49(1H,d,J=2.2 Hz), 7.64(2H,d,J=8.8 Hz), 8.19(2H,d,J=8.8 Hz).

WORKING EXAMPLE 29-2

Sodium (4R,5S,6S)-3-[2-(6-aminoimidazo[1,2-a]pyridin-2-yl)ethylthio]-6-[(1R)-1-hydroxyethyl]-4-methyl-7-oxo-1-azabicyclo[3.2.0]hept-2-ene-carboxylate Employing the compound produced in Working Example 29-1, the same reaction and purification as in Working Example 21-2 were conducted to afford the title compound.

IR(KBr): 3318, 1748, 1590, 1397, 812 cm$^{-1}$. $^1$H-NMR (D$_2$O)δ: 1.05(3H,d,J=7.4 Hz), 1.21(3H,d,J=6.2 Hz), 2.94–3.39(7H,m), 4.11(1H,quint,J=6.2 Hz), 7.13(1H,d,J=9.4 Hz), 7.42(1H,d,J=9.4 Hz), 7.49(1H,s), 7.86(1,s).

WORKING EXAMPLE 30-1

4-Nitrobenzyl (4R,5S,6S)-3-[2-(8-aminoimidazo[1,2-a]pyridin-2-yl)ethylthio]-6-[(1R)-1-hydroxyethyl]-4-methyl-7-oxo-1-azabicyclo[3.2.0]hept-2-ene-2-carboxylate Employing the compound produced in Reference Example 27-3, the same reaction and purification as in Working Example 21-1 were conducted to afford the title compound.

IR(KBr): 3360, 1763, 1701, 1520, 1343, 1209, 1138, 735 cm$^{-1}$. $^1$H-NMR(CDCl$_3$)δ: 1.22(3H,d,J=7.2 Hz), 1.34(3H,d, J=6.2 Hz), 3.05–3.51(6H,m), 3.98(1H,dd,J=9.0,2.4 Hz), 4.14–4.25(1H,m), 4.45(2H,br), 5.21(1H,d,J=13.8 Hz), 5.51 (1H,d,J=13.8 Hz), 6.32(1H,d,J=7.0 Hz), 6.55(1H,t,J=7.0 Hz), 7.32(1H,q), 7.52(1H,d,J=7.0 Hz), 7.64(2H,d,J=8.8 Hz), 8.20(2H,d,J=8.8 Hz).

WORKING EXAMPLE 30-2

Sodium (4R,5S,6S)-3-[2-(8-aminoimidazo[1,2-a]pyridin-2-yl) ethylthio]-6-[(1R)-1-hydroxyethyl]-4-methyl-7-oxo-1-azabicyclo[3.2.0]hept-2-ene-2-carboxylate Employing the compound produced in Working Example 30-1, the same reaction and purification as in Working Example 21-2 were conducted to afford the title compound.

IR(KBr): 3420, 1746, 1590, 1395, 735 cm$^{-1}$. $^1$H-NMR (D$_2$O)δ: 1.02(3H,d,J=7.0 Hz), 1.19(3H,d,J=6.2 Hz), 2.84–3.25(7H,m), 4.07(1H,quint,J=6.2 Hz), 6.64(1H,d,J=7.4 Hz), 6.78(1H,dd,J=7.4,6.6 Hz), 7.55(1H,s), 7.82(1H,d, J=6.6 Hz).

WORKING EXAMPLE 31-1

4-Nitrobenzyl (4R,5S,6S)-[(R)-1-hydroxyethyl]-3-[2-(imidazo[5,1-b]thiazol-5-yl)ethylthio]-4-methyl-7-oxo-1-azabicyclo[3.2.0]hept-2-ene-2-carboxylate Employing 5-(2-acetylthioethyl)imidazo[5,1-b]thiazole (1082 mg), the same reaction and purification as in Working Example 8-1 were conducted to afford the title compound (739 mg).

IR(KBr): 1767, 1705, 1520 cm$^{-1}$. $^1$H-NMR(CDCl$_3$)δ: 1.16(3H,d,J=7.4 Hz), 1.33(3H,d,J=6.2 Hz), 3.0–3.5(6H,m), 3.97(1H,dd,J=2.7,9.3 Hz), 4.15–4.35(1H,m), 5.20(1H,d,J=13.7 Hz), 5.49(1H,d,J=13.7 Hz), 6.68(1H,d,J=4.4 Hz), 7.04 (1H,s), 7.26(1H,d,J=4.4 Hz), 7.66(2H,d,J=8.8 Hz), 8.22(2H, d,J=8.8 Hz).

WORKING EXAMPLE 31-2

Sodium ($^4$R,5S,6S)-6-[(R)-1-hydroxyethyl]-3-[2-(imidazo[5,1-b]thiazol-5-yl)ethylthio]-4-methyl-7-oxo-1-azabicyclo[3.2.0]hept-2-ene-2-carboxylate The compound produced by the method described in Working Example 31-1 (600 mg) was subjected to the same reaction and purification as in Working Example 1-2 to afford the title compound (224 mg).

IR(KBr): 1750, 1593 cm$^{-1}$. $^1$H-NMR(D$_2$O)δ: 1.00(3H,d, J=7.4 Hz), 1.25(3H,d,J=6.3 Hz), 2.57(1H,dq,J=7.4,9.0 Hz), 3.0–3.6(5H,m), 3.52(1H,dd,J=2.4,9.0 Hz), 4.05–4.25(1H, m), 7.03(1H,d,J=4.4 Hz), 7.17(1H,s), 7.64(1H,d,J=4.4 Hz).

WORKING EXAMPLE 32-1

4-Nitrobenzyl (4R,5S,6S)-6-[(1R)-1-hydroxyethyl]-3-[2-(imidazo[1,2-a]pyrimidin-2-yl)ethylthio]-4-methyl-7-oxo-1-azabicyclo[3.2.0]hept-2-ene-2-carboxylate Employing the compound produced in Reference Example 29-3, the same reaction and purification as in Working Example 21-1 were conducted to afford the title compound.

IR(KBr): 1765, 1701, 1518, 1345, 1211, 1140 cm$^{-1}$. $^1$H-NMR(CDCl$_3$)δ: 1.24(3H,d,J=7.0 Hz), 1.35(3H,d,J=6.2 Hz), 3.09–3.65(6H,m), 4.07–4.29(2H,m), 5.21(1H,d,J=13.6 Hz), 5.50(1H,d,J=13.6 Hz), 6.86(1H,dd,J=6.6,4.4 Hz), 7.36 (1H,s), 7.65(2H,d,J=8.8 Hz), 8.21(2H,d,J=8.8 Hz), 8.35(1H, dd,J=6.6,2.2 Hz), 8.52(1H,dd,J=4.4,2.2 Hz).

WORKING EXAMPLE 32-2

Sodium (4R,5S,6S)-6-[(1R)-1-hydroxyethyl]-3-[2-(imidazo [1,2-a]pyrimidin-2-yl)ethylthio]-4-methyl-7-oxo-1-azabicyclo[3.2.0]hept-2-ene-2-carboxylate Employing the compound produced in Working Example 32-1, the same reaction and purification as in Working Example 21-2 were conducted to afford the title compound.

IR(KBr): 3340, 1748, 1591, 1395, 772 cm$^{-1}$. $^1$H-NMR (D$_2$O)δ: 1.00(3H,d,J=7.0 Hz), 1.16(3H,d,J=6.2 Hz), 2.90–3.23(6H,m), 3.50(1H,dd,J=9.2,2.2 Hz), 4.07(1H,quint, J=6.2 Hz), 6.97(1H,dd,J=6.8,4.4 Hz), 7.50(1H,s), 8.41(1H, dd,J=4.4,2.0 Hz), 8.61(1H,dd,J=6.8,2.0 Hz).

WORKING EXAMPLE 33-1

4-Nitrobenzyl (4R,5S,6S)-6-[(1R)-1-hydroxyethyl]-4-methyl-7-oxo-3-[2-(5-ureidoimidazo[1,2-a]pyridin-2-yl) ethylthio]-1-azabicyclo[3.2.0]hept-2-ene-2-carboxylate The compound produced in Reference Example 30 (330 mg) was suspended in methanol (30 ml). To the suspension was added, at 0° C., a solution of sodium methoxide (65 mg) in methanol (5 ml). The mixture was stirred for two hours at the same temperature. The reaction mixture was concentrated, and the concentrate was washed with ethyl acetate, then, with diisopropyl ether. The resulting white solid matter was added, at 0° C., to a solution of 4-nitrobenzyl (4R,5S,6S)-3-[(diphenylphosphono)oxy]-6-[(1R)-1-hydroxyethyl]-4-methyl-7--oxo-1-azabicyclo [3.2.0] hept-2-ene-2-carboxylate (0.77 g) in dimethylformamide (6 ml). The mixture was stirred for 0.5 hour at the same temperature and, then, for one hour at room temperature. The reaction mixture was diluted with ethyl acetate, which was washed with water four times and with a saturated aqueous saline solution once, followed by drying over anhydrous magnesium sulfate and concentration. The concentrate was purified by means of a column chromatography (carrier: silica gel, developing solvent: ethyl acetate-ethanol, 4:1) to afford the title compound (209 mg).

IR(KBr): 3360, 3200, 1763, 1701, 1514, 1343, 1211, 1140, 739 cm.$^{-1}$. $^1$H-NMR(CDCl$_3$+DMSO-d$_6$)δ: 1.23(3H, d,J=7.2 Hz), 1.30(3H,d,J=6.6 Hz), 3.10–3.50(6H,m), 4.08–4.15(2H,m), 4.60–4.64(1H,m), 5.20(1H,d,J=14.0 Hz), 5.50(1H,d,J=14.0 Hz), 5.84(2H,brs), 7.19–7.27(3H,m), 7.61–7.68(3H,m), 8.19(2H,d,J=8.8 Hz), 8.72(1H,s).

WORKING EXAMPLE 33-2

Sodium (4R,5S,6S)-6-[(1R)-1-hydroxyethyl]-4-methyl-7-oxo-3-[2-(5-ureidoimidazo[1,2-a]pyridin-2-yl)ethylthio]-1-azabicyclo[3.2.0]hept-2-ene-2-carboxylate Employing the compound produced in Working Example 33-1, the same reaction and purification as in Working Example 21-2 were conducted to afford the title compound.

IR(KBr): 3350, 3200, 1752, 1586, 1512, 1397, 779 cm$^{-1}$.
$^1$H-NMR(D$_2$O)δ: 1.03(3H,d,J=7.2 Hz), 1.18(3H,d,J=6.2 Hz), 2.91–3.24(7H,m), 4.06(1H,quint,J=6.2 Hz), 6.96(1H,d, J=7.4 Hz), 7.38–7.52(2H,m), 7.56(1H,s). Elemental Analysis for C$_{20}$H$_{22}$N$_5$NaO$_5$S·2.0H$_2$O: Calcd.: C, 47.71; H, 5.20; N, 13.91. Found : C, 48.01; H, 5.09; N, 13.64

WORKING EXAMPLE 34-1

4-Nitrobenzyl (4R,5S,6S)-6-[(R)-1-hydroxyethyl]-3-[2-(imidazo[1,5-a]pyridin-1-yl)ethylthio)-4-methyl-7-oxo-1-azabicyclo[3.2.0]hept-2-ene-2-carboxylate To 1-(2-(4-methoxybenzylthio)ethyl]imidazo[1,5-a]pyridine (2.33 g) were added, under ice-cooling, trifluoroacetic acid (41 ml), anisole (6.7 ml) and trifluoromethane sulfonic acid (1.89 ml), successively. The mixture was stirred for 5 hours at room temperature. The reaction mixture was concentrated under reduced pressure. The concentrate was washed with petroleum ether, isopropyl ether and ether, successively, to which were added ethyl acetate (100 ml), sodium hydrogencarbonate (600 mg) and water (100 ml), and the mixture was stirred. The organic layer was taken, which was dried over magnesium sulfate, followed by distilling off the solvent under reduced pressure. To an acetonitrile solution (150 ml) of the residue were added, under ice-cooling, 4-nitrobenzyl (4R,5S,6S)-3-[(diphenylphosphono)oxy-6-[(R)-1-hydroxyethyl]-4-methyl-7-oxo-1-azabicyclo[3.2.0]hept-2-ene-2-carboxylate (4.24 g) and diisopropylethylamine (2.49 ml). The mixture was stirred over night at room temperature. To the reaction mixture was added ethyl acetate, which was washed with a saturated aqueous solution of sodium hydrogencarbonate, followed by drying over anhydrous magnesium sulfate. The solvent was distilled off under reduced pressure. The residue was purified by means of a flash column chromatography (carrier: silica gel, 60 g, developing solvent: ethyl acetate→ethyl acetate-ethanol, 9:1) to afford the title compound (639 mg as a colorless solid product.

IR(KBr): 1767, 1705, 1520, 1345 cm$^{-1}$. $^1$H-NMR (CDCl$_3$)δ: 1.20(3H,d,J=7.2 Hz), 1.34(3H,d,J=6.4 Hz), 3.00–3.45(6H,M), 3.95–4.10(1H,m), 4.15–4.35(1H,m), 5.34 (2H,ABq,J=14.0 Hz), 6.40–6.70(2H,m), 7.20–7.40(1H,m), 7.64(2H,d,J=8.8 Hz), 7.85(1H,d,J=7.0 Hz), 8.07(1H,s), 8.20 (2H,d,J=8.8 Hz).

WORKING EXAMPLE 34-2

Sodium (4R,5S,6S)-6-[(R)-1-hydroxyethyl]-3-[2-(imidazo[1,5-a]pyridin-1-yl)ethylthio]-4-methyl-7-oxo-1-azabicyclo[3.2.0]hept-2-ene-2-carboxylate The compound produced by the method described in Working Example 34-1 (403 mg) was dissolved in a mixture of tetrahydrofuran (15 ml) and a 0.2N-phosphate buffer solution (pH=7.0, 15 ml). To the solution was added 10% palladium carbon (400 mg). The mixture was stirred for 1.5 hour at room temperature under hydrogen atmosphere. The catalyst was filtered off and washed with water. The filtrate was then washed with ethyl acetate. The aqueous layer was concentrated under reduced pressure, which was purified by means of a column chromatography (carrier: CHP-20P, 70 ml, developing solvent: water→5% ethanol→10% ethanol), followed by freeze-drying to afford the title compound as a colorless solid product (115 mg).

IR(KBr): 3300, 1748, 1593, 1397 cm$^{-1}$. $^1$H-NMR(D$_2$O)δ: 0.96(3H,d,J=7.4 Hz), 1.23(3H,d,J=6.6 Hz), 2.40–2.60(1H, m), 3.00–3.50(6H,m), 4.12(1H,quintet, J=6.6 Hz), 6.60–6.85(2H,m), 7.50(1H,d,J=9.2 Hz), 8.11(1H,d,J=6.6 Hz), 8.42(1H,s).

WORKING EXAMPLE 35-1

4-Nitrobenzyl (4R,5S,6S)-3-[2-(3-aminoimidazo[1,2-a] pyridin-2-yl)ethylthio]-6-[(1R)-1-hydroxyethyl]-4-methyl-7-oxo-1-azabicyclo[3.2.0]hept-2-ene-2-carboxylate Employing the compound produced in Reference Example 32-4, the same reaction and purification as in Working Example 21-1 were conducted to afford the title compound.

IR(KBr): 3340, 1763, 1701, 1522, 1346, 1211, 1138, 737 cm$^{-1}$. $^1$H-NMR(CDCl$_3$)δ: 1.11(3H,d,J=7.2 Hz), 1.26(3H,d, J=6.2 Hz), 3.03–3.45(9H,m), 4.06–4.14(1H,m), 5.24(1H,d, J=13.8 Hz), 5.51(1H,d,J=13.8 Hz), 6.81(1H,t,J=7.0 Hz), 7.12(1H,dd, J=9.2,7.0 Hz), 7.47(1H,d,J=9.2 Hz), 7.66(2H, d,J=8.8 Hz), 7.96(1H,d,J=7.0 Hz), 8.22(2H,d,J=8.8 Hz).

WORKING EXAMPLE 35-2

Sodium (4R,5S,6S)-3-[2-(3-aminoimidazo[1,2-a]pyridin-2-yl)ethylthio]-6-[(1R)-1-hydroxyethyl]-4-methyl-7-oxo-1-azabicyclo[3.2.0]hept-2-ene-2-carboxylate Employing the compound produced in Working Example 35-1, the same reaction and purification as in Working Example 21-2 were conducted to afford the title compound.

IR(KBr): 3320, 1748, 1590, 1395, 752 cm$^{-1}$. $^1$H-NMR (D$_2$O)δ: 1.00(3H,d,J=7.0 Hz), 1.15(3H,d,J=6.2 Hz), 2.83 (1H,quint,J=7.0 Hz), 2.96–3.26(6H,m), 4.03(1H,quint,J=6.2 Hz), 7.06(1H,t,J=7.0 Hz), 7.38(1H,dd,J=9.2,7.0 Hz), 7.52 (1H,d,J=9.2 Hz), 8.12(1H,d,J=7.0 Hz). Elemental Analysis for C$_{19}$H$_{21}$N$_4$NaO$_4$S·2.5H$_2$O: Calcd.: C, 48.61; H, 5.58; N, 11.93. Found : C, 48.91; H, 5.28; N, 12.00.

WORKING EXAMPLE 36-1

4-Nitrobenzyl (4R,5S,6S)-6-[(R)-1-hydroxyethyl]-3-[2-(isoquinolin-1-yl )ethylthio]-4-methyl-7-oxo-1-azabicyclo [3.2.0]hept-2-ene-2-carboxylate Employing the compound produced in Reference Example 33-2, the same reaction and purification as in Working Example 21-1 were conducted to give the title compound.

IR(KBr): 1771, 1717, 1520, 1343, 1211, 1142 cm$^{-1}$. $^1$H-NMR(CDCl$_3$) δ: 1.28(3H,d,J=7.2 Hz), 1.36(3H,d,J=6.6 Hz), 3.27(1H,dd,J=6.4,2.4 Hz), 3.30–3.75(5H,m), 4.18–4.31 (2H,m), 5.21(1H,d,J=14.0 Hz), 5.51(1H,d,J=14.0 Hz), 7.56–7.73(5H,m), 7.84(1H,d,J=7.6 Hz), 8.06(1H,d,J=8.4 Hz), 8.17(2H,d,J=8.8 Hz), 8.43(1H,d,J=5.8 Hz).

WORKING EXAMPLE 36-2

Sodium (4R,5S,6S)-6-[(R)-1-hydroxyethyl]-3-[2-(isoquinolin-1-yl)ethylthio]-4-methyl-7-oxo-1-azabicyclo [3.2.0]hept-2-ene-2-carboxylate Employing the compound produced in Working Example 36-1, the same reaction and purification as in Working Example 21-2 were conducted to give the title compound.

IR(KBr): 3340, 1748, 1591, 1391 cm$^{-1}$. $^1$H-NMR(D$_2$O) δ: 0.91(3H,d,J=7.2 Hz), 1.19(3H,d,J=6.4 Hz), 2.46(1H, quint,J=7.2 Hz), 3.08–3.42(4H,m), 3.62–3.70(2H,m), 4.09 (1H,quint, J=6.4 Hz), 7.64–7.84(3H,m), 7.96(1H,d,J=8.2 Hz), 8.32–8.39(2H,m).

WORKING EXAMPLE 37-1

4-Nitrobenzyl (4R,5S,6S)-6-[(R)-1-hydroxyethyl]-4-methyl-3-[2-(1-methylimidazol-2-yl)ethylthio]-7-oxo-1-azabicyclo[3.2.0]hept-2-ene-2-carboxylate Employing 2-(2-benzoylthioethyl)-1-methylimidazole (1.48 g), the same reaction and purification as in Working Example 8-1 were conducted to give the title compound (837 mg).

IR(KBr): 1767, 1690, 1522 cm$^{-1}$. $^1$H-NMR(DMSO-d$_6$) δ: 1.14(3H,d,J=7.2 Hz), 1.16(3H,d,J=6.2 Hz), 2.96(2H,t,J=7.2

Hz), 3.1–3.6(4H,m), 3.54(3H,s), 3.85–4.1(1H,m), 4.16(1H, dd,J=2.6,9.4 Hz), 5.13(1H,brd,J=5.2 Hz), 5.29(1H,d,J=14.1 Hz), 5.46(1H,d,J=14.1 Hz), 6.80(1H,d,J=1.1 Hz), 7.03(1H, d,J=1.1 Hz), 7.72(2H,d,J=8.8 Hz), 8.24(2H,d,J=8.8 Hz).

WORKING EXAMPLE 37-2
Sodium (4R,5S,6S)-6-[(R)-1-hydroxyethyl]-4-methyl-3-[2-(1-methylimidazol-2-yl)ethylthio]-7-oxo-1-azabicyclo[3.2.0]hept-2-ene-2-carboxylate Employing the compound produced in Working Example 37-1 (650 mg), the same reaction and purification as in Working Example 1-2 were conducted to give the title compound (332 mg).

IR(KBr): 1752, 1593 cm$^{-1}$. $^1$H-NMR(D$_2$O) δ: 1.13(3H, d,J=7.2 Hz), 1.28(3H,d,J=6.2 Hz), 3.0–3.35(5H,m), 3.39 (1H,dd,J=2.4,6.2 Hz), 3.74(3H,s), 4.00(1H,dd,J=2.5,9.3 Hz), 4.23(1H,dq,J=6.2,6.2 Hz), 7.22(1H,s), 7.24(1H,s).

WORKING EXAMPLE 38-1
4-Nitrobenzyl (4R,5S,6S)-6-[(R)-1-hydroxyethyl]-4-methyl-7-oxo-3-[2-(1-phenylimidazol-2-yl)ethylthio]-1-azabicyclo[3.2.0]hept-2-ene-2-carboxylate Employing 2-(2-acetylthioethyl)-1-phenylimidazole (1.48 g), the same reaction and purification as in Working Example 8-1 were conducted to give the title compound (837 mg).

IR(KBr): 1769, 1705, 1522, 1501 cm$^{-1}$. $^1$H-NMR (CDCl$_3$) δ: 1.21(3H,d,J=7.4 Hz), 1.36(3H,d,J=6.2 Hz), 2.8–3.55(5H,m), 3.24(1H,dd,J=2.4,6.6H), 4.16(1H,dd,J=2.4,9.2 Hz), 4.27(1H,dq,J=6.2,6.6 Hz), 5.20(1H,d,J=14.0 Hz), 5.48(1H,d,J=14.0 Hz), 7.02(1H,d,J=1.5 Hz), 7.10(1H, d,J=1.5 Hz), 7.2–7.6(5H,m), 7.63(2H,d,J=8.6 Hz), 8.20(2H, d,J=8.6 Hz).

WORKING EXAMPLE 38-2
Sodium (4R,SS,6S)-6-[(R)-1-hydroxyethyl]-4-methyl-7-oxo-3-[2-(1-phenylimidazol-2-yl)ethylthio]-1-azabicyclo[3.2.0]hept-2-ene-2-carboxylate Employing the compound produced in Working Example 38-1 (650 mg), the same reaction and purification as in Working Example 1-2 were conducted to give the title compound (403 mg).

IR(KBr): 1748, 1597, 1501 cm$^{-1}$. $^1$H-NMR(D$_2$O) δ: 1.01(3H,d,J=7.0 Hz), 1.30(3H,d,J=6.6 Hz), 2.7–3.2(5H,m), 3.28(1H,dd,J=2.0,6.0 Hz), 3.70(1H,dd,J=2.0,8.8 Hz), 4.21 (1H,dq,J=6.0,6.6 Hz), 7.14(1H,s), 7.25(1H,s), 7.35–7.65 (5H,m).

Structural Formulae of the Compounds of Working Examples are as Follows.

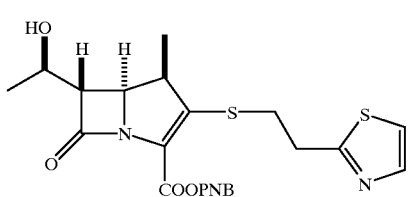

1-1

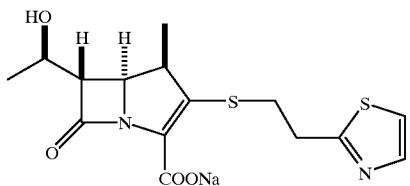

1-2

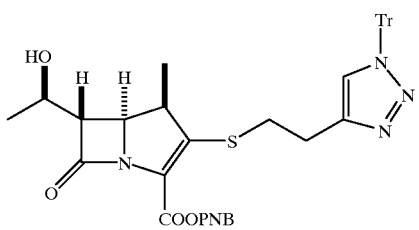

2-1

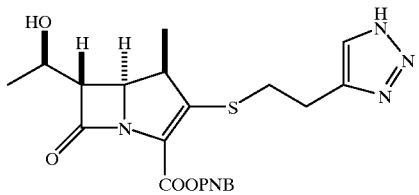

2-2

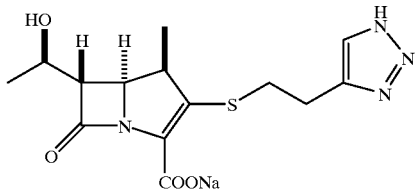

2-3

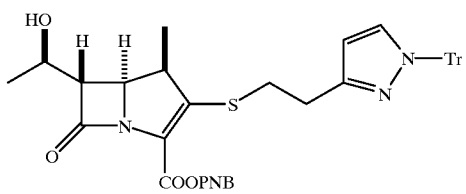

3-1

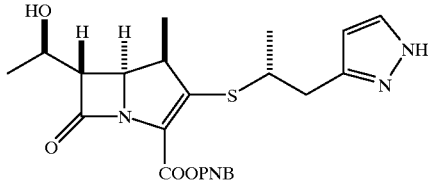

3-2

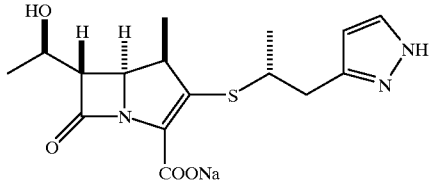

3-3

-continued
4-1
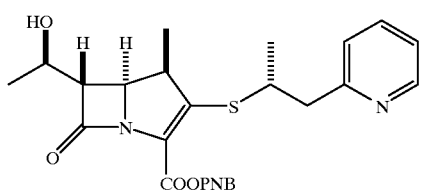
4-2
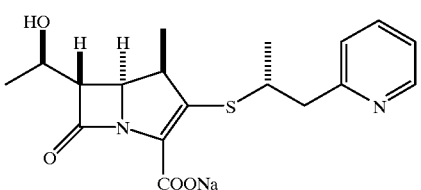
5-1
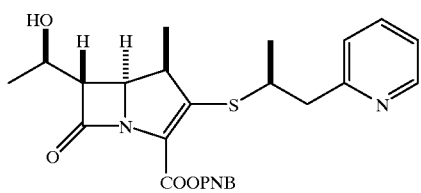
5-2
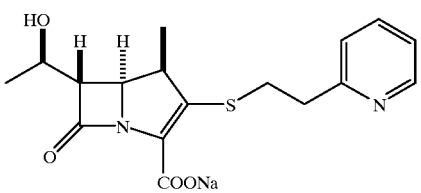
6-1
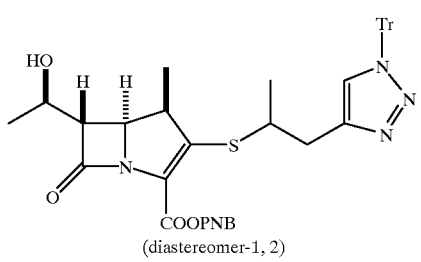
(diastereomer-1, 2)
6-2
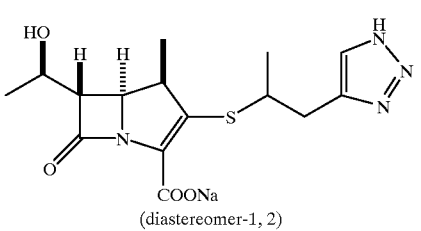
(diastereomer-1, 2)
7-1
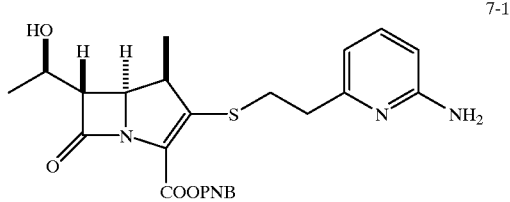
7-2
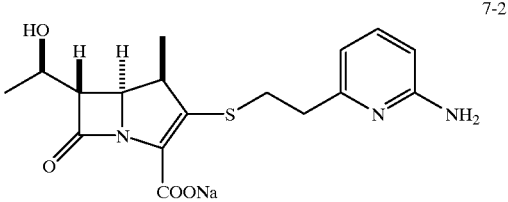
8-1
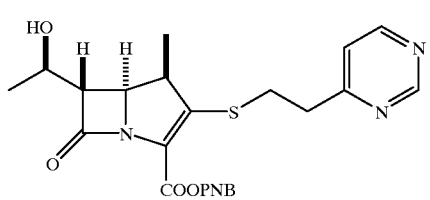
8-2
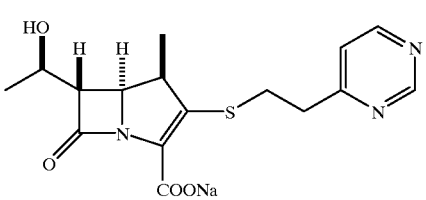
9
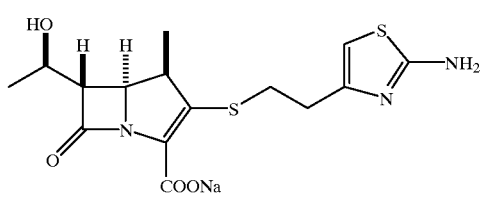
10-1
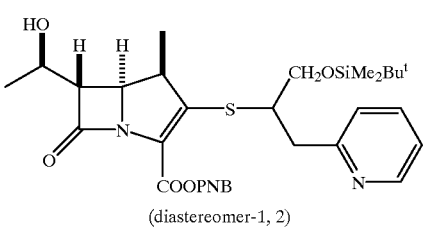
(diastereomer-1, 2)
10-2
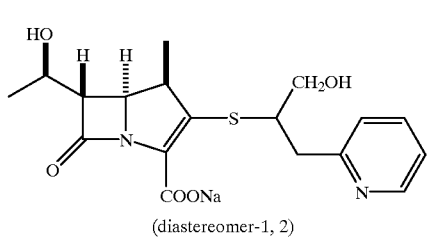
(diastereomer-1, 2)
11-1
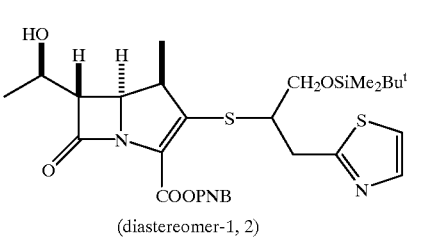
(diastereomer-1, 2)

-continued
11-2
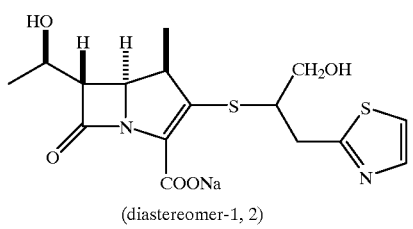
(diastereomer-1, 2)
12-1
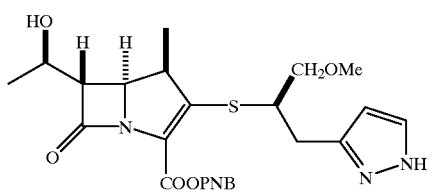
12-2
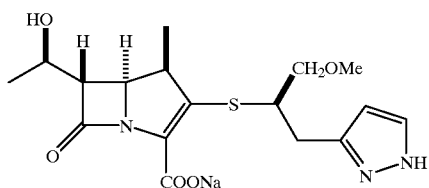
13-1
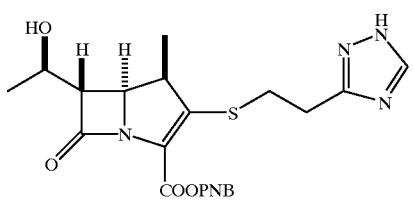
13-2
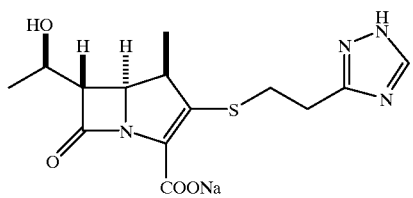
14-1
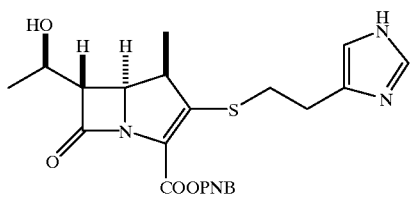
14-2
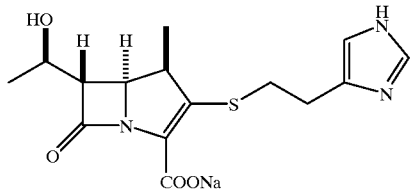
15-1
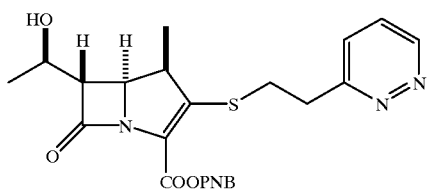
15-2
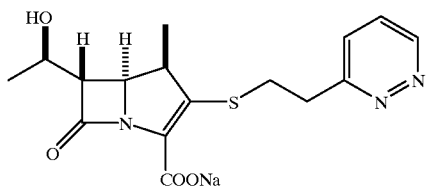
16-1
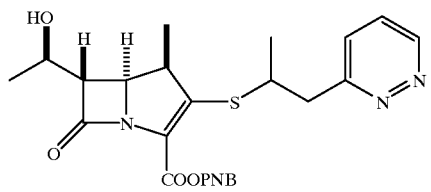
(diastereomer 1, 2)
16-2
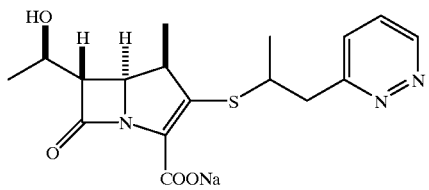
(diastereomer 1)
17
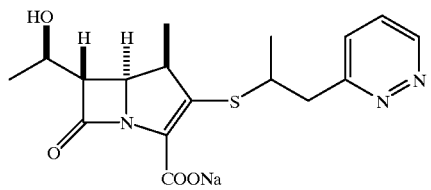
(diastereomer 2)
18-1
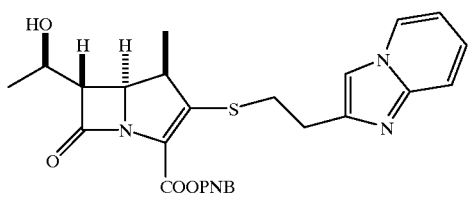
18-2
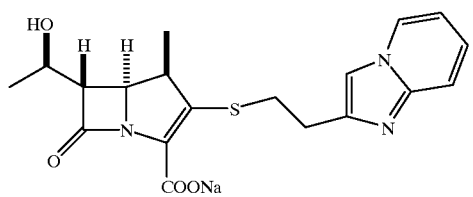

-continued
19-1
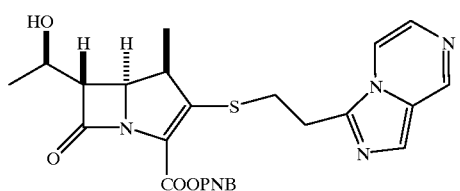
19-2
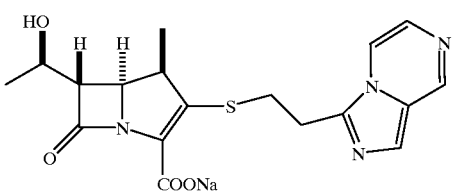
20-1
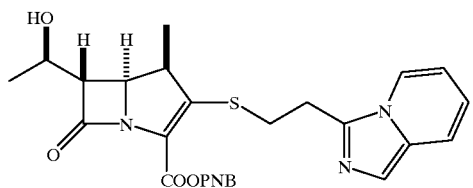
20-2
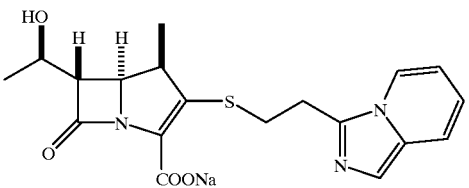
21-1
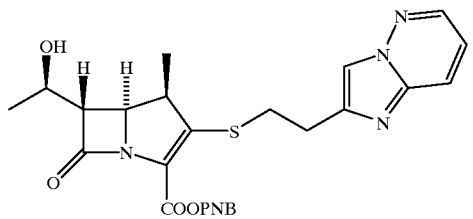
21-2
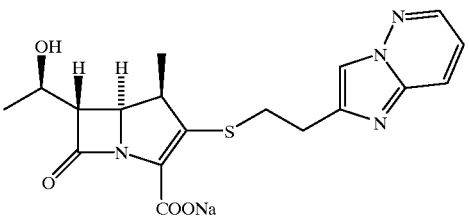
22-1
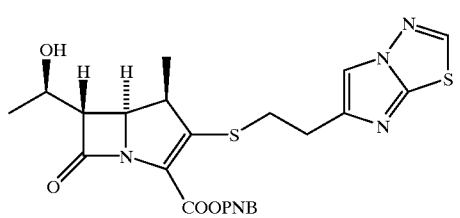
22-2
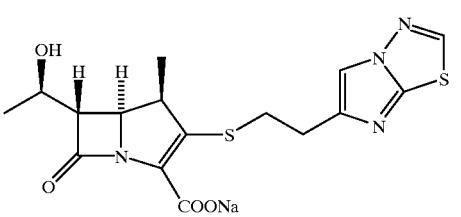
23-1
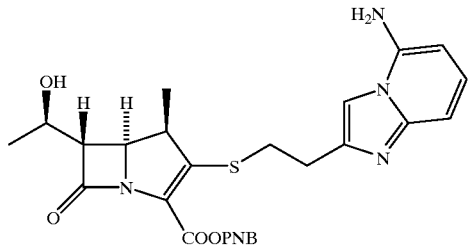
23-2
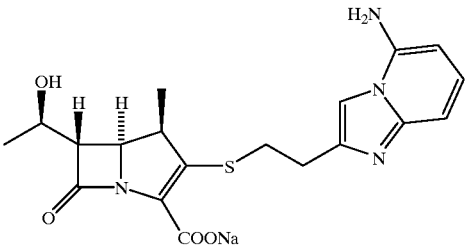
24-1
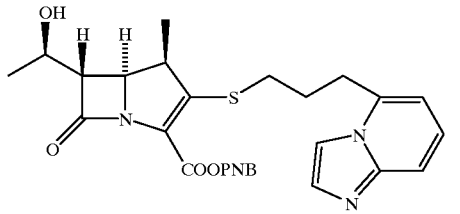
24-2
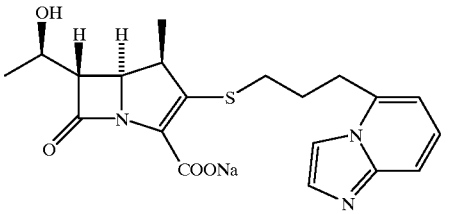
25-1
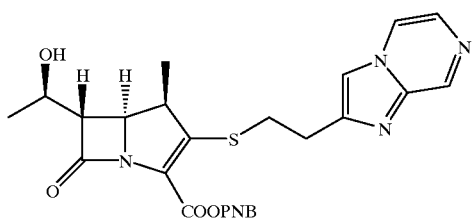
25-2
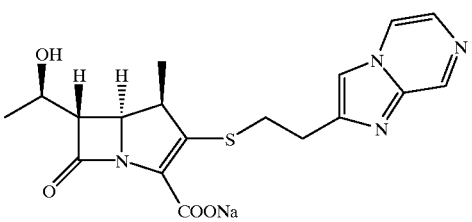

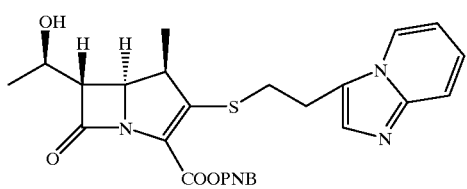
26-1
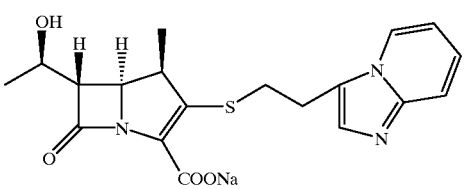
26-2
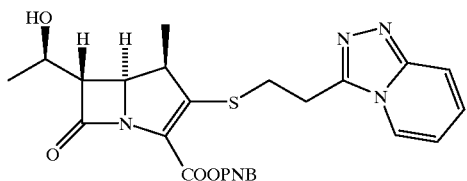
27-1
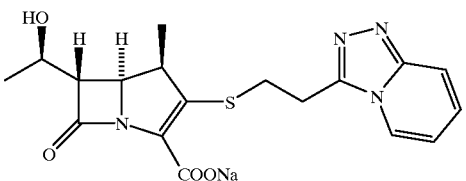
27-2
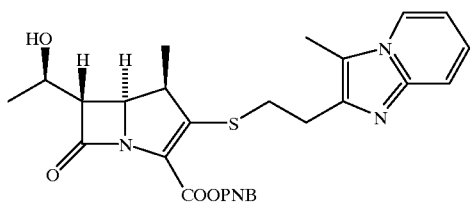
28-1
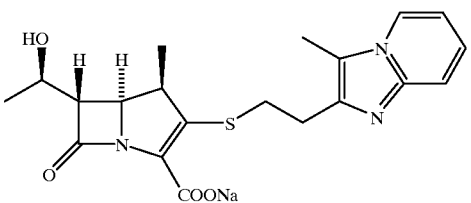
28-2
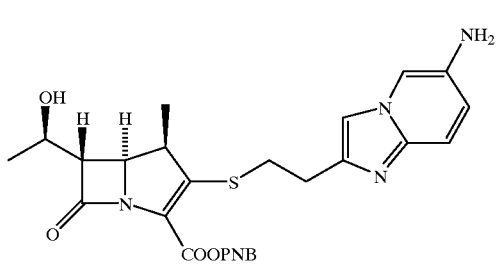
29-1
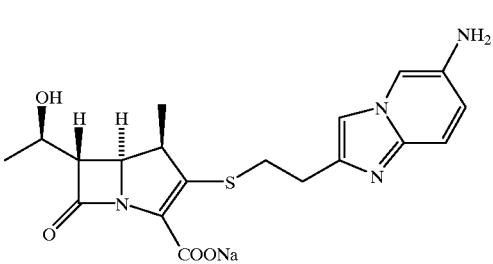
29-2
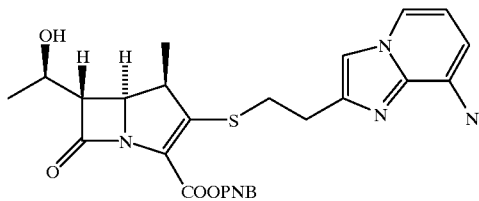
30-1
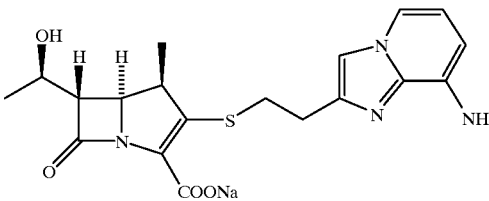
30-2
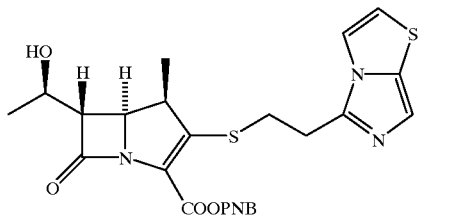
31-1
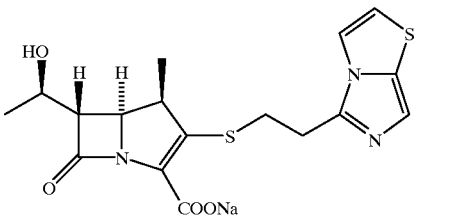
31-2
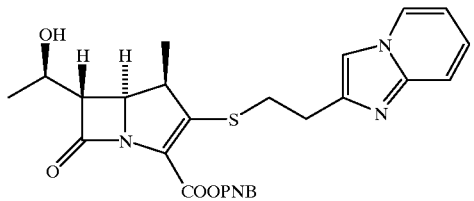
32-1
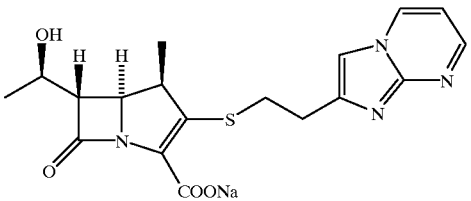
32-2

-continued 33-1
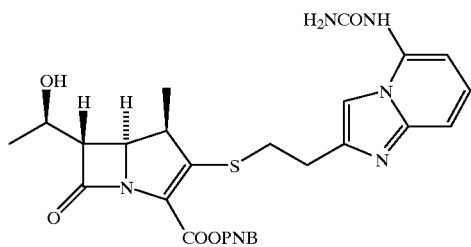

33-2
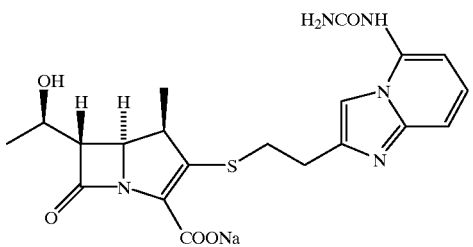

34-1
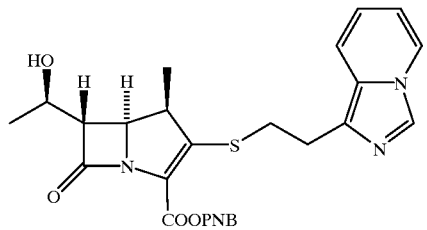

34-2
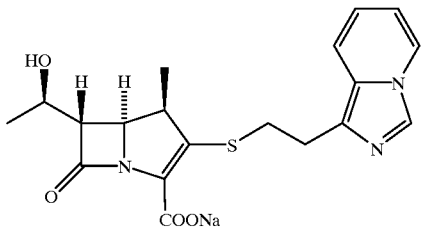

35-1
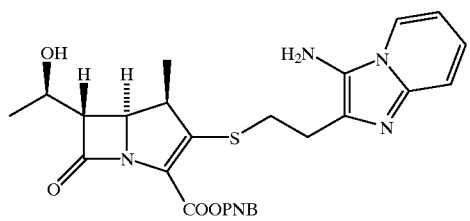

35-2
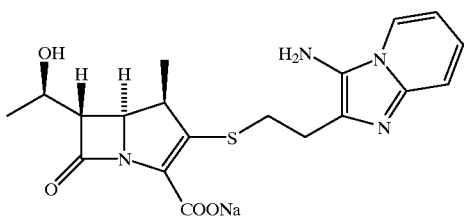

36-1
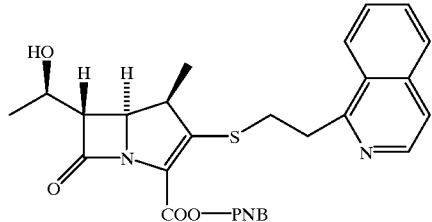

36-2
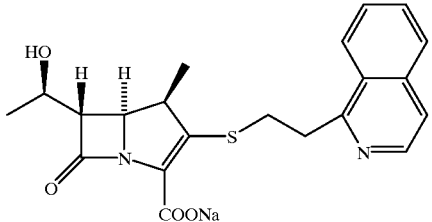

37-1
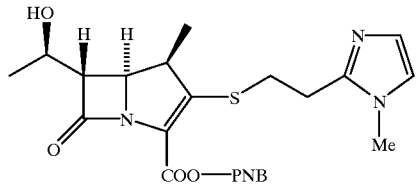

37-2
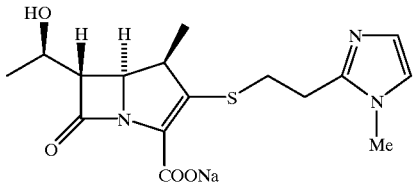

38-1
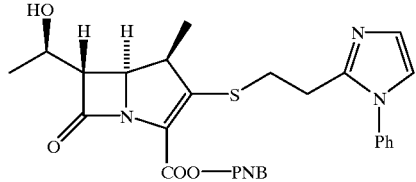

38-2
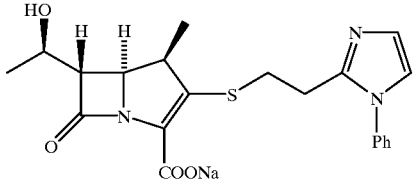

Test Example
Minimum Inhibitory Concentration (MIC)

The minimum inhibitory concentration [MIC (unit: $\mu$g/ml)] of the test compound was determined by an agar dilution method. More specifically, 0.25 ml of an aqueous solution of the test compound diluted stepwise was put into a Petri dish, which was then mixed with 9.75 ml of Muller-Hinton agar containing fildis enrichment [F-MH medium. fildis enrichment (5%)]). On thus-prepared mixed agar plate, a suspension of the test bacteria (about $10^6$ CFU/ml) was spread, which was incubated at 37° C. overnight. The minimum concentration of the test compound to completely inhibit the growth of the test bacteria was expressed as MIC.

TABLE 1

| | MIC (μg/ml) 10⁶CFU/ml | |
|---|---|---|
| name of strain | E. coli NHIJ | H. influenzae |
| Compound | JC-2 | NN400 |
| Medium | F-MH | F-MH |
| Imipenem | 0.1 | 0.78 |
| Working Example 2–3 | 0.025 | 0.1 |
| Working Example 3–3 | 0.1 | 0.1 |
| Working Example 17 | 0.1 | 0.1 |
| Working Example 18–2 | 0.2 | 0.1 |
| Working Example 29–2 | 0.2 | 0.05 |
| Working Example 32–2 | 0.2 | 0.05 |
| Working Example 33–2 | 0.2 | 0.1 |

From the above results, it is clear that the carbapenem compounds of this invention have excellent antibacterial activities against bacterial strains clinically taken seriously.

INDUSTRIAL APPLICABILITY

Since the novel carbapenem compounds (I) produced by the method of this invention have excellent properties, for example, having antibacterial activities of a broad spectrum, the present invention provides a novel antibacterial agent useful clinically.

What is claimed is:

1. A carbapenem compound of the formula:

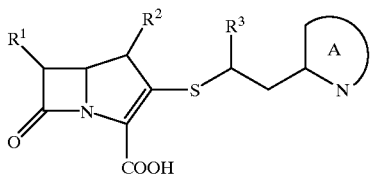

wherein $R^1$ is a $C_{1-4}$ alkyl group unsubstituted or substituted by 1 to 3 substituents selected from the group consisting of a cyano group, an amino group, a mono- or di-$C_{1-4}$ alkylamino group, a hydroxyl group, a $C_{1-4}$ alkyloxy group, a carbamoyloxy group, a $C_{1-4}$ alkylthio group, a $C_{1-4}$ alkylsulfonyl group, a halogen, a sulfamoyl group, a $C_{1-4}$ alkyloxy-carbonyl group and a sulfoxy group, $R^2$ is hydrogen or a $C_{1-4}$ alkyl group, $R^3$ is ① hydrogen, ② a $C_{1-6}$ alkyl group, ③ a $C_{2-6}$ alkenyl group, ④ a cyano group, ⑤ a $C_{1-6}$ alkyloxy group or ⑥ a $C_{1-6}$ alkylthio group, wherein each of the above ② and ③ is unsubstituted or substituted by 1 to 3 substituents selected from the group consisting of a halogen, a hydroxyl group, a $C_{1-6}$ alkyloxy group, an amino group and a mono- or di-$C_{1-4}$ alkylamino group, and ring A stands for a non-quaternarized N-containing aromatic heterocyclic ring or plural (fused) heterorings which is (1) a 5-membered aromatic heterocyclic ring selected from the group consisting of pyrrole ring, imidazole ring, pyrazole ring, triazole ring, tetrazole ring, thiazole ring and oxazole ring, (2) a 6-membered aromatic heterocyclic ring selected from the group consisting of pyridine ring, pyrazine ring, pyrimidine ring and pyridazine ring or (3) a condensed ring selected from the group consisting of purine ring, pyrrolopyrimidine ring, pyridopyrimidine ring, imidazopyridine ring, imidazopyridazine ring, imidazopyrimidine ring, imidazopyrazine ring, imidazothiazole ring and pyrazolopyrimidine ring, each of which may be unsubstituted or substituted by 1 to 3 substituents selected from the group consisting of ① an amino group, ② a carbamoyl group, ③ a $C_{1-6}$ alkyl group, ④ a $C_{6-10}$ aryl group, ⑤ a $C_{1-6}$ alkyloxy group, ⑥ a $C_{1-6}$ alkylthio group, ⑦ a 3- to 7-membered heterocyclic group containing 1 to 4 hetero atoms selected from the group consisting of nitrogen atom, oxygen atom and sulfur atom, each of which may be substituted by a halogen atom, hydroxyl group, $C_{1-6}$ alkyloxy group, amino group or mono or di-$C_{1-4}$ alkylamino, ⑧ a halogen atom, ⑨ a hydroxyl group and ⑩ a cyano group, provided that when the ring A is unsubstituted pyridine ring, $R^3$ stands for a group other than hydrogen, or an ester or salt thereof.

2. A compound as claimed in claim 1, wherein $R^1$ is 1-hydroxyethyl group.

3. A compound as claimed in claim 1, wherein $R^2$ is methyl group.

4. A compound as claimed in claim 1, wherein $R^3$ is a cyano group or a $C_{1-6}$ alkyl group unsubstituted or substituted by 1 to 3 substituents selected from the group consisting of a halogen, a hydroxl group, a $C_{1-6}$ alkyloxy group, an amino group and a mono- or di-$C_{1-4}$ alkylamino group.

5. A compound as claimed in claim 1, wherein $R^3$ is an $C_{1-6}$ alkyl group which is unsubstituted or substituted with a hydroxyl group or a $C_{1-4}$ alkyloxy group.

6. A compound as claimed in claim 1, wherein the non-quaternarized N-containing aromatic heterocyclic ring is (1) a 5-membered aromatic heterocyclic ring selected from the group consisting of pyrrole ring, imidazole ring, pyrazole ring, triazole ring, tetrazole ring, thiazole ring and oxazole ring, (2) a 6-membered aromatic heterocyclic ring selected from the group consisting of pyridine ring, pyrazine ring, pyrimidine ring and pyridazine ring or (3) a condensed ring selected from the group consisting of purine ring, pyrrolopyrimidine ring, pyridopyrimidine ring, imidazopyridazine ring and pyrazolopyrimidine ring.

7. A compound as claimed in claim 1, wherein the non-quaternarized N-containing aromatic heterocyclic ring is pyridazine ring, pyrazole ring, triazole ring, imidazopyridine ring, imidazopyrimidine ring, imidazopyrazine ring or imidazothiazole ring.

8. A compound as claimed in claim 1, wherein

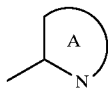

is (1) a 5-membered aromatic heterocyclic group selected from the group consisting of 2-thiazolyl, 2-amino-4-thiazolyl, 3-pyrazolyl, 1-triphenylmethyl-3-pyrazolyl, 4-imidazolyl, 1-methylimidazolyl-2-yl, 1-phenylimidazolyl-2-yl, 1,2,3-triazol-4-yl and 1,2,4-triazol-3-yl, (2) 6-membered aromatic heterocyclic ring selected from the group consisting of 2-pyridazinyl, 6-amino-2-pyridazinyl, 4-pyrimidinyl and 3-pyridazinyl, or (3) a condensed ring selected from the group consisting of imidazo[1,2-a]pyridin-2-yl, 3-methylimidazo[1,2-a]pyridin-2-yl, 3-aminoimidazo[1,2-a]pyridin-2-yl, 5-aminoimidazo[1,2-a]pyridin-2-yl, 6-aminoimidazo[1,2-a]pyridin-2-yl, 8-aminoimidazo[1,2-a]pyridin-2-yl, 5-ureidoimidazo[1,2-a]pyridin-2-yl, imidazo[1,2-a]pyridin-3-yl, imidazo[1,2-a]pyridin-5-yl, [1,2,4]triazolo[4,3-a]pyridin-3-yl, imidazo[1,5-a]pyridin-1-yl, imidazo[1,5-a]pyridin-3-yl, imidazo[1,2-b]pyridazin-2-yl, imidazo[2,1-b][1.3.4]thiadiazol-3-yl, imidazo[1,2-a]pyrazin-2-yl, imidazo[1,5-a]pyrazin-3-yl, imidazo[5,1-b]thiazol-5-yl and isoquinolin-1-yl.

9. A compound as claimed in claim 1, which is
(4R,5S,6S)-6-[(R)-1-hydroxyethyl]-4-methyl-7-oxo-3-[2-(1,2,3-triazol-4-yl)ethylthio]-1-azabicyclo[3.2.0]hept-2-ene-2-carboxylic acid, (4R,5R,6R)-6-[(R)-1-hydroxyethyl]-4-methyl-7-oxo-3-[2-(3-pyrazolyl)ethylthio]-1-azabicyclo[3.2.0]hept-2-ene-2-carboxylic acid, (4R,5R,6R)-6-[(R)-1-hydroxyethyl]-4-methyl-3-[1-methyl-2-(3-pyridazinyl)ethylthio]-7-oxo-1-azabicyclo[3.2.0]hept-2-ene-2-carboxylic acid, (4R,5R,6R)-6-[(R)-1-hydroxyethyl]-3-[2-(imidazo[1,2-a]pyridine-2-yl)ethylthio]4-methyl-7-oxo-1-azabicyclo[3.2.0]hept-2-ene-2-carboxylic acid, (4R,5R,6R)-3-[2-(6-aminoimidazo[1,2-a]pyridin-2-yl)ethylthio]-6-[(R)-1-hydroxyethyl]-4-methyl-7-oxo-1-azabicyclo[3.2.0]hept-2-ene-2-carboxylic acid, (4R,5R,6R)-6-[(R)-1-hydroxyethyl]-3-[2-(imidazo[1,2-a]pyrimidin-2-yl)ethylthio]-4-methyl-7-oxo-1-azabicyclo[3.2.0]hept-2-ene-2-carboxylic acid, (4R,5R,6R)-6-[(R)-1-hydroxyethyl]-4-methyl-7-oxo-3-[2-(5-ureidoimidazo[1,2-a]pyridin-2-yl)ethylthio]-1-azabicyclo[3.2.0]hept-2-ene-2-carboxylic acid, (4R,5R,6R)-6-[(R)-1-hydroxyethyl]-3-[2-(imidazo[1,5-a]pyridin-3-yl)ethylthio]-4-methyl-7-oxo-1-azabicyclo[3.2.0]hept-2-ene-2-carboxylic acid, (4R,5R,6R)-6-[(R)-1-hydroxyethyl]-3-[2-(imidazo[1,2-a]pyrazin-2-yl)ethylthio]-4-methyl-7-oxo-1-azabicyclo[3.2.0]hept-2-ene-2-carboxylic acid, or (4R,5R,6R)-6-[(R)-1-hydroxyethyl]-3-[2-(imidazo[5,1-b]thiazol-5-yl)ethylthio]-4-methyl-7-oxo-1-azabicyclo[3.2.0]hept-2-ene-2-carboxylic acid, or an ester or salt thereof.

10. A method for producing a compound as claimed in claim 1, which comprises reacting a compound of the formula:

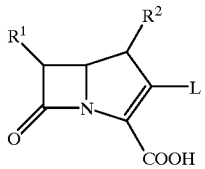

wherein L is a group capable of leaving, and the other symbols are of the same meanings as defined in claim 1, or an ester or salt thereof with a compound of the formula:

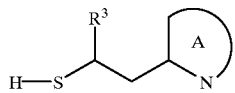

wherein the symbols are of the same meanings as defined in claim 1, or a salt thereof.

11. A method for producing a compound as claimed in claim 1, which comprises reacting a compound of the formula:

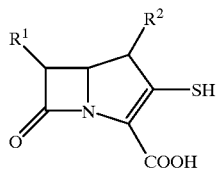

wherein the symbols are of the same meanings as defined in claim 1, or an ester or salt thereof with a compound of the formula:

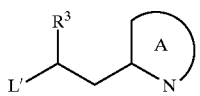

wherein L' stands for a group capable of leaving and the other symbols are of the same meanings as defined in claim 1, or salt thereof.

12. An antibacterial composition which comprises an effective amount of a compound as claimed in claim 1 and a pharmaceutically acceptable carrier, diluent or excipient.

13. A method for treating bacterial infection which comprises administering an effective amount of a compound as claimed in claim 1, optionally together with a pharmaceutically acceptable carrier, diluent or excipient to a patient suffering from bacteria infection.

14. A method of making an antibacterial composition, which comprises mixing an effective amount of a compound as claimed in claim 1 with a pharmaceutically acceptable carrier, diluent or excipient.

* * * * *